(12) United States Patent
Miller et al.

(10) Patent No.: US 8,173,646 B2
(45) Date of Patent: *May 8, 2012

(54) FAB I INHIBITORS

(75) Inventors: William H. Miller, Collegeville, PA (US); Kenneth A. Newlander, West Chester, PA (US); Mark A. Seefeld, Collegeville, PA (US); Irene N. Uzinskas, Villanova, PA (US); Walter E. Dewolf, Jr., Glenmoore, PA (US); Dalia R. Jakas, Norristown, PA (US)

(73) Assignee: Affinium Pharmaceuticals, Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,729

(22) Filed: Jul. 6, 2010

(65) Prior Publication Data

US 2011/0190283 A1    Aug. 4, 2011

Related U.S. Application Data

(63) Continuation of application No. 12/403,078, filed on Mar. 12, 2009, now Pat. No. 7,790,716, which is a continuation of application No. 11/779,578, filed on Jul. 18, 2007, now Pat. No. 7,524,843, which is a continuation of application No. 11/007,927, filed on Dec. 9, 2004, now Pat. No. 7,557,125, which is a continuation of application No. 10/089,755, filed as application No. PCT/US00/27844 on Oct. 6, 2000, now Pat. No. 6,846,819.

(60) Provisional application No. 60/158,704, filed on Oct. 8, 1999.

(51) Int. Cl.
*A61K 31/4375* (2006.01)
*C07D 265/36* (2006.01)
(52) U.S. Cl. .................. 514/230.5; 544/105
(58) Field of Classification Search .......... 514/230.5, 514/258; 544/105, 333
See application file for complete search history.

(56) References Cited

U.S. PATENT DOCUMENTS

| | | | |
|---|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Cagle et al. |
| 6,399,629 B1 | 6/2002 | Chamberland et al. |
| 6,406,880 B1 | 6/2002 | Thornton |
| 6,423,341 B1 | 7/2002 | Yamaguchi |
| 6,423,741 B1 | 7/2002 | Khanuja et al. |
| 6,428,579 B1 | 8/2002 | Valentini |
| 6,432,444 B1 | 8/2002 | Fischetti et al. |
| 6,436,980 B1 | 8/2002 | Leger et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |

(Continued)

FOREIGN PATENT DOCUMENTS

CA    2444597    10/2002

(Continued)

OTHER PUBLICATIONS

Abou-Gharbia et al., "Psychotropic Agents: Synthesis and Antipysychotic Activity of Substituted B-Carbolines," *J. Med. Chem.*, 30(6), 1987, pp. 1100-1115.
Ahsan et al., "Reserpine Anlogues: Synthesis of B-Carboline Derivatives," *J. Chem. Soc.*, 1963, pp. 3928-3920.
Bergler et al., "Protein EnvM is the NADH-dependent Enoyl-ACP Reductase (FabI) of *Escherichia coli*," *J. Biol. Chem.*, 269(8), 1994, pp. 5493-5496.
Claus et al., "Formaldehydabspaltende Phenolearbonaaurederlvate," *Monatsh. Chem.*, 97, 1966, pp. 271-279.
Database CA on STN, AN 7:66733, Rosenmund et al., "Chemistry of indole II . . . ," Chem Ber. 103(2), 1970, pp. 496-509.

(Continued)

*Primary Examiner* — Taofiq A Solola
(74) *Attorney, Agent, or Firm* — Goodwin Procter LLP

(57) ABSTRACT

Compounds of the Formula (I) are disclosed which are Fab I inhibitors and are useful in the treatment of bacterial infections.

8 Claims, No Drawings

U.S. PATENT DOCUMENTS

| | | | |
|---|---|---|---|
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,524,843 B2 | 4/2009 | Miller et al. |
| 7,557,125 B2 | 7/2009 | Miller et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 2009/0042927 A1 | 2/2009 | Pauls et al. |
| 2009/0156578 A1 | 6/2009 | Pauls et al. |
| 2010/0093705 A1 | 4/2010 | Sargent et al. |
| 2010/0130470 A1 | 5/2010 | Pauls et al. |
| 2011/0098277 A1 | 4/2011 | Burgess et al. |
| 2011/0124633 A1 | 5/2011 | Berman et al. |

FOREIGN PATENT DOCUMENTS

| | | |
|---|---|---|
| EP | 0407200 | 1/1991 |
| EP | 1000935 | 5/2000 |
| HU | 210679 | 7/1993 |
| HU | 0203122 | 1/2003 |
| WO | WO-93/04035 | 3/1993 |
| WO | WO-95/18619 | 7/1995 |
| WO | WO-96/00730 | 1/1996 |
| WO | WO-97/48696 | 12/1997 |
| WO | WO-98/57952 | 12/1998 |
| WO | WO-99/24406 | 5/1999 |
| WO | WO-00/27628 | 5/2000 |
| WO | WO-00/57933 | 10/2000 |
| WO | WO-01/14364 | 3/2001 |
| WO | WO-01/26652 | 4/2001 |
| WO | WO-01/26654 | 4/2001 |
| WO | WO-01/27103 | 4/2001 |
| WO | WO-01/41573 | 6/2001 |
| WO | WO-01/48248 | 7/2001 |
| WO | WO-01/70172 | 9/2001 |
| WO | WO-02/10332 | 2/2002 |
| WO | WO-02/42273 | 5/2002 |
| WO | WO-02/48097 | 6/2002 |
| WO | WO-02/064572 | 8/2002 |
| WO | WO-03/086396 | 10/2003 |
| WO | WO-2004/014869 | 2/2004 |
| WO | WO-2004/052890 | 6/2004 |
| WO | WO-2004/082586 | 9/2004 |
| WO | WO-2007/053131 | 5/2007 |
| WO | WO-2007/067416 | 6/2007 |
| WO | WO-2008/009122 | 1/2008 |

OTHER PUBLICATIONS

Database CAOLD on STN, AN CA51:10524d, Hellman et al., "N-Mannich bases (VI) condensation . . . ," Direct Submission, 1953, 1 page.

Database CAPLUS on STN, AN 1977:439214, Misztal et al., "Synthesis and pharmacologic properties of pyridoyl . . . ," *Arch. Immunol. Ther. Exp.*, 24(6), 1976, pp. 851-862.

Database CAPLUS on STN, AN 1986:68547, Stuetz et al., "Synthesis and Structure Activity . . . ," *J. Med. Chem.*, 29(1), 1986, pp. 112-125.

Database CAPLUS on STN, AN 1991:428908, Fuse et al., "Preparation of cinnamamide derivatives . . . ," EP407200A1, 1991, 3 pages.

Database CAPLUS on STN, AN 1999:325910, Aslanian et al., "Preparation of phenylalkylimidazoles . . . ," WO/99/24406, 1999, 2 pages.

Database Crossfire Beilstein, Database Accession No. 2819049, 2819050, XP002216033, 1966, 2 pages.

Grassberger et al., "Preparation and Antibacterial Activities of New 1,2,3-Diazaborine Derivatives and Analogues," *J. Med. Chem.*, 27, 1984, pp. 947-953.

Heath et al., "A Triclosan-Resistant Bacterial Enzyme," *Nature*, 406, 2000, pp. 145-146.

Heath et al., "Regulation of Fatty Acid Elongation and Initiation by Acyl-Acyl Carrier Protein in *Escherichia coli*," *J. Biol. Chem.*, 271(4), 1996, pp. 1833-1836.

Heck, *Organic Reactions*, 27, 1982, pp. 345-390.

Himmler et al., "Synthesis and Antibacterial in Vitro Activity of Novel Analogues of Nematophin," *Bioorg. Med. Chem. Lett.*, 8(15), 1998, pp. 2045-2050.

Hungarian Search Report for Hungarian Patent Application No. P0203122, dated Dec. 31, 2003, 1 page.

International Search Report dated Oct. 4, 2000 for PCT Application No. PCT/US2000/15154, 2 pages.

International Search Report dated Jan. 25, 2001 for PCT Application No. PCT/US2000/27844, 3 pages.

International Search Report dated Jan. 29, 2001 for PCT Application No. PCT/US2000/27591, 1 page.

International Search Report dated Feb. 22, 2001 for PCT Application No. PCT/US2000/27619, 3 pages.

International Search Report dated Apr. 21, 2004 for PCT Application No. PCT/US2003/38706, 5 pages.

International Search Report dated Oct. 13, 2004 for PCT Application No. PCT/IB2004/001261, 3 pages.

International Search Report dated Apr. 20, 2005 for PCT Application No. PCT/US2002/10332, 3 pages.

International Search Report dated Jun. 14, 2007 for PCT Application No. PCT/US2005/019805, 4 pages.

International Search Report dated Sep. 12, 2007 for PCT Application No. PCT/US2006/045903, 6 pages.

International Search Report dated Oct. 26, 2007 for PCT Application No. PCT/CA2007/001277, 3 pages.

International Search Report dated Apr. 7, 2008 for PCT Application No. PCT/CA2008/000300, 5 pages.
Li et al., "Synthesis and Antistaphylococcal Activity of Nematophin and Its Analogs," *Bioorg. Med. Chem. Lett.*, 7(10), 1977, pp. 1349-1352.
Jossang-Yanagida et al., "Tetrahydropyridoazepines and Tetrahydropyridoazepinones from the Corresponding Dihydroquinolones," *J. Heterocycl. Chem.*, 15, 1978, pp. 249-251.
Karlowsky et al., "In Vitro Activity of API-1252, a Novel FabI Inhibitor, against Clinical Isolates of *Staphylococcus aureus* and *Staphylococcus epidermidis*," *Antimicrob. Agents Chemother.*, 51(4), 2007, pp. 1580-1581.
Levy et al., "Molecular Basis of Triclosan Activity," *Nature*, 398, 1999, pp. 383-384.
McMurray et al., "Triclosan Targets Lipid Synthesis," *Nature*, 394, 1998, pp. 531-532.
Miller et al., "Discovery of Aminopyridine-Based Inhibitors of Bacterial Enoyl-ACP Reductase (FABI)," *J. Med. Chem.*, 45, 2002, pp. 3246-3256.
Misztal et al., "Synthesis and Pharmacologic Properties of Pyridol Derivatives of 3-Methylaminoindole 2-Methyltryptamine and Isostryptamine," *Arch. Immunol. Ther. Exp.*, 24(6), 1976, pp. 851-852.
Pachter et al., "The Chemistry of Hortiamine and 6-Methoxyhetsinine," *J. Amer. Chem.* 83, 1961, pp. 635-642.

Patent Abstract of Japan for Japanese Patent Publication No. JP 11-302173, published Nov. 2, 2009, 1 page.
Payne et al., "Bacterial Fatty-Acid Biosynthesis: A Genomics-Driven Target for Antibacterial Drug Discovery," *Drug Discov. Today*, 6(10), 2001, pp. 537-541.
Rehse et al., "Dopaminanaloge 1,2,3,4-Tetrahydro-B-Carboline," *Arch. Pharm.*, 311(1), 1978, pp. 11-18.
Seefeld et al., "Indole Naphthyridinones as Inhibitors of Bacterial Enoyl-ACP Reductases FabI and FabK," *J. Med. Chem.*, 46, 2003, pp. 1627-1635.
Shoji et al., "Two Novel Alkaloids from Evodia rutaecarpa," *J. Nat. Prod.*, 52(5), 1989, pp. 1160-1162.
Sladowska et al., "Synthesis and Properties of Amides of 1-Benzyl-3-methyl and 1-Butyl-3-phenyl-7-methyl-4-oxo-2-thioxo (2,4-dioxo)-1,2,3,4-tetrahydropyrido-[2,3-d]pyrimidine-6-carboxylic acids," *Farmaco Sci.*, 41, 1986, pp. 954-963.
Stuetz et al., "Synthesis and Structure-Activity Relationships of Naftifine-Related Allylamine Antimycotics," *J. Med. Chem.*, 29(1), 1986, pp. 112-125.
Turnowsky et al., "envM Genes of *Salmonella typhimurium* and *Escherichia coli*," *J. Bacteriol.*, 171(12), 1989, pp. 6555-6565.
Ward et al., "Kinetic and Structural Characteristics of the Inhibition of Enoyl (Acyl Carrier Protein) Reductase by Triclosan," *Biochemistry*, 38(38), 1999, pp. 12514-12525.

SEQUENCE LISTING

```
<160> NUMBER OF SEQ ID NOS: 4

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcctcgaga tgttaaatct tgaaaacaaa acatatgtc                           39

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcggatcca atcaagtcag gttgaaatat cca                                 33
```

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgggctta aatcttgaaa acaaaaca                                          28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tatgttttgt tttcaagatt taagcc                                            26
```

FAB I INHIBITORS

RELATED APPLICATIONS

This application is a continuation of U.S. Ser. No. 12/403,078, filed Mar. 12, 2009 now U.S. Pat. No. 7,790,716, which is a continuation of U.S. Ser. No. 11/779,578, filed Jul. 18, 2007, now U.S. Pat. No. 7,524,843, which is a continuation of U.S. Ser. No. 11/007,927, filed Dec. 9, 2004, now U.S. Pat. No. 7,557,125, which is a continuation of U.S. Ser. No. 10/089,755, filed Apr. 3, 2002, now U.S. Pat. No. 6,846,819, which is a national stage of PCT/US00/27844, filed Oct. 6, 2000, which claims priority to U.S. Ser. No. 60/158,704, filed Oct. 8, 1999, each of which is hereby incorporated by reference in its entirety.

FIELD OF THE INVENTION

This invention relates to pharmaceutically active compounds which inhibit Fab I and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

Fab I (previously designated EnvM) functions as an enoyl-ACP reductase (Bergler, et al. (1994), J. Biol. Chem. 269, 5493-5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans2-enoyl-ACP, which in turn is converted to acyl-ACP by NADH-dependent enoyl-ACP reductase (Fab I). Further rounds of this cycle, adding two carbon atoms per cycle, eventually lead to palmitoly-ACP (16C), where upon the cycle is stopped largely due to feedback inhibition of Fab I by palmitoly-ACP (Heath, et al. (1996), J. Biol. Chem. 271, 1833-1836). Thus, Fab I is a major biosynthetic enzyme and is a key regulatory point in the overall synthetic pathway of bacterial fatty acid biosynthesis. Therefore, Fab I is an ideal target for antibacterial intervention.

Studies have shown that diazaborine antibiotics inhibit fatty acid, phospholipid and lipopolysaccharide (LPS) biosynthesis and that the antibacterial target of these compounds is Fab I. For example, derivative 2b 18 from Grassberger, et al. (1984) J. Med. Chem. 27, 947-953 has been reported to be a non-competitive inhibitor of Fab I (Bergler, et al. (1994) J. Biol. Chem. 269, 5493-5496). Also, plasmids containing the Fab I gene from diazaborine resistant S. typhimurium conferred diazaborine resistance in E. coli (Turnowsky, et al, (1989) J. Bacterial., 171, 6555-6565). Furthermore, inhibition of Fab I either by diazaborine or by raising the temperature in a Fab I temperature sensitive mutant is lethal. These results demonstrate that Fab I is essential to the survival of the organism (Bergler, et al, (1994) J. Biol. Chem. 269, 5493-5496).

Recent studies have shown that Fab I is also the target for the broad spectrum antibacterial agent triciosan (McMurry, et al, (1998) Nature 394, 531-532). A crystal structure of the E. Coli Fab I complexed with NAD and triciosan shows that triciosan acts as a site-directed, very potent inhibitor of Fab I by mimicking its natural substrate (Levy, et al, (1999) Nature 398, 383-384). Ward, et al ((1999) Biochem. 38, 12514-12525) have shown that there is no evidence for the formation of a covalent complex between Fab I and triciosan, which would be analogous to the diazaborines; triciosan differs from these compounds in that it is a reversible inhibitor of Fab I. The structural data for the complex of Fab I with NAD and triciosan provides important information about Fab I as a therapeutic target.

Importantly, it has now been discovered that certain compounds are Fab I inhibitors and have antibacterial activity, and, therefore, may be useful for the treatment of bacterial infections in mammals, particularly in man.

Additionally, two of the instant Fab I inhibiting compounds have been found to be inhibitors of Streptococcus Fab K. Fab I is not present in Streptococcus, and is not essential in Pseudomonas. There is also reason to believe that Fab I may not be essential in Enterococcus. In all of these organisms, another enoyl reductase, termed Fab K, is present (Heath, R. J.; Rock, Colo., Nature (2000), 406, 145-146). Pseudomonas and Enterococcus contain both Fab I and Fab K, and Streptococcus contains only Fab K. Consequently, pure Fab I inhibitors are not expected to have antibacterial activity in these organisms. Thus, compounds that inhibit both Fab I and Fab K have the potential to be broad-spectrum antibacterial agents.

SUMMARY OF THE INVENTION

This invention comprises compounds of the formula (I), as described hereinafter, which inhibit Fab I and are useful in the treatment of bacterial infections.

This invention is also a pharmaceutical composition comprising a compound according to formula (I) and a pharmaceutically acceptable carrier.

This invention is a method of treating bacterial infections by inhibiting Fab I and, for certain compounds, also inhibiting Fab K. In a particular aspect, the compounds of this invention are useful as antibacterial agents.

This invention also comprises the preparation and purification of crotonoyl-ACP and the use of this purified enzyme in a Fab I enzyme inhibition assay.

DETAILED DESCRIPTION

This invention comprises compounds of formula (I):

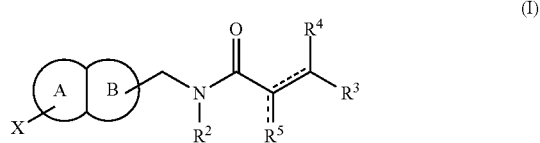

wherein:

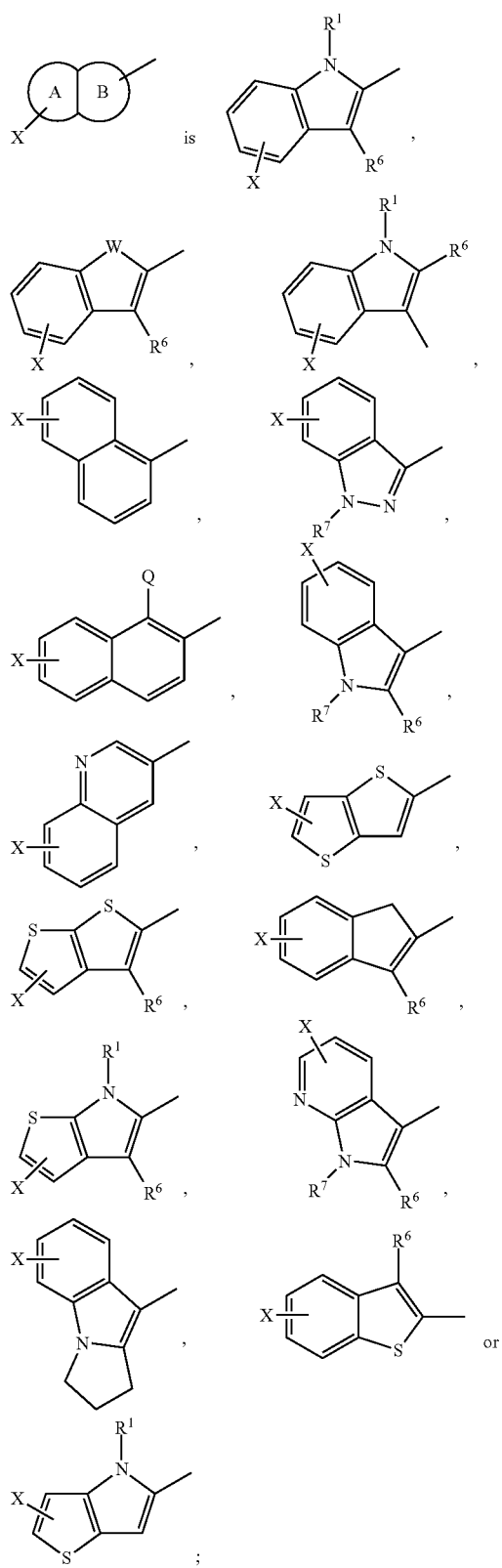

$R^1$ is H or $C_{1-4}$alkyl;
$R^2$ is H, $C_{1-4}$alkyl or $C_{3-6}$cycloalkyl;

$R^3$ is

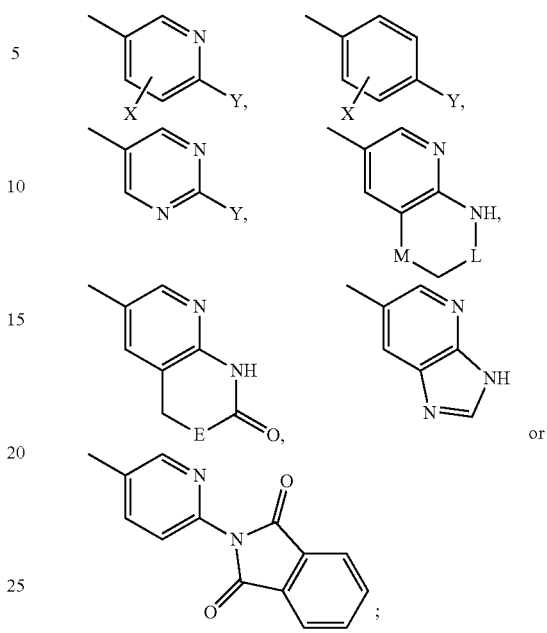

$R^4$ is H or $C_{1-4}$alkyl;

indicates that one of the two designated bonds is a double bond and the other is a single bond;
$R^5$ is $CH_2$ when the bond to which it is attached is a double bond; or $R^5$ is H or $C_{1-4}$alkyl when the bond to which it is attached is a single bond;
$R^6$ is H or $C_{1-4}$alkyl;
$R^7$ is H, $C_{1-6}$alkyl or —$C_{0-6}$alkyl-Ar;
Y is H, $C_{1-4}$alkyl, $N(R')_2$, NHC(O)R', NHCH$_2$C(O)R' or NHC(O)CH=CHR';
each X independently is H, $C_{1-4}$alkyl, $CH_2OH$, OR', SR', CN, $N(R')_2$, $CH_2N(R')_2$, $NO_2$, $CF_3$, $CO_2R'$, $CON(R')_2$, COR', NR'C(O)R', F, Cl, Br, I or —$S(O)_rCF_3$;
W is S or O;
Q is H or $C_{1-4}$alkyl;
M is $CH_2$ or O;
L is $CH_2$ or C(O);
E is O or NR';
each R' independently is H, $C_{1-6}$alkyl or —$C_{0-6}$alkyl-Ar, and
r is 0, 1 or 2;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

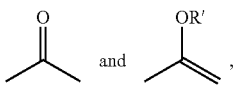 and each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded, carriers which release the active parent drug according to formula (I) in vivo.

The compounds of formula (I) inhibit Fab I. Inhibition of this enzyme is useful in the treatment of bacterial infections. Also, the compounds of this invention may be useful as antifungal agents. Additionally, the compounds may be useful in combination with known antibiotics.

With respect to formula (I), this invention preferably includes compounds of formula (Ia):

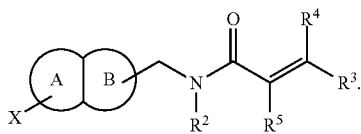

(Ia)

in which $R^2$, $R^3$, $R^4$, $R^5$ and X are as defined for formula (I) compounds.

With respect to formula (I), this invention preferably includes compounds of formula (II):

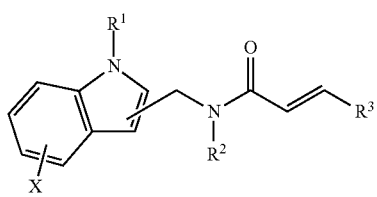

(II)

in which $R^1$, $R^2$, $R^3$ and X are as defined for formula (I) compounds.

With respect to formula (II), this invention preferably includes compounds of formula (IIa):

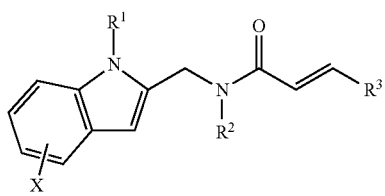

(IIa)

in which $R^1$, $R^2$, $R^3$ and X are as defined for formula (I) compounds.

In particular, with respect to formula (II), this invention preferably includes compounds of formula (IIb):

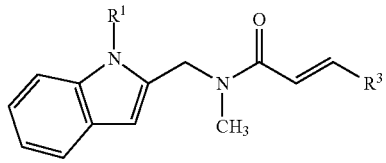

(IIb)

in which $R^3$ is as defined for formula (I) compounds.

Suitably, with respect to formula (I), $R^3$ is:

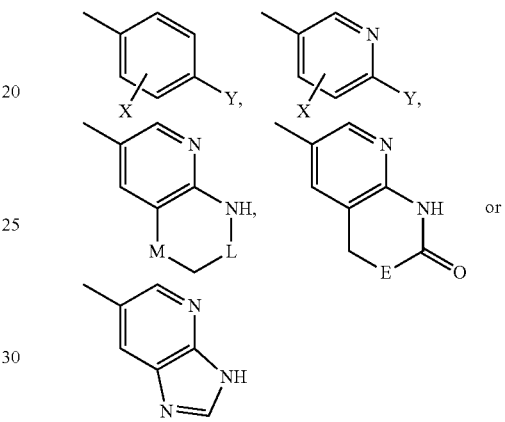

in which X, Y, M, L and E are as defined for formula (I) compounds.

Representative of the novel compounds of this invention are the compounds of examples 1-86 hereinafter. The compounds of this invention are Fab I inhibitors useful in the treatment of bacterial infections. Two compounds of this invention, namely (E)-N-methyl-N-(1-methyl-1H-indol-3-ylmethyl)-3-(7-oxo-5,6,7,8-tetrahydro-1,8-naphthyridin-3-yl)acrylamide and (EN-methyl-N-(2-methyl-1H-indol-3-yl-methyl)-3-(7-oxo-5,6,7,8-tetrahydro-1,8-naphthyridin-3-yl) acrylamide, are dual Fab I/Fab K inhibitors. These compounds have the potential to be broad spectrum antibiotics.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl isobutyl and t-butyl. $C_{1-4}$alkyl additionally includes pentyl, n-pentyl, isopentyl, neopentyl and hexyl and the simple aliphatic isomers thereof. $C_{0-6}$alkyl and $C_{0-6}$alkyl additionally indicates that no alkyl group need be present (e.g., that a covalent bond is present).

Any $C_{1-4}$alkyl or $C_{1-6}$ alkyl may be optionally substituted with the group Rx, which may be on any carbon atom that results in a stable structure and is available by conventional synthetic techniques. Suitable groups for $R^x$ are $C_{1-4}$alkyl, OR', SR', CN, N(R')$_2$, CH$_2$N(R')$_2$, —NO$_2$, —CF$_3$, —CO$_2$R'—CON(R')$_2$, —COR', —NR'C(O)R', F, Cl, Br, I, or —S(O)$_r$CF$_3$, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyl, tetrahydropyridinyl, pyridinyl, thiazolyl, thienyl quinolinyl, isoquinolinyl, and tetra- and perhydro-quinolinyl and isoquinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, FCC refers to pyridinium chlorochromate.

Generally, compounds of this invention are prepared by:

(i) reacting a compound of formula (III) with a compound of formula (IV):

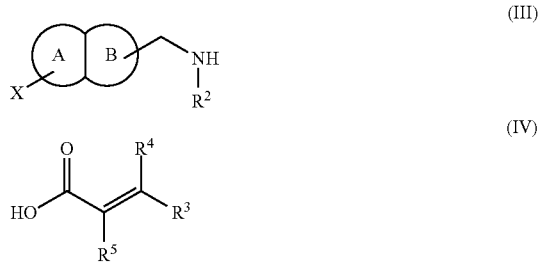

wherein $R^2$, $R^3$, $R^4$, $R^5$ and X are as defined in formula (I), with any reactive functional groups protected, in the presence of EDC and HOBT;

(ii) reacting a compound of formula (V) with a compound of formula (VI):

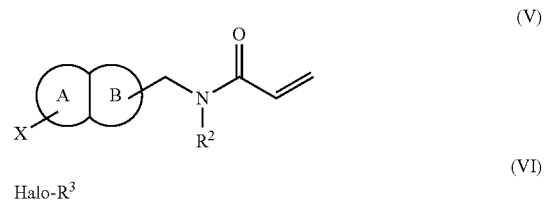

wherein $R^2$, $R^3$ and X are as defined in formula (I) and Halo is Br, Cl, F or I, with any reactive functional groups protected, in the presence of a palladium (H) salt, a phosphine ligand and base;

and thereafter removing any protecting groups, and optionally forming a pharmaceutically acceptable salt.

In particular, compounds of the formula (I) are prepared by the general methods described in the Schemes hereinafter.

Scheme I

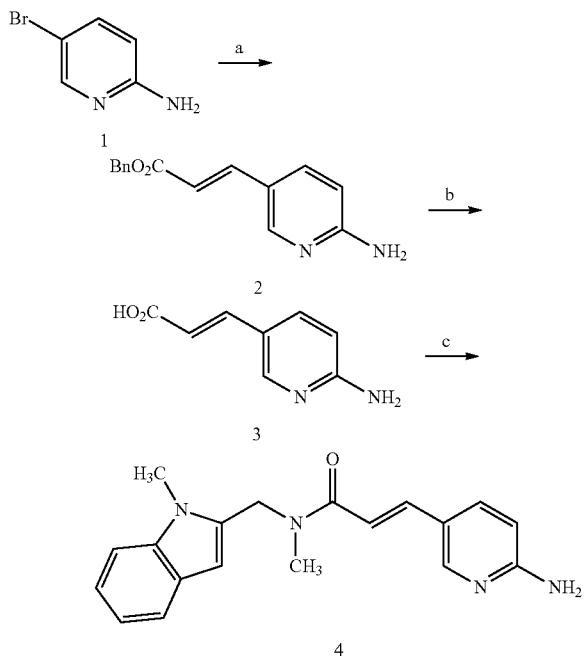

(a) benzyl acrylate, Pd(OAc)$_2$, P(o-tol)$_3$, (i-Pr)$_2$NEt, propionitrile;
(b) 1.0 N NaOH, MeOH; (c) 1-methyl-2-(methylaminomethyl)indole, EDC, HOBt•H$_2$O, Et$_3$N, DMF.

A suitable haloaromatic derivative, for instance for instance 2-amino-5-bromopyridine (I-1), reacts with an appropriate α,β-unsaturated ester, for example benzyl acrylate, in a Heck-type reaction (see Heck, *Org. Reactions* 1982, 27, 345) to afford I-2. The reaction is mediated by a palladium (0) species, and generally is conducted in an inert solvent, such as CH$_3$CN, propionitrile, or toluene, in the presence of an appropriate acid scavenger, such as triethylamine (Et$_3$N) or diisopropylethylamine ((i-Pr)$_2$NEt). Typical sources of the palladium(0) species include palladium (II) acetate (Pd (OAc)$_2$ and palladium(II) chloride (PdCl$_2$), and oftentimes phosphine ligands, for instance triphenylphosphine (PPh$_3$) or tri-ortho-tolylphosphine (P(tol)$_3$), are included. The ethyl ester of I-2 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-3. The carboxylic acid of I-3 is converted to an activated form using, for example, EDC and HOBt, or $SOCl_2$, and the activated form is subsequently reacted with an appropriate amine, for instance 1-methyl-2-(methylaminomethyl) indole, in a suitable solvent such as DMF, $CH_2Cl_2$, or $CH_3CN$, to afford I-4. Depending on whether acid neutralization is required, an added base, such as triethylamine ($Et_3N$), diisopropylethylamine ((i-Pr)$_2$NEt), or pyridine, may be used, Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag), which are incorporated herein by reference.

Amide coupling reagents as used herein denote reagents which may be used to form peptide bonds. Typical coupling methods employ carbodiimides, activated anhydrides and esters and acyl halides. Reagents such as EDC, DCC, DPPA. PPA, BOP reagent, HOBt, N-hydroxysuccinimide and oxalyl chloride are typical.

Typically, the amine is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine, optionally in the presence of a base, are also suitable. For example, a benzoic acid is treated in an anhydrous solvent, such as methylene chloride or tetrahydrofuran (THF), in the presence of a base, such as N-methylmorpholine, DMAP or a trialkylamine, with isobutyl chloroformate to form the "activated anhydride", which is subsequently reacted with the free amine.

Scheme II

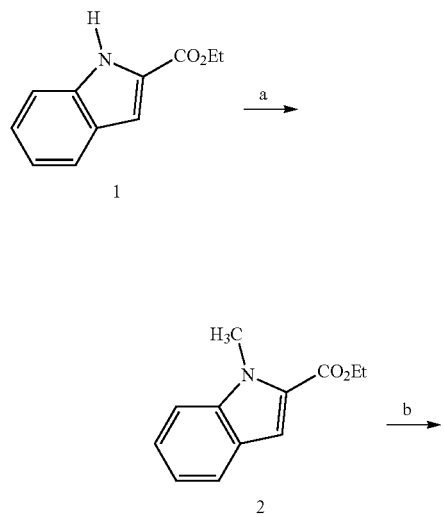

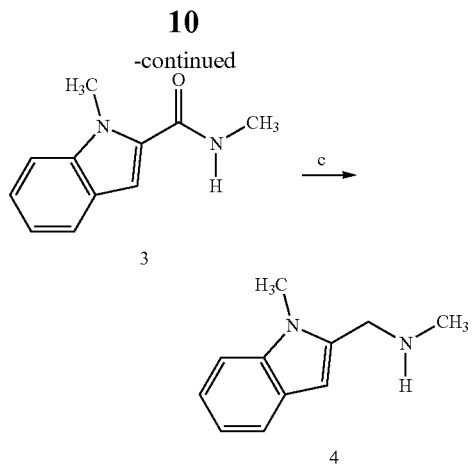

(a) NaH, MeI, DMF; (b) $CH_3NH_2$, $H_2O$, MeOH; (c) $LiAlH_4$, THF.

The amine coupling partners used in the present invention were prepared by established methods well-known to those of skill in the art. For example, amine II-4 is prepared by the straightforward procedure outlined in Scheme II. Commercially available ethyl indole-2-carboxylate (II-1) is deprotonated with a suitable base, generally sodium hydride (NaH), and the intermediate sodium salt is reacted with an appropriate alkylating agent, for instance methyl iodide, to afford II-2. Polar solvents such as DMF, THF, or mixtures thereof are generally preferred for this reaction. Compound II-2 can be conveniently converted to II-3 by reaction with an excess of an amine, such as methylamine, in a polar solvent, generally $H_2O$ or a mixture of $H_2O$ and methanol. Alternatively, the ester of II-2 can be saponified under standard conditions, typically with an alkali metal hydroxide such as LiOH, NaOH, or KOH, in an aqueous solvent, such as THF, ethanol, or methanol, and the resulting carboxylic acid can be converted to the desired amide. Typical methods for forming amides are described in Scheme I. Reduction of the amide II-3 to the amine II-4 is typically accomplished with lithium aluminum hydride ($LiAlH_4$) in refluxing THF, although many other methods can be used to reduce amides to amines. Such methods are well-known to those of skill in the art, and can be found in standard reference volumes, such as "Compendium of Organic Synthetic Methods" (published by Wiley-Interscience).

Scheme III

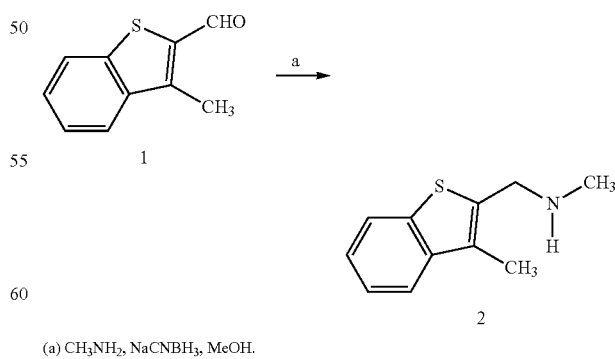

(a) $CH_3NH_2$, $NaCNBH_3$, MeOH.

The amine coupling partners used in the present invention can also be prepared by the reductive amination of an appropriate aldehyde (Scheme III). This method, which is well-known to those of skill in the art, involves the initial conversion of an aldehyde to an intermediate imine, which is subsequently reduced, oftentimes in situ, to afford the amine. For example, the commercially-available aldehyde III-1 reacts with an appropriate amine, for instance methylamine, to afford an intermediate imine (not shown), which is reduced in situ to amine III-2 by reaction with a suitable reducing agent, usually sodium cyanoborohydride or sodium (triacetoxy)borohydride. Frequently, the reaction is conducted in the presence of an acid, such as acetic acid, in a polar solvent such as methanol or DMF.

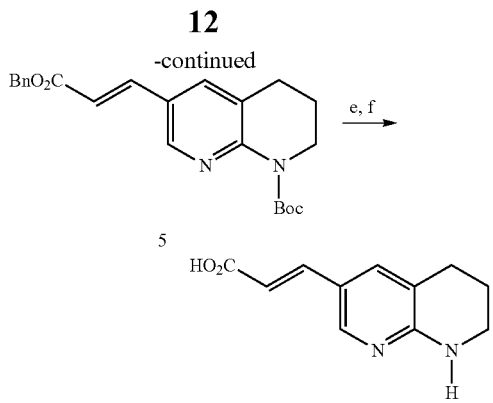

(a) H₂, Pd/C, EtOH; (b) (Boc)₂O, LiHMDS, THF; (c) NBS, AcOH, CH₂Cl₂; (d) benzyl acrylate, Pd(OAc)₂, P(o-tol)₃, (i-Pr)₂NEt, propionitrile; (e) 4 N HCl/dioxane; (f) LiOH, H₂O, MeOH.

1,8-Naphthyridine (V-1) can be selectively reduced to 1,2,3,4-tetrahydro-1,8-naphthyridine (V-2) by reaction with hydrogen gas in the presence of a suitable catalyst, preferably palladium metal on activated carbon (Pd/C), in an inert solvent, generally MeOH, EtOH, EtOAc, or mixtures thereof. V-2 is converted to a suitably protected derivative, for instance the N-Boc protected derivative V-3, by reaction with di-tert-butyl dicarbonate in the presence of an appropriate base, preferably lithium hexamethyldisilazide (LiHMDS). The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). V-3 is selectively brominated at the 6-position by reaction with a suitable brominating agent, such as bromine (Br₂ or N-bromosuccinimide (NBS). Typical solvents for a bromination reaction include CH₂Cl₂, CCl₄, MeOH, AcOH, or mixtures thereof. The resulting 6-bromo-1,2,3,4-tetrahydro-1,8-naphthyridine V-4 participates in a Heck reaction as described in Scheme I to afford V-5. Removal of the Boc protecting group is accomplished under standard acidic conditions well-known to those of skill in the art (see Greene above), and the benzyl ester is saponified as described in Scheme I to afford V-6.

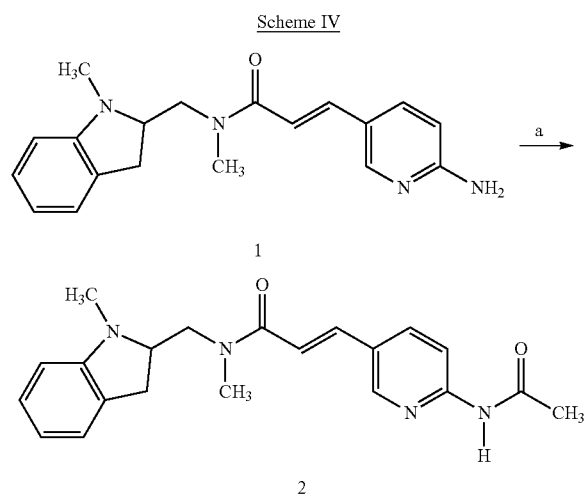

(a) Ac₂O, NaHCO₃, THF.

The amine of compound IV-1 (prepared as described in Scheme I) reacts with a variety of acylating agents to produce amides, sulfonamides, ureas, and carbamates. For example, IV-1 reacts with acetic anhydride (Ac₂O) in a neutral solvent, typically THF, in the presence of a suitable base, such as sodium bicarbonate (NaHCO₃), to afford IV-2. Other acylating agents, including sulfonyl halides, isocyanates, and chlorocarbonates, also participate in this reaction to afford sulfonamides, ureas, and carbamates, respectively.

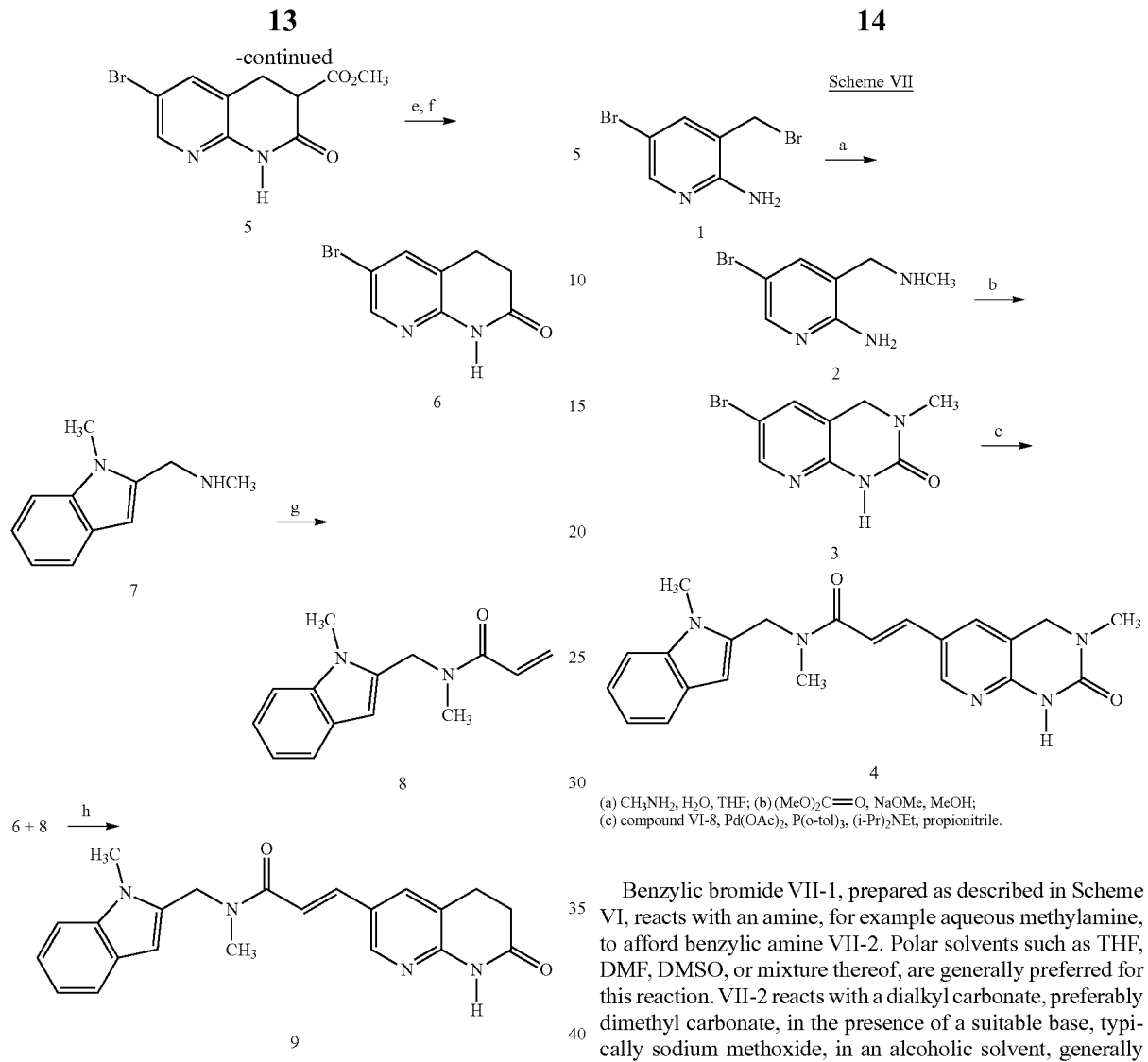

(a) LiAlH₄, THF; (b) NBS, CH₂Cl₂; (c) 48% HBr; (d) (MeO₂C)₂CH₂, NaOMe, MeOH; (e) NaOH, H₂O, MeOH; (f) HCl, H₂O, MeOH; (g) acryloyl chloride, Et₃N, CH₂Cl₂; (h) Pd(OAc)₂, P(o-tol)₃, (i-Pr)₂NEt, propionitrile.

Commercially available 2-aminonicotinic acid (VI-1) is reduced to alcohol VI-2 under standard conditions (LiAlH₄, THF), and the aromatic ring of VI-2 is brominated using, for example, bromine or N-bromosuccinimide (NBS), in a neutral solvent such as CH₂Cl₂, to afford VI-3. On reaction with 48% aqueous HBr, VI-3 is converted to bromide VI-4, which reacts with a diester of malonic acid, for instance dimethyl malonate, in the presence of a suitable base, typically sodium methoxide, in an alcoholic solvent such as methanol, to afford the naphthyridone derivative VI-5. Saponification and neutralization under standard conditions affords an intermediate carboxylic acid (not shown), which is typically not isolated, but is subject to decarboxylation on gentle warming to afford the naphthyridone VI-6. This compound reacts with acrylamide VI-8 in a Heck-type reaction as described in Scheme I to afford VI-9. Alternatively, VI-6 might be converted to VI-9 according to the general procedure described in Scheme I for the conversion of I-1 to I-4. The acrylamide VI-8 is conveniently prepared by reaction of amine VI-7 (see Scheme II) with an activated form of acrylic acid in an amide bond-forming reaction. Typical conditions for the formation of amides are described in Scheme I, and are well-known to those of skill in the art.

(a) CH₃NH₂, H₂O, THF; (b) (MeO)₂C═O, NaOMe, MeOH; (c) compound VI-8, Pd(OAc)₂, P(o-tol)₃, (i-Pr)₂NEt, propionitrile.

Benzylic bromide VII-1, prepared as described in Scheme VI, reacts with an amine, for example aqueous methylamine, to afford benzylic amine VII-2. Polar solvents such as THF, DMF, DMSO, or mixture thereof, are generally preferred for this reaction. VII-2 reacts with a dialkyl carbonate, preferably dimethyl carbonate, in the presence of a suitable base, typically sodium methoxide, in an alcoholic solvent, generally methanol, to afford the cyclic urea derivative VII-3. This compound is converted to VII-4 by reaction with compound VI-8 as described in Scheme VI.

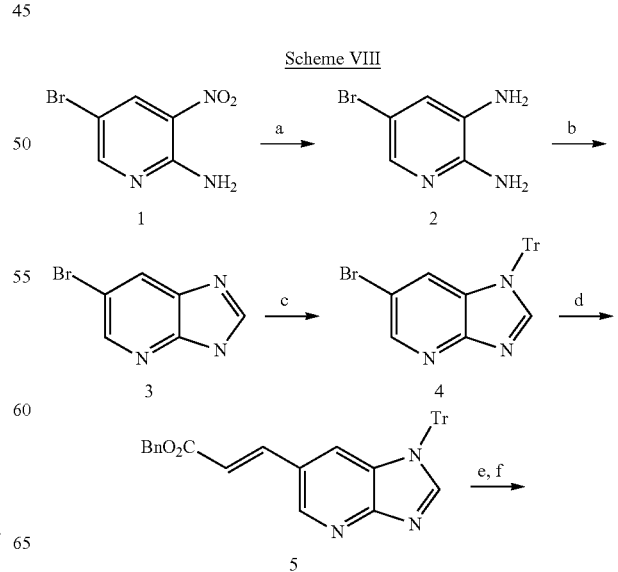

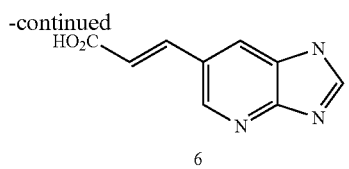

6

(a) SnCl₂•H₂O, EtOH; (b) 96% HCO₂H; (c) TrCl, Et₃N, CH₂Cl₂; (d) benzyl acrylate, Pd(OAc)₂, P(o-tol)₃, (i-Pr)₂NEt, propionitrile; (e) 4 N HCl/dioxane; (f) NaOH, H₂O, MeOH.

The nitro group of commercially available 2-amino-5-bromo-3-nitropyridine (VIII-1) is reduced under standard conditions using, for example, tin (II) chloride in EtOH. The resulting diamine. VIII-2, reacts with formic acid, or an appropriate equivalent, to afford the imidazopyridine derivative VIII-3. This compound is converted to a suitably protected derivative, for instance the N-trityl protected derivative VIII-4, by reaction with trityl chloride in the presence of an appropriate base, typically triethylamine or diisopropylethylamine. Typical solvents for this reaction include CH₂Cl₂, DMF, or mixtures thereof. As discussed in Scheme V, the protecting group for the amine must be compatible with the subsequent chemistry, and must be readily removable when desired. VIII-4 is converted to VIII-6 according to the general procedure described in Scheme V.

Scheme IX

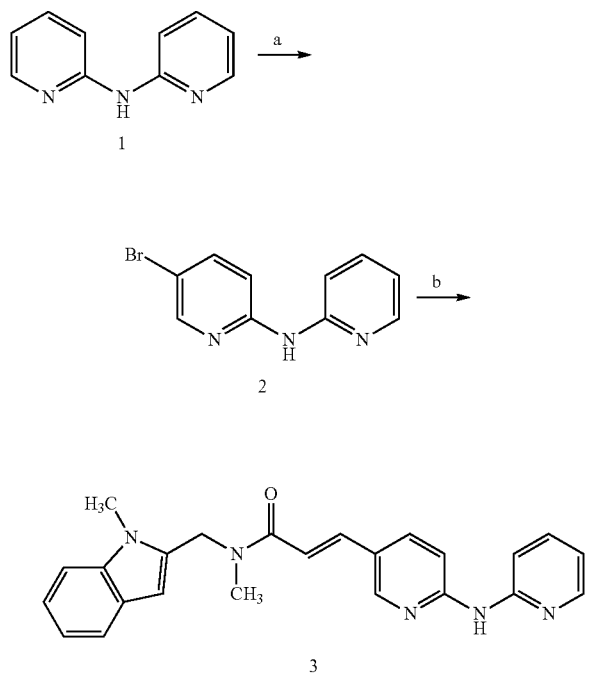

(a) Br₂, AcOH; (b) N-methyl-N-(1-methyl-1H-indol-2-ylmethyl)acrylamide, Pd(OAc)₂, P(o-tol)₃, (i-Pr)₂NEt, propionitrile.

Commercially-available 2,2'-dipyridylamine (IX-1) is monobrominated at the 5-position by reaction with a suitable brominating agent, such as bromine (Br₂) or N-bromosuccinimide (NBS). Typical solvents for a bromination reaction include CH₂Cl₂. CCl₄, MeOH, AcOH, or mixtures thereof. The resulting mono-bromo derivative IX-2 reacts with N-methyl-N-(1-methyl-1H-indol-2-ylmethyl)acrylamide in a Heck-type reaction as described in Scheme I to afford EX-3.

Scheme X

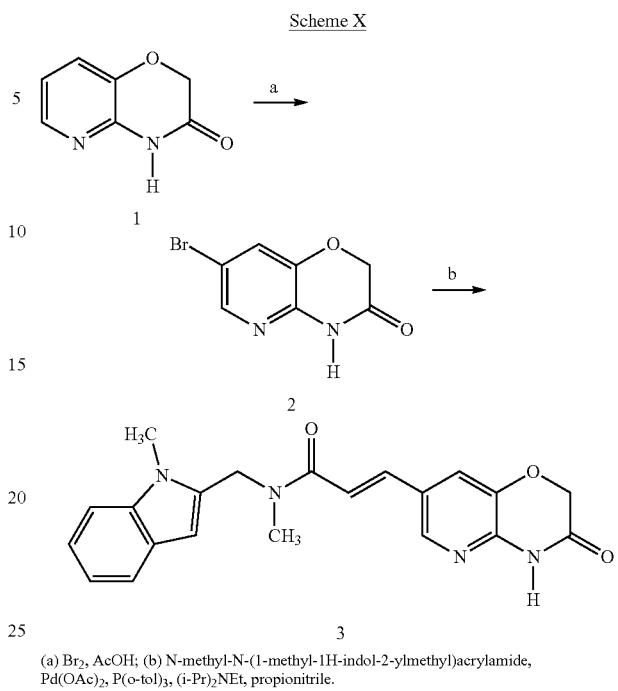

(a) Br₂, AcOH; (b) N-methyl-N-(1-methyl-1H-indol-2-ylmethyl)acrylamide, Pd(OAc)₂, P(o-tol)₃, (i-Pr)₂NEt, propionitrile.

Commercially-available 2H-pyrido[3,2-b]-1,4-oxazin-3(4H)-one (X-1) is selectively brominated at the 5-position by reaction with a suitable brominating agent, such as bromine (Br₂) or N-bromosuccinimide (NBS). Typical solvents for a bromination reaction include CH₂Cl₂, CCl₄, MeOH, AcOH, or mixtures thereof. The resulting mono-bromo derivative X-2 reacts with N-methyl-N-(1-methyl-1H-indol-2-ylmethyl)acrylamide in a Heck-type reaction as described in Scheme I to afford X-3.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li⁺, Na⁺, K⁺, Ca⁺⁺, Mg⁺⁺ and NH₄⁺ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of Fab I and are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, dacryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.
Cloning of S. aureus FabI:

The fabI gene was cloned from the chromosomal DNA of S. aureus strain WCUH29 using the polymerase chain reaction. Amplification was performed using Taq DNA polymerase (BRL) and the following primers: 5'-CGCCTC-GAGATGTTAAATCTTGAAAACAAAACATATGTC-3' (SEQ ID NO: 1) and 5'-CGCGGATCCAATCAAGTCAG-GTTGAAATATCCA-3' (SEQ ID NO: 2) (XhoI and BamHI sites underlined). The resulting fragment was then digested with XhoI and BamHI and ligated into XhoI- and BamHI-digested expression vector pET-16b (Novagen), producing pET-His$_{10}$-fabI. The gene sequence of fabI was confirmed by automated cycle sequencing using an Applied Biosystems model 377 machine. The untagged version of pET fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCTTGAAAA-CAAAACA-3' (SEQ ID NO: 3) and 5'-TAT-GTTTTGTTTTCAAGATTTAAGCC-3' (SEQ ID NO: 4). The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.
Purification of S. aureus FabI S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.
Cloning of E. coli FabI:

A PCR fragment of correct size for E. coli FabI was PCR amplified from E. coli chromosomal DNA, subcloned into the TOPO TA cloning vector, and verified by colony PCR+restriction endonuclease analysis. The presumptive E. coli FabI PCR fragment was subcloned into the expression vector pBluePet. The FabI clone was transformed into E. coli strain BL21(DE3). Small Scale expression studies show an overexpressed protein band of correct molecular weight (~28 Kda) for E coli FabI clearly visible following Coomassie staining of SDS PAGE gels. DNA sequencing of the E coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S. aureus FabI Enzyme Inhibition Assay (NADFH):

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors were typically varied over the range of 0.01-10 uM. The consumption of NADH was monitored for 20 minutes at 30° C. by following the change in absorbance at 340 nm. Initial velocities were estimated from an exponential Tit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 5.0 micromolar to about 0.05 micromolar.

S. aureus FabI Enzyme Inhibition Assay (NADPH):

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors were typically varied over the range of 0.01-10 uM. The consumption of NADPH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

E. coli FabI Enzyme Inhibition Assay:

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01-10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 100.0 micromolar to about 0.05 micromolar.

Preparation and Purification of Crotonoyl-ACP:

Reactions contained 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 75. The mixture was gently mixed on a magnetic stirrer at 23° C. for 2 hr, and the reaction was terminated by the addition of 15 mM EDTA. The reaction mixture was filtered through a 0.2 micron filter (Millipore) and applied to a MonoQ column (Pharmacia) equilibrated with 20 mM Tris-Cl, pH 7.5. The column was washed with buffer until all non-adherent material was removed (as observed by UV detection), and the crotonoyl-ACP was eluted with a linear gradient of 0 to 400 mM NaCl.

S. aureus FabI Enzyme Inhibition Assay Using Crotonoyl-ACP:

Assays are carried out in half-area, 96-well microtitre plates. Compounds are evaluated in 150 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of S. aureus Fab I (approximately 20 nM). Inhibitors are typically varied over the range of 0.01-10 uM. The consumption of NADPH is monitored for 20 minutes at 30° C. by following the change in absorbance at 340 nm. Initial velocities are estimated from a linear fit of the progress curves. $IC_{50}$'s are estimated from a fit of the initial velocities to a standard, 4-parameter model (Equation 1) and are typically reported as the mean±S.D. of duplicate determinations. Compounds of this invention in this assay have $IC_{50}$'s from about 100.0 micromolar to about 0.04 micromolar. The apparent Ki is calculated from Equation 2 assuming the inhibition is competitve with crotonoyl-ACP.

$$v=\text{Range}/(1[I]/IC50)s+\text{Background} \qquad \text{Equation 1}$$

$$Ki(\text{app})=IC50/(1+[S]/Ks) \qquad \text{Equation 2}$$

FabK Enzyme Inhibition Assay

FabK catalyses the reduction of enoyl-ACPs with the concomitant oxidation of NADH. The reduction of crotonoyl-ACP to butyryl-ACP can be monitored by following the change in absorbance at 340 nm as NADH is oxidized.

Assays were carried out in Costar 3696 half-area plates in a final assay volume of 150 uL on a Spectramax platereader. The substrates (NADH and crotonoyl-ACP) were incubated with FabK enzyme in 100 mM N-[2-acetamido]-2 iminodiacetic acid (ADA), pH 6.5, 100 mM $NH_4Cl$, 4% glycerol at 30° C. and the reaction was monitored at 340 nm.

Using the above assay, compounds were tested for inhibition of FabK. 30 uL of inhibitor was added to a well of the plate. 30 uL of a 250 uM stock of NADH and 60 uL of a 67.5 uM stock of crotonoyl ACP were then added to the well. The plate was incubated at 30° C. for 5 min. The reaction was initiated by adding 30 uL of a 6.25 nM stock of enzyme to the well (also pre-incubated at 30° C.). The reaction was then monitored at A340 nm for 30 min at 30° C. Positive controls were reactions without compound. Negative controls were reactions without enzyme and without compound. Final concentrations in the assay mixture were 25 uM crotonoyl-ACP, 50 uM NADH, and 1.25 nM enzyme.

IC50s were determined for compounds by carrying out the assay at 8 different concentrations of compound (100 uM-0.75 uM) in duplicate. The IC50 was calculated using Grafit software (v 4.09). The two Fab K inhibitors of this invention have IC50's of about 5 micromolar.

Antimicrobial Activity Assay:

Whole-cell antimicrobial activity was determined by broth microdilution using the National Committee for Clinical Laboratory Standards (NCCLS) recommended procedure. Document M7-A4, "Methods for Dilution Susceptibility Tests for Bacteria that Grow Aerobically". The compound was tested in serial two-fold dilutions ranging from 0.06 to 64 mcg/mL. Test organisms were selected from the following laboratory strains: *Staphylococcus aureus* Oxford, *Staphylococcus aureus* WCUH29, *Streptococcus pneumoniae* ERY2, *Streptococcus pneumoniae* 1629, *Streptococcus pneumoniae* N1387, *Enterococcus faecalis* I, *Enterococcus faecalis* 7, *Haemophilus influenzae* QI, *Haemophilus influenzae* NEMC1, *Moraxella Catarrhalis* 1502, *Escherichia coli* 7623 AcrABEFD+, *Escherichia coli* 120AcrAB−, *Escherichia coli* MG1655, *Escherichia coli* MG1658. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 (µg/mL.

According to the instant invention, the preferred Fab I and Fab K enzyme inhibition assays use crotonoyl-ACP, rather than crotonoyl CoA, as a substrate. Thus, this invention comprises the preparation and purification of crotonoyl-ACP and the use of this purified enzyme in Fab I and Fab K enzyme inhibition assays. Crotonoyl-ACP was synthesised using *S. pneumoniae* ACP synthase to catalyse the addition of a crotonoyl group from crotonoyl CoA to *E. coli* apo-acyl carrier protein (ACP). In a further aspect of this invention, it is contemplated that an apo-acyl carrier protein from any bacterial species, such as from *Escherichia coli*, *Staphylococcus* and *Streptococcus*, can be used in the preparation of crotonoyl-ACP. This synthesis was carried out in the presence of magnesium chloride in NaHEPES, pH 7.5. The reaction was complete in 2 hours at a reaction temperature of about 20-30° C., preferably at 23° C.

The purified crotonoyl-ACP prepared above is then used in the Fab I and Fab K assays to determine the inhibitors of the instant invention. Assays may be carried out, for example, in Costar 3696 half-area plates, preferably at a final assay volume of 150 ul on a Spectramax platereader. Preferred substrates used in the methods of the invention are NADH, NADPH, an NADH analogue and crotonoyl-ACP. Further provided are preferred methods comprising the step of incubating substrates with Fab I or Fab K in 100 mM N-[2-acetamido]-2 iminodiacetic acid (ADA), pH 6.5. This reaction may be monitored at 340 nm, among other wavelengths.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at either 300 or 360 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiples dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Anal tech Silica Gel GF and E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 1-methyl-2-(methylaminomethyl)-1H-indole a) Ethyl 1-methyl-1H-indole-2-carboxylate NaH (60% dispersion in mineral oil. 8.02 g, 200.49 mmole) was washed with hexanes, then was suspended in dry DMF (530 mL). Solid ethyl indole-2-carboxylate (25.29 g, 133.66 mmole) was added portionwise over 5-10 min, allowing gas evolution to subside between additions. When the addition was complete, the yellow mixture was stirred for 15 min, then methyl iodide (42 mL, 668.3 mmole) was added all at once. The reaction was exothermic, and the internal temperature rose to 40-45° C. After 1 hr, the reaction was quenched with 10% NH$_4$Cl (100 mL) and concentrated on the rotavap (high vacuum). The residue was partitioned between Et$_2$O (500 mL) and H$_2$O (100 mL), and the layers were separated. The Et$_2$O layer was washed with H$_2$O (100 mL), dried (MgSO$_4$), and concentrated to leave the title compound (27.10 g, quantitative) as a light yellow solid. This was used without further purification: TLC (10% EtOAc/hexanes) Rf=0.39.

b) N,1-Dimethyl-1H-indole-2-carboxamide

A suspension of ethyl 1-methyl-1H-indole-2-carboxylate (27.10 g, 133.34 mmole) in 40% aqueous CH$_3$NH$_2$ (300 mL) and MeOH (30 mL) was stirred at RT. A solid tended to gradually creep up the walls of the flask, and was washed down periodically with MeOH. The flask was tightly stoppered to keep the material inside the flask. As the reaction proceeded, the solid dissolved, but eventually the product began to precipitate. The reaction was stirred at RT for 5 days, then was concentrated to remove approximately 200 mL of the solvent. The remaining residue was diluted with H$_2$O (300 mL), and the solid was collected by suction filtration and washed with H$_2$O. Drying at 50-60° C. in high vacuum left the title compound (23.45 g, 93%) as a faintly yellow solid: $^1$H NMR (300 MHz, CDCl$_3$) δ 7.63 (d, J=8.0 Hz, 1H), 7.27-7.43 (m, 2H), 7.10-7.20 (m, 1H), 6.80 (s, 1H), 6.10-6.30 (m, 1H), 4.06 (s, 3H), 3.01 (d, J=4.9 Hz, 3H).

c) 1-Methyl-2-(methylaminomethyl)-1H-indole

A 3-liter 3-necked roundbottom flask equipped with overhead stirring was charged with N,1-dimethyl-1H-indole-2- carboxamide (23.45 g, 124.58 mmole) and anhydrous THF (170 mL). The solution was stirred while a solution of LiAlH$_4$ in THF (1.0 M, 250 mL, 250 mmole) was added via syringe. Gas was evolved during the addition of the first 50 mL of LiAlH$_4$ solution. When the addition was complete, the resulting light yellow solution was heated at gentle reflux. After 23 hr, the reaction was cooled in ice and quenched by the sequential dropwise addition of H$_2$O (9.5 mL), 15% NaOH (9.5 mL), and H$_2$O (28.5 mL). The mixture was stirred for 15 min, then was filtered through Celite®, and the filter pad was washed thoroughly with THF. The filtrate was concentrated and the residue was flash chromatographed on silica gel (10% MeOH/CHCl$_3$ containing 0.5% conc. NH$_4$OH). The title compound (20.17 g, 93%) was obtained as a light yellow oil: $^1$H NMR (300 MHz, CDCl$_3$) δ 7.56 (d, J=7.8 Hz, 1H), 7.02-7.35 (m, 3H), 6.38 (s, 1H), 3.88 (s, 2H), 3.75 (s, 3H), 2.49 (s, 3H).

Preparation 2

Preparation of (E)-3-(6-aminopyridin-3-yl)acrylic acid (Method A)

a) Benzyl (E)-3-(6-aminopyridin-3-yl)acrylate

A solution of 2-amino-5-bromopyridine (2.25 g, 13.0 mmole), benzyl acrylate (3.2 g, 19.7 mmole), Pd(OAc)$_2$ (0.31 g, 1.4 mmole), tri-ortho-tolylphosphine (0.73 g, 2.4 mmole), and diisopropylethylamine (3.5 mL, 20.0 mmole) in propionitrile (50 mL) was heated at reflux overnight. The dark mixture was filtered through Celite®, and the filtrate was concentrated. Flash chromatography on silica gel (3% MeOH/CH$_2$Cl$_2$) gave the title compound (1.3 g, 39%): MS (ES) m/e 255 (M+H)$^+$.

b) (E)-3-(6-Aminopyridin-3-yl)acrylic acid

A solution of benzyl (E)-3-(6-aminopyridin-3-yl)acrylate (1.3 g, 5.1 mmole) and 1.0 N NaOH (10 mL, 10 mmole) in MeOH was heated at reflux overnight. The solution was concentrated in vacuo, and the residue was dissolved in H$_2$O. The pH was adjusted to 6 with dilute HCl, and the solid precipitate was collected by suction filtration and dried to give the title compound (0.6 g, 72%) as a white solid: MS (ES) m/e 165 (M+H)$^+$.

Preparation 3

Preparation of (E)-3-(6-aminopyridin-3-yl)acrylic acid (Method B)

a) (E)-3-(6-Aminopyridin-3-yl)acrylic acid

Acrylic acid (23 mL, 0.33 mole) was added carefully to a solution of 2-amino-5-bromopyridine (25.92 g, 0.15 mole) and Na$_2$CO$_3$ (55.64 g, 0.53 mole) in H$_2$O (600 mL). PdCl$_2$ (0.53 g, 0.003 mole) was then added, and the mixture was heated at reflux. After 24 hr, the reaction was cooled to RT and filtered, and the filtrate was adjusted to pH 6 with aqueous HCl. Additional H$_2$O (0.5 L) was added to improve mixing, and the mixture was stirred for 1 hr. The pH was readjusted to 6, then the solid was collected by suction filtration. The filter pad was washed sequentially with H$_2$O (2×0.5 L), cold absolute EtOH (100 mL), and Et$_2$O (2×250 mL). Drying in high vacuum at elevated temperature gave the title compound (15.38 g, 62%) as a tan solid: 1H NMR (300 MHz, DMSO-d$_6$) δ 8.11 (d, J=2.0 Hz, 1H), 7.75 (dd, J=8.7, 2.0 Hz, 1H), 7.43 (d, J=15.8 Hz, 1H), 6.53 (s, 2H), 6.45 (d, J=8.7 Hz, 1H), 6.22 (d, J=15.8 Hz, 1H); MS (ES) m/e 165 (M+H)$^+$.

Preparation 4

Preparation of 1-methyl-3-(methylaminomethyl)-1H-indazole a) Methyl (1-methyl-1H-indazole)carboxylate Indazole-3-carboxylic acid (5.0 g, 30 mmole), K$_2$CO$_3$ (12.4 g, 90 mmole), and MeI (9.3 mL, 150 mmole) were combined in dry DMF (100 mL) and heated to 50° C. After 18 hr the mixture was cooled to RT and concentrated in vacuo. The residue was taken up in EtOAc and filtered, and the filtrate was concentrated under reduced pressure. The residue was chromatographed on silica gel (25% EtOAc/hexanes) to give the title compound (3.88 g, 68%) as a yellow solid: $^1$H NMR (300 MHz, CDCl$_3$) δ 8.24 (m, 1H), 7.47 (m, 2H), 7.34 (m, 1H), 4.19 (s, 3H), 4.05 (s, 3H).

b) N,1-Dimethyl-1H-indazole-3-carboxamide

A suspension of methyl (1-methyl-1H-indazole)carboxylate (3.88 g, 20.4 mmole) in 40% aqueous CH$_3$NH$_2$ (100 mL) and MeOH (5 mL) was stirred at RT for 4 hr. During that time the suspension became a solution. The mixture was concentrated to approximately ⅓ by volume at which time the product precipitated as a pale yellow solid. The solid was collected by filtration, washed with H$_2$O, and dried in vacuo to give the title compound (3.42 g, 89%) which was sufficiently pure for use in the next step: $^1$H NMR (300 MHz, CDCl$_3$) δ 8.24 (m, 1H), 7.47 (m, 2H), 7.34 (m, 1H), 6.95 (bs, 1H), 4.19 (s, 3H), 3.05 (d, J=12.0 Hz, 3H).

c) 1-Methyl-3-(methylaminomethyl)-1H-indazole

To a solution of N,1-dimethyl-1H-indazole-3-carboxamide (3.42 g, 18 mmole) in dry THF (90 mL) was added a solution of LiAlH$_4$ in THF (1.0 M, 36 mL, 36 mmole) slowly at RT. After 2 hr the mixture was heated to a gentle reflux. After 4 hr the mixture was cooled to RT and quenched by dropwise addition of 2.0 M NaOH until a white solid had formed. The mixture was dried (MgSO$_4$), filtered, and concentrated under reduced pressure to give the title compound (3.28 g, 100%) as an oil which was sufficiently pure for use in the next step: MS (ES) m/e 176 (M+H)$^+$.

Preparation 5

Preparation of (E)-3-(3,4-dihydro)-2H-pyrido[3,2-b]-1,4-oxazin-7-yl)acrylic acid a) 3,4-Dihydro-2H-pyrido[3,2-b]-1,4-oxazine To a suspension of 2H-pyrido[3,2-b]-1,4-oxazin-3(4H)-one (2.0 g, 13.3 mmole) in dry THF (40 mL) was added a solution of LiAlH$_4$ in THF (1.0 M, 26.6 mL, 26.6 mmole) slowly at 0° C. After 1 hr the mixture was quenched with 2.0 M NaOH until a solid formed. The mixture was dried (MgSO$_4$), filtered, and concentrated under reduced pressure to give the title compound (1.44 g, 79%) as a white solid which was sufficiently pure for use in the next step: MS (ES) m/e 137 (M+H)$^+$.

b) 4-(tert-Butoxycarbonyl)-3,4-dihydro-2H-pyrido[3,2-b]-1,4-oxazine

To a solution of 3,4-dihydro-2H-pyrido[3,2-b]-1,4-oxazine (1.44 g, 10.6 mmole) and di-tert-butyl dicarbonate (2.78 g, 12.7 mmole) in dry THF (50 mL) was added a solution of LiHMDS in THF (1.0 M, 12.7 mL, 12.7 mmole) dropwise at 0° C. After 30 rain the mixture was quenched with saturated $NH_4Cl$ and extracted with EtOAc (3×). The combined organic layers were dried ($MgSO_4$), filtered, and concentrated. Flash chromatography on silica gel (40% EtOAc/hexanes) gave the title compound (2.0 g, 80%) as a clear oil: MS (ES) m/e 237 $(M+H)^+$.

c) 4-(tert-Butoxycarbonyl)-7-bromo-3,4-dihydro-2H-pyrido[3,2-b]-1,4-oxazine

To a solution of 4-(tert-butoxycarbonyl)-3,4-dihydro-2H-pyrido[3,2-b]-1,4-oxazine (2.0 g, 8.46 mmole) in MeOH (40 mL) was added $Br_2$ (053 mL, 10.2 mmole) dropwise at 0° C. After 1 hr the mixture was concentrated. The residue was taken up in 1:1 $Et_2O$/hexanes and filtered. The filtrate was concentrated under reduced pressure to give the title compound (1.27 g, 48%) as an oil which solidified under vacuum: $^1H$ NMR (400 MHz, $CDCl_3$) δ 8.10 (s, 1H), 7.33 (s, 1H), 4.25 (m, 2H), 3.92 (m, 2H), 1.54 (s, 9H).

d) (E)-3-[4-(tert-Butoxycarbonyl)-3,4-dihydro-2H-pyrido[3,2-b]-1,4-oxazin-7-yl]acrylic acid A solution of 4-(tert-butoxycarbonyl)-7-bromo-3,4-dihydro-2H-pyrido[3,2-b]-1,4-oxazine (1.27 g, 4.03 mmole), benzyl acrylate (785 mg, 4.84 mmole), $Pd(OAc)_2$ (45 mg, 0.20 mmole), P(o-tolyl)$_3$ (122 mg, 0.4 mmole), and (i-Pr)$_2$NEt (1.76 mL, 10.1 mmole) in propionitrile (20 mL) was degassed (3×$N_2$/vacuum) then heated to reflux. After 18 hr the mixture was cooled to RT and concentrated. Flash chromatography on silica gel (25% EtOAc/hexanes) gave the title compound (1.17 g, 73%) as a yellow oil: MS (ES) m/e 397 $(M+H)^+$.

e) (E)-3-(3,4-dihydro-2H-pyrido[3,2-b][1,4]oxazin-7-yl)acrylic acid (E)-3-[4-(tert-Butoxycarbonyl)-3,4-dihydro-2H-pyrido[3,2-b]-1,4-oxazin-7-yl]acrylic acid (1.17 g, 2.95 mmole) was dissolved in 4 N HCl in dioxane (15 mL). After 72 hr the mixture was concentrated. The residue was taken up in 1:1 MeOH/$H_2$ (20 mL). 1.0 N LiOH (15 mL, 15 mmole) was added and the mixture was heated to reflux. After 18 hr the mixture was cooled to RT and concentrated to approximately ⅓ volume. The mixture was adjusted to pH 6 using 10% HCl. The solid was collected by filtration, washed with $H_2O$ and dried in vacuo to give the title compound (315 mg, 52% over 2 steps): MS (ES) m/e 207 $(M+H)^+$.

Preparation 6

Preparation of (E)-3-(5,6,7,8-tetrahydro-1,8-naphthyridin-3-yl)acrylic acid a) 1,2,3,4-Tetrahydro-1,8-naphthyridine 1,8-Naphthyridine (1.0 g, 7.68 mmole) was hydrogenated (50 psi) with 10% Pd/C (100 mg) in absolute ethanol (40 mL) for 18 hr. The mixture was filtered through a pad of Celite® and the filtrate was concentrated to give the title compound (1.04 g) which was sufficiently pure for use in the next step: MS (ES) m/e 135 $(M+H)^+$.

b) 1-(tert-Butoxycarbonyl)-1,2,3,4-tetrahydro-1,8-naphthyridine

To a solution of 1,2,3,4-tetrahydro-1,8-naphthyridine (1.04 g, 7.68 mmole) and di-tert-butyl dicarbonate (2.01 g, 9.22 mmole) in dry THF (40 mL) was added a solution of LiHMDS in THF (1.0 M, 9.22 mL, 9.22 mmole) dropwise at 0° C. After 30 min the mixture was quenched with saturated $NH_4Cl$ and extracted with EtOAc (3×). The combined organic layers were dried ($MgSO_4$), filtered, and concentrated. Flash chromatography on silica gel (40% EtOAc/hexanes) gave the title compound (1.37 g, 76% over 2 steps) as an orange oil which solidified under vacuum: $^1H$ NMR (400 MHz, $CDCl_3$) δ 8.33 (m, 1H), 7.37 (m, 1H), 6.94 (m, 1H), 3.77 (m, 2H), 2.75 (t, J=6.5 Hz, 2H), 1.93 (m, 2H), 1.54 (s, 9H).

c) 1-(tert-Butoxycarbonyl)-6-bromo-1,2,3,4-tetrahydro-1,8-naphthyridine

To a solution of 1-(tert-butoxycarbonyl)-1,2,3,4-tetrahydro-1,8-naphthyridine (1.37 g, 5.85 mmole) in $CH_2Cl_2$ (30 mL) was added glacial HOAc (3.4 mL, 58.5 mmole) and NBS (1.09 g, 6.14 mmole). After 72 hr the mixture was washed with 2.0 M NaOH, $H_2O$, and brine. The mixture was dried ($MgSO_4$), filtered, and concentrated under reduced pressure to give the title compound (1.79 g, 98%) which was sufficiently pure for use in the next step: $^1H$ NMR (400 MHz, $CDCl_3$) δ 835 (s, 1H), 7.51 (s, 1H), 3.77 (m, 2H), 2.75 (t, J=6.5 Hz, 2H), 1.93 (m, 2H), 1.54 (s, 9H).

d) Benzyl (E)-3-[8-(tert-butoxycarbonyl)-5,6,7,8-tetrahydro-1,8-naphthyridin-3-yl]acrylate A solution of 1-(tert-butoxycarbonyl)-6-bromo-1,2,3,4-tetrahydro-1,8-naphthyridine (1.79 g, 5.70 mmole), benzyl acrylate (1.11 g, 6.84 mmole), $Pd(OAc)_2$ (65 mg, 0.29 mmole), P(o-tolyl)$_3$ (173 mg, 0.57 mmole), and (i-Pr)$_2$NEt (2.5 mL, 14.25 mmole) in propionitrile (30 mL) was degassed (3×$N_2$/vacuum) then heated to reflux. After 18 hr the mixture was cooled to RT and concentrated. Flash chromatography on silica gel (25% EtOAc/hexanes) gave the title compound (1.21 g, 54%) as a yellow solid: $^1H$ NMR (400 MHz, $CDCl_3$) δ 8.44 (s, 1H), 7.65 (d, J=16.0 Hz, 1H), 7.53 (s, 1H), 7.40 (m, 5H), 6.43 (d, J=16.0 Hz, 1H), 5.25 (s, 2H), 3.77 (m, 2H), 2.75 (t, J=63 Hz, 2H), 1.93 (m, 2H), 1.54 (s, 9H)

e) (E)-3-(5,6,7,8-tetrahydro-1,8-naphthyridin-3-yl)acrylic acid

Benzyl (E)-3-[8-(tert-butoxycarbonyl)-5,6,7,8-tetrahydro-1,8-naphthyridin-3-yl]acrylate (1.21 g, 3.07 mmole) was dissolved in 4 N HCl in dioxane (15 mL). After 18 hr the mixture was concentrated. The residue was taken up in 1:1 MeOH/$H_2O$ (15 mL). 1.0 N LiOH (15 mL, 15 mmole) was added and the mixture heated to reflux. After 18 hr the mixture was cooled to RT and concentrated to approximately ⅓ volume. The mixture was adjusted to pH 6 using 10% HCl. The solid was collected by filtration, washed with $H_2O$, and dried in vacuo to give the title compound (180 mg, 29% over 2 steps): MS (ES) m/e 205 $(M+H)^+$.

Preparation 7

Preparation of 2-(methylaminomethyl)thieno[2,3-b]thiophene a) 3-(1,3-Dioxolan-2-yl)thiophene To a solution of thiophene-3-carboxaldehyde (5.0 g, 44.58 mmole) in benzene (200 mL) was added ethylene glycol (25 mL, 445.8 mmole) and p-toluenesulfonic acid hydrate (848 mg, 4.458 mmole). The mixture was heated to reflux under a Dean-Stark trap. After 18 hr the mixture was cooled to RT, washed with saturated NaHCO$_3$ then with H$_2$O, dried (MgSO$_4$), and concentrated under reduced pressure to give the title compound (6.32 g, 91%) as a light amber oil: $^1$H NMR (400 MHz, CDCl$_3$) δ 7.42 (s, 1H), 7.32 (m, 1H), 7.16 (m, 1H), 5.91 (s, 1H), 4.12-3.99 (m, 4H).

b) 2-(Carboethoxymethylthio)-3-(1,3-dioxolan-2-yl) thiophene

To a solution of 3-(1,3-dioxolan-2-yl)thiophene (6.32 g, 40.46 mmole) in dry THF (200 mL) was added a solution of n-BuLi in hexanes (1.7 M, 28.8 mL, 49 mmole) slowly at −78° C. After 30 min sulfur (1.57 g, 49 mmole) was added all at once. After 30 min ethyl bromoacetate (7.4 mL, 66.87 mmole) was added slowly, and after another 30 min the mixture was warmed to RT. After 2 hr at RT the mixture was concentrated under reduced pressure. The residue was taken up in Et$_2$O, washed with H$_2$O (3×), dried (MgSO$_4$), and concentrated to give the title compound as an oil which was sufficiently pure for use in the next step.

c) 2-(Carboethoxymethylthio)-3-formylthiophene

To a solution of 2-(carboethoxymethylthio)-3-(1,3-dioxolan-2-yl)thiophene (from step b) in acetone (200 mL) was added p-toluenesulfonic acid (761 mg, 4.0 mmole) at RT. After 18 hr the mixture was concentrated. The residue was taken up in Et$_2$O, washed with saturated NaHCO$_3$, H$_2$O (2×), dried (MgSO$_4$), and concentrated under reduced pressure to give the title compound as an oil which was sufficiently pure for use in the next step.

d) Ethyl thieno[2,3-b]thiophene-2-carboxylate

To a solution of 2-(carboethoxymethylthio)-3-formylthiophene (from step c) in MeOH (200 mL) was added DBU (0.6 mL, 4.0 mmole) at 0° C. After 1 hr the mixture was warmed to RT and concentrated. The residue was taken up in EtOAc, washed with 10% HCl, H$_2$O (3×), dried (MgSO$_4$, and concentrated. Flash chromatography on silica gel (50% toluene/hexanes) gave the title compound (3.84 g, 45% over 4 steps) as an off-white solid: $^1$H NMR (400 MHz, CDCl$_3$) δ 7.95 (s, 1H), 7.40 (d, J=5.2 Hz, 1H), 7.26 (d, J=5.2 Hz, 1H), methyl ester 3.92 (s, 3H), ethyl ester 4.38 (q, J=7.1 Hz, 2H)) and 1.41 (t, J=2.4 Hz, 3H).

e) N-Methyl-2-(thieno[2,3-b]thiophene)carboxamide

A suspension of ethyl thieno[2,3-b]thiophene-2-carboxylate (3.84 g, 18.1 mmole) in 40% aqueous CH$_3$NH$_2$ (100 mL) and MeOH (10 mL) was stirred at RT for 18 hr. During that time the suspension became a solution. The mixture was concentrated to approximately ⅓ volume at which time the product precipitated. The solid was collected by filtration, washed with H$_2$O, and dried in vacuo to give the title compound (3.01 g, 85%): $^1$H NMR (400 MHz, d$^6$-DMSO) δ 8.60 (bs, 1H), 7.92 (s, 1H), 7.67 (d, J=5.2 Hz, 1H), 7.38 (d, J=5.2 Hz, 1H), 2.78 (d, J=4:6 Hz, 3H).

f) 2-(Methylaminomethyl)thieno[2,3-b]thiophene

To a solution of N-methyl-2-(thieno[2,3-b]thiophene)carboxamide (3.01 g, 15.26 mmole) in dry THF (75 mL) was added a solution of LiAlH$_4$ in THF (1.0 M, 30 mL, 30 mmole) slowly at RT. After gas evolution had ceased the mixture was heated to a gentle reflux. After 18 hr the mixture was cooled to RT and quenched by dropwise addition of 2.0 M NaOH until a white solid had formed. The mixture was dried over MgSO$_4$, filtered, and concentrated under reduced pressure to give the title compound (2.18 g, 78%) as a brown oil: $^1$H NMR (400 MHz, CDCl$_3$) δ 7.30 (d, J=5.2 Hz, 1H), 7.15 (d, J=5.2 Hz, 1H), 7.04 (s, 1H), 4.00 (s, 2H), 2.49 (s, 3H).

Preparation 8

Preparation of 2-(methylaminomethyl)thieno[3,2-b]thiophene a) N-Methyl-2-(thieno[3,2-b]thiophene)carboxamide EDC (624 mg, 3.26 mmole) was added to a solution thieno [3,2-b]thiophene-2-carboxylic acid (500 mg, 2.71 mmole), CH$_3$NH$_2$ (2.0 M in THF, 2.7 mL, 5.42 mmole), HOBt.H$_2$O (440 mg, 3.26 mmole), and Et$_3$N (0.95 mL, 6.78 mmole) in dry DMF (14 mL) at RT. After 18 hr the mixture was diluted with H$_2$O and extracted with EtOAc (3×). The combined organic layers were dried (MgSO$_4$) and concentrated to give the title compound (415 mg, 78%) which was sufficiently pure for use in the next step: $^1$H NMR (400 MHz, CDCl$_3$) δ 7.70 (s, 1H), 7.52 (d, J=5.3 Hz, 1H), 7.27 (d, J=5.3 Hz, 1H), 3.02 (d, J=4.9 Hz, 3H).

b) 2-(Methylaminomethyl)thieno[3,2-b]thiophene

To a solution of N-methyl-2-(thieno[3,2-b]thiophene)carboxamide (415 mg, 2.1 mmole) in dry THF (10 mL) was added a solution of LiAlH$_4$ in THF (1.0 M. 4.2 mL, 4.2 mmole) slowly at RT. After gas evolution had ceased the mixture was heated to a gentle reflux. After 18 hr the mixture was cooled to RT and quenched by dropwise addition of 2.0 M NaOH until a white solid had formed. The mixture was dried (MgSO$_4$), filtered, and concentrated to give the title compound (361 mg, 94%) as a brown oil: $^1$H NMR (400 MHz, CDCl$_3$) δ 7.31 (d, J=5.2 Hz, 1H), 7.21 (d, J=5.2 Hz, 1H), 7.11 (s, 1H), 4.01 (s, 2H), 2.50 (s, 3H).

Preparation 9

Preparation of (E)-3-(3H-imidazo[4,5-b]pyridin-6-yl)acrylic acid a) 5-Bromo-2,3-diaminopyridine To a suspension of 2-amino-5-bromo-3-nitropyridine (2.0 g, 9.17 mmole) in absolute EtOH (50 mL) was added SnCl$_2$ hydrate (9.3 g, 41.3 mmole), then the mixture was heated to reflux. After 3 hr the mixture was cooled to RT and concentrated. The residue was taken up in 2.0 M NaOH and extracted with EtOAc (3×). The combined organic layers were dried (MgSO$_4$, filtered, and concentrated to give the title compound (1.69 g, 98%) which was sufficiently pure for use in the next step: MS (ES) m/e 188/190 (M+H)$^+$.

b) 6-Bromo-3H-imidazo[4,5-b]pyridine

5-Bromo-2,3-diaminopyridine (1.69 g, 8.99 mmole) was taken up in 96% formic acid (50 mL) and heated to reflux. After 18 hr the mixture was cooled to RT and concentrated. The residue was taken up in H$_2$O and the pH was adjusted to 7 with 2.0 M NaOH. The title compound (1.54 g, 87%) was collected as a solid by filtration, washed with $H_2O$, and dried in vacuo: MS (ES) m/e 198/200 (M+H)$^+$.

c) 6-Bromo-4-trityl-3H-imidazo[4,5-b]pyridine

To a suspension of 6-bromo-3H-imidazo[4,5-b]pyridine (1.2 g, 6.06 mmole) in $CH_2Cl_2$ (30 mL) was added $Et_3N$ (1.3 mL, 9.09 mmole) then trityl chloride (2.03 g, 7.27 mmole) at RT. After 72 hr the mixture was washed with $H_2O$ (2×) and brine, then was dried ($MgSO_4$), filtered, and concentrated under reduced pressure to afford the title compound. This was used directly in the next step.

d) Benzyl (E)-3-(4-trityl-3H-imidazol[4,5-b]pyridin-6-yl)acrylate

A solution of 6-bromo-4-trityl-3H-imidazo[4,5-b]pyridine (from step a) (6.06 mmole), benzyl acrylate (1.18 g, 7.27 mmole), Pd(OAc)$_2$ (67 mg, 0.30 mmole), P(o-tolyl)$_3$ (183 mg. 0.6 mmole), and (i-Pr)$_2$NEt (2.64 mL, 15.15 mmole) in propionitrile (30 mL) was degassed (3×$N_2$/vacuum) then heated to reflux. After 4 hr the mixture was cooled to RT and concentrated. Flash chromatography on silica gel (30% EtOAc/hexanes) gave the title compound (1.75 g, 55% over 2 steps) as an off-white foam: $^1$H NMR (400 MHz, CDCl$_3$) δ 8.24 (d, J=2.0 Hz, 1H), 8.19 (d, J=2.0 Hz, 1H), 8.06 (s, 1H), 7.77 (d, J=16.0 Hz, 1H), 7.42-7.11 (m, 20H), 6.48 (d, J=16.0 Hz, 1H), 5.25 (s, 2H).

d) (E)-3-(3H-Imidazo[4,5-b]pyridin-6-yl)acrylic acid

Benzyl (E)-3-(4-trityl-3H-imidazo[4,5-b]pyridin-6-yl) acrylate (1.75 g, 3.35 mmole) was dissolved in 4 N HCl in dioxane (20 mL). After 1 hr the mixture was concentrated. The residue was taken up in 1:1 MeOH/$H_2O$ (15 mL). 2.0 N NaOH (15 mL, 15 mmole) was added and the mixture was heated to reflux. After 18 hr the mixture was cooled to RT and concentrated to approximately ⅓ volume. The mixture was adjusted to pH 4 using 10% HCl. The solid was collected by filtration, washed with $H_2O$, and dried in vacuo to give the title compound (329 mg, 52% over 2 steps) as a white solid: $^1$H NMR (400 MHz, d$^6$-DMSO) δ 9.10 (s, 1H), 8.94 (s, 1H), 8.84 (s, 1H), 8.20 (d, J=16.0 Hz, 1H), 7.10 (d, J=16.0 Hz, 1H).

Preparation 10

Preparation of 6-methyl-5-(methylaminomethyl)-6H-thieno[2,3-b]pyrrole a) Ethyl (Z)-2-azido-3-(thiophen-3-yl)acrylate To a solution of thiophene-3-carboxaldehyde (500 mg, 4.46 mmole) and ethyl 2-azido acetate (863 mg, 6.69 mmole) in absolute EtOH (20 mL) was added NaOEt (21%. 2.2 mL, 6.69 mmole) at 0° C. After 1 hr the mixture was quenched with saturated $NH_4Cl$ and extracted with $Et_2O$ (3×). The combined organic layers were dried ($MgSO_4$) filtered, and concentrated. Flash chromatography on silica gel (50% CHCl$_3$/hexanes) gave the title compound (208 mg, 21%) as a pale yellow oil: $^1$H NMR (400 MHz, CDCl$_3$) δ 7.87 (m, 1H), 7.49 (m, 1H), 7.31 (m, 1H), 6.96 (s, 1H), 4.36 (q, J=7.1 Hz, 2H), 1.39 (t, J=7.1 Hz, 3H).

b) Ethyl 6H-thieno[2,3-b]pyrrole-5-carboxylate

A solution of ethyl (Z)-2-azido-3-(thiophen-3-yl)acrylate (208 mg, 0.93 mmole) in xylenes (5 mL) was heated to reflux.

After 30 min the mixture was cooled to RT and concentrated to give the title compound (175 mg, 96%) which was sufficiently pure for use in the next step: $^1$H NMR (400 MHz, CDCl$_3$) δ 9.26 (bs, 1H), 7.10 (m, 1H), 7.00 (m, 1H), 6.91 (m, 1H), 4.36 (q, J=7.1 Hz, 2H), 1.39 (t, J=7.1 Hz, 3H).

c) N,6-Dimethyl-6H-thieno[2,3-b]pyrrole-5-carboxamide

To a solution of ethyl 6H-thieno[2,3-b]pyrrole-5-carboxylate (175 mg. 0.9 mmole, see *J. Het. Chem.* 1984, 21, 215-217) and MeI (0.08 mL, 1.35 mmole) in dry DMF (5 mL) was added NaH (60% dispersion in mineral oil, 43 mg, 1.08 mmole) at 0° C. After 2 hr the mixture was quenched with saturated $NH_4Cl$ and extracted with EtOAc (3×). The combined organic layers were dried ($MgSO_4$), filtered, and concentrated to an oil.

A solution of the above oil in 40% aqueous $CH_3NH_2$ (20 mL) and MeOH (1 mL) was stirred at RT for 18 hr. The mixture was concentrated to approximately ⅓ by volume at which time the product precipitated. The solid was collected by filtration, washed with $H_2O$, and dried in vacuo to give the title compound (134 mg, 74% over 2 steps): MS (ES) m/e 195 (M+H)$^+$.

d) 6-Methyl-5-(methylaminomethyl)-6H-thieno[2,3-b]pyrrole

To a solution of N,6-dimethyl-6H-thieno[2,3-b]pyrrole-5-carboxamide (134 mg, 0.69 mmole) in dry THF (5 mL) was added a solution of LiAlH$_4$ in THF (1.0 M, 1.38 mL, 1.38 mmole) slowly at RT. After gas evolution had ceased the mixture was heated to a gentle reflux. After 2 hr the mixture was cooled to RT and quenched by dropwise addition of 2M NaOH until a white solid had formed. The mixture was dried ($MgSO_4$, filtered, and concentrated to give the title compound as a brown oil (142 mg, 100%) which was sufficiently pure for use in the next step: $^1$H NMR (400 MHz, CDCl$_3$) δ 6.95 (d, J=5.2 Hz, 1H), 6.78 (d, J=5.2 Hz, 1H), 6.27 (s, 1H), 3.78 (s, 2H), 3.72 (s, 3H), 2.47 (s, 3H).

Preparation 11

Preparation of (E)-3-(2-aminopyrimidin-5-yl)acrylic acid a) Benzyl (E)-3-(2-aminopyrimidin-5-yl)acrylate According to the procedure of Preparation 2 (a), except substituting 5-bromo-2-aminopyrimidine (1.95 g, 11.2 mmole) for 2-amino-5-bromopyridine, the title compound (2.25 g, 79%) was prepared as a light orange solid: MS (ES) m/e 256 (M+H)$^+$.

b) (E)-3-(2-Aminopyrimidin-5-yl)acrylic acid

According to the procedure of Preparation 2 (b), except substituting benzyl (E)-3-(2-aminopyrimidin-5-yl)acrylate (2.93 g, 11.5 mmole) for benzyl (E)-3-(6-aminopyridin-3-yl) acrylate, the title compound (1.71 g, 90%) was prepared as an off-white solid: MS (ES) m/e 166 (M+H)$^+$.

Preparation 12

Preparation of (E)-3-(6-aminopyridin-3-yl)-2-methylacrylic acid a) Methyl (E)-3-(6-aminopyridin-3-yl)-2-methylacrylate According to the procedure of Preparation 2 (a), except substituting methyl crotonate (4.33 g, 43.3 mmole) for benzyl acrylate, the title compound (1.0 g, 18%) was prepared as an off-white solid: MS (ES) m/e 193 (M+H)+.

b) (E)-3-(6-Aminopyridin-3-yl)-2-methylacrylic acid

According to the procedure of Preparation 2 (b), except substituting methyl (E)-3-(6-aminopyridin-3-yl)-2-methylacrylate (1.0 g, 5.2 mmole) for benzyl (E)-3-(6-aminopyridin-3-yl)acrylate, the title compound (0.83 g, 90%) was prepared as an off-white solid: MS (ES) m/e 179 (M+H)+.

Preparation 13

Preparation of (E)-3-(6-amino-2-methylpyridin-3-yl) acrylic acid a) Benzyl (E)-3-(6-amino-2-methylpyridin-3-yl) acrylate According to the procedure of Preparation 2 (a), except substituting 2-amino-5-bromo-6-methylpyridine (5.00 g, 26.7 mmole) for 2-amino-5-bromopyridine, the title compound (5.58 g, 78%) was prepared as an off-white solid: MS (ES) m/e 269 (M+H)+.

b) (E)-3-(6-Amino-2-methylpyridin-3-yl)acrylic acid

According to the procedure of Preparation 2 (b), except substituting benzyl (E)-3-(6-amino-2-methylpyridin-3-yl) acrylate (2.20 g, 8.2 mmole) for benzyl (E)-3-(6-aminopyridin-3-yl)acrylate, the title compound (1.31 g, 90%) was prepared as an off-white solid: MS (ES) m/e 179 (M+H)+.

Preparation 14

Preparation of (E)-3-(6-amino-5-methylpyridin-3-yl) acrylic acid a) Benzyl (E)-3-(6-amino-5-methylpyridin-3-yl) acrylate According to the procedure of Preparation 2 (a), except substituting 2-amino-5-bromo-3-methylpyridine (5.00 g, 26.7 mmole) for 2-amino-5-bromopyridine, the title compound (6.37 g, 89%) was prepared as an off-white solid: MS (ES) m/e 269 (M+H)+.

b) (E)-3-(6-Amino-5-methylpyridin-3-yl)acrylic acid

According to the procedure of Preparation 2 (b), except substituting benzyl (E)-3-(6-amino-5-methylpyridin-3-yl) acrylate (5.00 g, 18.6 mmole) for benzyl (E)-3-(6-aminopyridin-3-yl)acrylate, the title compound (2.98 g, 90%) was prepared as an off-white solid: MS (ES) m/e 179 (M+H)+.

Preparation 15

Preparation of (E)-3-[6-amino-5-(hydroxymethyl) pyridin-3-yl]acrylic acid a) 2-Amino-3-(hydroxymethyl)pyridine To a solution of 2-aminonicotinic acid (20.5 g, 148.1 mmole) in THF was added lithium aluminum hydride (300 mL, 1.0 M in THF) over 30 minutes. The reaction solution was heated to reflux for 18 hrs and then was cooled to room temperature. The reaction was quenched by the sequential dropwise addition of H$_2$O (11.5 mL), 15% NaOH (11.5 mL), and H$_2$O (34.5 mL). The mixture was stirred for 15 min, then was filtered through Celite®, and the filter pad was washed thoroughly with THF followed by 5% CH$_3$OH/CHCl$_3$. The filtrate was concentrated to give the title compound (15.24 g, 83%) as a waxy light yellow solid: MS (ES) m/e 125 (M+H)+.

b) 2-Amino-5-bromo-3-(hydroxymethyl)pyridine

To a solution of 2-amino-3-(hydroxymethyl)pyridine (13.0 g, 116.0 mmole) in CH$_2$Cl$_2$ (300 mL) at RT was added NBS (22.71 g, 127.6 mmole). After stirring at RT for 45 min the reaction solution was concentrated and the residue was dissolved in CHCl$_3$. The resulting suspension was filtered and the filtrate was concentrated to a dark oil. Purification on silica gel (EtOAc) afforded the title compound (78%, 18.36 g) as a tan solid: MS (ES) m/e 204 (M+H)+.

c) Benzyl (E)-3-[6-amino-5-(hydroxymethyl)pyridin-3-yl]acrylate

According to the procedure of Preparation 2 (a), except substituting 2-amino-3-(hydroxymethyl)-5-bromopyridine (1.10 g, 5.42 mmole) for 2-amino-5-bromopyridine, the title compound (1.25 g, 81%) was prepared as an off-white solid: MS (ES) m/e 285 (M+H)+.

d) (E)-3-[6-Amino-5-(hydroxymethyl)pyridin-3-yl] acrylic acid

According to the procedure of Preparation 2 (b) except substituting benzyl-(E)-3-[6-amino-5-(hydroxymethyl)pyridin-3-yl]acrylate (1.10 g, 5.42 mmole) for benzyl (E)-3-(6-aminopyridin-3-yl)acrylate, the title compound (0.68 g, 65%) was prepared as an off-white solid: MS (ES) m/e 194 (M+H)+.

Preparation 16

Preparation of 6-bromo-3,4-dihydro-1H-1,8-naphthyridin-2-one a) 2-Amino-5-bromo-3-(bromomethyl)pyridine hydrobromide A solution of 2-amino-5-bromo-3-hydroxymethylpyridine (5.00 g, 24.6 mmole), from Preparation 14 (b), in 48% aqueous HBr (50 mL), was heated at reflux for 12 hrs. The reaction was concentrated and toluene was used to azeotrope the residual H$_2$O. The resulting light brown solid was placed under high vacuum overnight and used directly.

b) Methyl (±)-6-bromo-2-oxo-1,2,3,4-tetrahydro-1H-1,8-naphthyridine-3-carboxylate To a solution of sodium methoxide (20.57 mL, 25% wt in CH$_3$OH) in CH$_3$OH (75 mL) was added dimethyl malonate (11.87 g, 89.9 mmole). After 30 min the 2-amino-5-bromo-3-(bromomethyl)pyridine hydrobromide salt prepared above was added to the methoxide solution and the reaction was stirred at RT overnight. The reaction slurry was concentrated to dryness under vacuum and then suspended in 1:1 H$_2$O/Et$_2$O. The remaining solids were filtered and washed with H$_2$O then with hexanes to afford the title compound (4.08 g, 58%) as a white solid after drying: MS (ES) m/e 286 (M+H)+.

c) 6-Bromo-3,4-dihydro-1H-1,8-naphthyridin-2-one

To a solution of methyl (±)-6-bromo-2-oxo-1,2,3,4-tetrahydro-1H-1,8-naphthyridine-3-carboxylate (2.00 g, 7.0 mmole) in CH₃OH (75 mL) was added 1.0 M NaOH (30 mL). The reaction was heated to reflux for 4 hrs and then cooled to RT. The reaction was neutralized with 1.0 M HCl (30 mL) then was heated at reflux overnight. The reaction slurry was concentrated to dryness and the residues was suspended in 95:5 CHCl₃/CH₃OH. The solids were removed by filtration and the filtrate was concentrated to afford the title compound (1.40 g, 88%) as an off-white solid: MS (ES) m/e 228 (M+H)⁺.

Preparation 17

Preparation of (E)-3-[6-amino-5-[(2-hydroxyethylamino)carbonyl]pyridin-3-yl]acrylic acid a)
2-Amino-5-bromo-N-(2-hydroxyethyl)nicotinamide EDC (2.91 g, 15.2 mmole) was added to a solution 2-amino-5-bromonicotinic acid (3.00 g, 13.8 mmole), ethanolamine (0.93 g, 15.2 mmole), HOBt.H₂O (2.05 g, 15.2 mmole), and diisopropylethylamine (2.64 mL, 15.2 mmole) in DMF (50 mL) at RT and the reaction solution was stirred overnight. The reaction contents were poured into H₂O (200 mL) and the resulting mixture was extracted with EtOAc (2×200 mL). The combined organic extracts were washed with H₂O and brine and then dried over Na₂SO₄. Concentration of the organic extracts afforded the title compound as a yellow solid which was used without further purification: MS (ES) m/e 261 (M+H)⁺.

b) Benzyl (E)-3-[6-amino-5-[(2-hydroxyethylamino)carbonyl]pyridin-3-yl]acylate

According to the procedure of Preparation 2 (a), except substituting 2-amino-5-bromo-N-(2-hydroxyethyl)nicotinamide (2.70 g, 10.4 mmole) for 2-amino-5-bromopyridine, the title compound (2.67 g, 75%) was prepared as an off-white solid: MS (ES) m/e 342 (M+H)⁺.

c) (E)-3-[6-Amino-5-[(2-hydroxyethylamino)carbonyl]pyridin-3-yl]acrylic acid

According to the procedure of Preparation 2 (b), except substituting benzyl (E)-3-[6-amino-5-[(2-hydroxyethylamino)carbonyl]pyridin-3-yl]acrylate (2.67 g, 7.8 mmole) for benzyl (E)-3-(6-aminopyridin-3-yl)acrylate the title compound (1.37 g, 70%) was prepared as an off-white solid: MS (ES) m/e 252 (M+H)⁺.

Preparation 18

Preparation of 6-bromo-3-methyl-3,4-dihydro-1H-pyrido[2,3-b]pyrimidin-2-one a)
2-Amino-5-bromo-3-(methylaminomethyl)pyridine A solution of 2-amino-5-bromo-3-(hydroxymethyl)pyridine (5.00 g, 24.6 mmole), from Preparation 14 (b), in 48% aqueous HBr (50 mL) was heated at reflux for 12 hrs. The reaction was concentrated and toluene was used to azeotrope the residual H₂O. The resulting light brown solid was placed under high vacuum overnight and used directly.

A solution of the 2-amino-3-(bromomethyl)-5-bromopyridine hydrobromide salt (prepared above) in 40% aqueous methylamine (50 mL) and THF (50 mL) was stirred at RT overnight in a pressure bottle. The reaction solution was concentrated and extracted with EtOAc (2×100 mL). The combined organic phases were washed with H₂O, dried over Na₂SO₄ and concentrated. Purification on silica gel afforded the title compound (4.25 g, 80%) as a yellow oil: MS (ES) m/e 217 (M+H)⁺.

b) 6-Bromo-3-methyl-3,4-dihydro-1H-pyrido[2,3-d]pyrimidin-2-one

To a solution of dimethyl carbonate (2.14 g, 23.7 mmole) and sodium methoxide (1.0 mL, 4.5 mmole. 25% wt in CH₃OH) in CH₃OH (25 mL) was added 2-amino-5-bromo-3-(methylaminomethyl)pyridine (1.0 g, 4.62 mmole). The reaction was heated at 50° C. overnight, diluted with H₂O (1 mL) and concentrated. Toluene was added to the reaction residue and the contents were heated to reflux for 12 hr under a Dean-Stark apparatus. The reaction was cooled to RT, diluted with EtOAc, and washed with H₂O. Purification on Silica gel (9:1 CHCl₃/CH₃OH containing 5% NH₄OH) gave the title compound (0.75 g, 67%) as an off-white solid: MS (ES) m/e 243 (M+H)⁺.

Preparation 19

Preparation of 4-methyl-5-methylaminomethyl)-4H-thieno[3,2-b]pyrrole a) Ethyl 4-methyl-4H-theino[3,2-b]pyrrole-5-carboxylate According to the procedure of Preparation 1 (a), except substituting ethyl 4H-theino[3,2-b]pyrrole-5-carboxylate (1.30 g, 6.7 mmole, see *J. Het. Chem.* 1984, 21, 215-217) for ethyl indole-2-carboxylate, the title compound (1.35 g, 97%) was prepared as a yellow solid: MS (ES) m/e 210 (M+H)⁺.

b)
N,4-Dimethyl-4H-thieno[3,2-b]pyrrole-5-carboxamide

According to the procedure of Preparation 1 (b), except substituting ethyl 4-methyl-4H-thieno[3,2-b]pyrrole-5-carboxylate (1.35 g, 6.5 mmole) for ethyl-1-methylindole-2-carboxylate, the title compound (1.19 g, 95%) was prepared as a yellow solid: MS (ES) m/e 195 (M+H)⁺.

c) 4-Methyl-5-(methylaminomethyl)-4H-thieno[3,2-b]pyrrole

According to the procedure of Preparation 1 (c), except substituting N,4-dimethyl-4H-thieno[3,2-b]pyrrole-5-carboxamide (0.70 g, 3.6 mmole) for N,1-dimethylindole-2-carboxamide, the title compound (0.60 g, 92%) was prepared as a yellow oil: MS (ES) m/e 181 (M+H)⁺.

Preparation 20

Preparation of 3-methyl-2-(methylaminomethyl)indene hydrochloride a) N,3-Dimethylinden-2-carboxamide EDC (1.53 g, 0.01 mole), was added to a solution of 3-methyl-2-inden-2-carboxylic acid (1.91 g, 0.01 mole), methylamine hydrochloride (0.675 g, 0.01 mole), HOBt.H₂O (1.53 g, 0.01 mole) and triethylamine (4.0 mL, 0.028 mole) in anhydrous DMF (80 mL) at RT. The reaction was stirred overnight, then was concentrated in vacuo. The residue was diluted with 5% NaHCO$_3$ and the resulting white precipitate was collected, washed with water and dried at 50° C. in a vacuum oven to afford the title compound (1.6 g, 86%) as a white solid: MS (ES) m/e 188.2 (M+H)$^+$.

b) 3-Methyl-2-(methylaminomethyl)indene hydrochloride

A flame-dried flask was charged with anhydrous THF (15 mL) followed by solid lithium aluminum hydride (760 mg, 0.02 mole) at 0° C. The mixture was stirred for 15 min, then a solution of N,3-dimethylindene-2-carboxamide (1.5 g, 0.008 mole) in anhydrous THF (20 mL) was added dropwise. When the addition was complete, the reaction was heated at gentle reflux for 30 hr, then was cooled in ice and quenched with H$_2$O (1.4 mL) and NaF (2.5 g, 0.06 mole). The reaction mixture was stirred for 40 min then was filtered through Celite®, and the filter pad was washed with THF. The filtrate was dried over K$_2$CO$_3$, filtered and concentrated to an oil, which was dissolved in anhydrous ethyl ether and treated with 4 M HCl in diethyl ether. The precipitated light tan solid was collected by suction filtration and washed with diethyl ether. Drying at 50° C. in a vacuum oven gave the title compound (1.05 g, 80.7%) as a light tan solid: MS (ES) m/e 174.2 (M+H)$^+$.

Preparation 21

Preparation of 2-(methylaminomethyl)indene hydrochloride a) N-Methylindene-2-carboxamide According to the procedure of Preparation 20 (a), except substituting 2-inden-carboxylic acid for 3-methyl-2-inden-2-carboxylic acid, the title compound was obtained as a white crystalline solid (1.45 g, 83.3%): MS (ES) m/e 174.2 (M+H)$^+$.

b) 2-(Methylaminomethyl)indene hydrochloride

According to the procedure of Preparation 20 (b), except substituting N-methylindene-2-carboxamide for N,3-dimethylindene-2-carboxamide, the title compound was obtained as an off-white solid (0.685 g, 87.6%): MS (ES) m/e 160.0 (M+H)$^+$.

Preparation 22

Preparation of 4-methoxy-1-methyl-2-(methylaminomethyl)-1H-indole hydrochloride a) Methyl 4-methoxy-1-methyl-1H-indol-2-carboxylate NaH (60% dispersion in mineral oil, 0.3 g, 7.3 mmole) was washed with hexane then suspended in anhydrous DMF (16 mL). The mixture was cooled to 0° C. and methyl 4-methoxy-1H-indol-2-carboxylate (1.0 g, 4.87 mmole) was added. The mixture was stirred under argon for 10 min, then MeI (1.3 mL, 20 mmole) was added, and the thick slurry was stirred at RT for 2.5 hr. The reaction was quenched with 10% NH$_4$Cl (2 mL) and concentrated. The residue was partitioned between H$_2$O and Et$_2$O, and the organic layer was dried over MgSO$_4$ and concentrated to yield the title compound (1.03 g, 96%) as a white solid: MS (ES) m/e 220.2 (M+H)$^+$.

b) N,1-Dimethyl-4-methoxy-1H-indol-2-carboxamide

A solution of methyl 4-methoxy-1-methyl-1H-indol-2-carboxylate (1.03 g, 4.7 mmole) in 2.0 M methylamine in methanol (40 mL) was sealed in a pressure bottle and heated at 55-60° C. for 60 hr. Concentration in vacuo yielded the title compound (1.05 g, quantitative) as a white solid: MS (ES) m/e 219.2 (M+H)$^+$.

c) 4-Methoxy-1-methyl-2-(methylaminomethyl-1H-indole hydrochloride

According to the procedure of Preparation 20 (b), except substituting N,1-dimethyl-4-methoxy-1H-indol-2-carboxamide for N,3-dimethylindene-2-carboxamide, the title compound was obtained as an off white solid (0.72 g, 75%): MS (ES) m/e 205.2 (M+H)$^+$.

Preparation 23

Preparation of 1,4-dimethyl-2-(methylaminomethyl)-1H-indole hydrochloride a) 1,4-Dimethyl-1H-indol-2-carboxylic acid A solution of 1,4-dimethyl-1H-indole (0.9 g, 6.2 mmole) in anhydrous Et$_2$O (20 mL) was treated with 2.5 M n-BuLi in hexanes (5.0 mL, 12 mmole) and the reaction was heated at reflux for 15 hr. The dark reaction mixture was poured into a slurry of excess crushed dry ice in Et$_2$O, and the mixture was allowed to stand for 1 hr. Water (10 mL) was added, the layers separated, and the aqueous layer was filtered through Celite®. The clear filtrate was acidified with 2.0 N HCl to pH 2, and the precipitate was collected and dried to afford the title compound (0.29 g, 26.4%) as an off-white solid: MS (ES) m/e 190.2 (M+H)$^+$.

b) N,1,4-Trimethyl-1H-indol-2-carboxamide

According to the procedure in Preparation 20 (a), except substituting 1,4-dimethyl-1H-indole-2-carboxylic acid for 3-methyl-2-indene-2-carboxylic, the title compound was obtained (0.184 g, 91%): MS (ES) m/e 203.2 (M+H)$^+$.

c) 1,4-Dimethyl-2-(methylaminomethyl)-1H-indole hydrochloride

According to the procedure in Preparation 20 (b), except substituting N,1,4-trimethyl-1H-indole-2-carboxamide for N,3-dimethylindene-2-carboxamide, the title compound was obtained (0.13 g, 65%): MS (ES) m/e 189.2 (M+H)$^+$.

Preparation 24

Preparation of 2-(cyclopropylamino)-methyl-1H-indole a) 2-(Cyclopropylamino)-1-methyl-1H-indole To a solution of 1-methylindole-2-carboxaldehyde (1.5 g, 10 mmole), cyclopropylamine (1.14 g, 20 mmole), and glacial acetic acid (0.6 mL, 10 mmole) in MeOH (30 mL) was added NaBH₃CN (0.69 g, 11 mmole). The reaction was stirred at RT overnight, then was concentrated in vacuo. The residue was diluted with 10% NaOH and extracted with CH₂Cl₂. The combined organic extracts were washed with brine, dried over MgSO₄, and concentrated. Flash chromatography on silica gel (3% MeOH/CH₂Cl₂) gave the title compound (1.3 g, 65%) as a semi-solid: MS (ES) m/e-201 (M+H)⁺.

Preparation 25

Preparation of 5-fluoro-2-(methylaminomethyl)-1H-indole a) Ethyl 5-fluoro-1-methyl-1H-indole-2-carboxylate According to the procedure of Preparation 1 (a), except substituting ethyl 5-fluoro-indole-2-carboxylate for the ethyl-indole-2-carboxylate, the title compound (3.3 g, 100%) was prepared as a white solid: MS (ES) m/e 222 (M+H)⁺.

b) N,1-Dimethyl-5-fluoro-1H-indole-2-carboxamide

According to the procedure of Preparation 1 (b), except substituting ethyl S-fluoro-1-methyl-1H-indole-2-carboxylate for the ethyl 1-methyl-1H-indole-2-carboxylate, the title compound (2.1 g, 68%) was prepared as a white solid: MS (ES) m/e 207 (M+H)⁺.

c) 5-Fluoro-2-(methylaminomethyl)-1H-indole

According to the procedure of Preparation 1 (c), except substituting N,1-dimethyl-5-fluoro-1H-indole-2-carboxamide for the N,1-dimethyl-1H-indole-2-carboxamide, the title compound (1.5 g, 78%) was prepared as a white solid: MS (ES) m/e 193 (M+H)⁺.

Preparation 26

Preparation of 3-(methylaminomethyl)quinoline a) 3-(Methylaminomethyl)quinoline

A solution of 3-quinolinecarboxaldehyde (1.5 g, 10 mmole), 2.0 M CH₃NH₂/MeOH (10 mL, 20 mmole), glacial AcOH (0.6 mL, 10 mmole), and NaBH₃CN (0.35 g, 11 mmole) in MeOH (20 mL) was stirred at RT overnight, then was concentrated in vacuo. The residue was diluted with 5% NaOH and extracted with CH₂Cl₂. The combined organic extracts were washed with brine, dried over MgSO₄, and concentrated. Flash chromatography on silica gel (10% MeOH/CH₂Cl₂) gave the title compound (0.83 g, 24%) as a slightly yellow viscous oil: MS (ES) m/e 173 (M+H)⁺.

Preparation 27

Preparation of 2-(methylaminomethyl)benzofuran a) N-Methylbenzofuran-2-carboxamide To a solution of 2-benzofurancarboxylic acid (1.62 g, 10 mmole), methylamine hydrochloride (0.79 g, 10 mmole), triethylamine (3.1 mL, 22 mmole), and HOBt.H₂O (1.5 g, 11 mmole) in DMF (30 mL) was added EDC (2.1 g, 11 mmole). The reaction was stirred overnight then was concentrated in vacuo. The residue was diluted with 5% NaHCO₃ and extracted with CH₂Cl₂. The combined organic extracts were washed with brine, dried over MgSO₄, and concentrated. Flash chromatography on silica gel (3% MeOH/CH₂Cl₂) gave the title compound (1.75 g, 100%) as white solid: MS (ES) m/e 176 (M+H)⁺.

b) 2-(Methylaminomethyl)benzofuran

To a solution of 1.0 M BH₃/THF (30 mL, 30 mmole) at 0° C. was added N-methylbenzofuran-2-carboxamide (1.75 g, 10 mmole). The reaction mixture was allowed to warm to RT, then was heated at reflux overnight. The reaction was cooled to 0° C. and excess methanol was added. The resulting solution was concentrated in vacuo and the residue was purified by flash chromatography on silica gel (3% MeOH/CH₂Cl₂). The tile compound (0.2 g, 12%) was obtained as a white solid: MS (ES) m/e 162 (M+H)⁺.

Preparation 28

Preparation of 1-methyl-2-(propylaminomethyl)-1H-indole a) 1-Methyl-N-cyclopropylindole-2-carboxamide According to the procedure of Preparation 27 (a), except substituting 1-methyl-1H-indole-2-carboxylic acid (3.5 g, 20 mmole) for 2-benzofurancarboxylic acid, and substituting cyclopropylamine for methylamine hydrochloride, the title compound (2.1 g, 49%) was prepared as white solid: MS (ES) m/e 215 (M+H)⁺.

b) 1-Methyl-2-(propylaminomethyl)-1H-indole

To a solution of 1-methyl-N-cyclopropylindole-2-carboxamide (2.1 g, 9.8 mmole) in dry THF (40 mL) was added dropwise a solution of 1.0 M LiAlH₄ in THF (2.2 mL, 22 mmole). The reaction mixture was heated at reflux overnight, then was cooled and quenched with 10% NaOH. The mixture was filtered and the filtrate was concentrated in vacuo. Flash chromatography on silica gel (5% MeOH/CHCl₂) gave the title compound (0.65 g, 33%) as a viscous oil: MS (ES) m/e 203 (M+H)⁺.

Preparation 29

Preparation of 5-bromo-2-(methylamino)pyridine and 5-bromo-2-(dimethylamino)pyridine a) 5-Bromo-2-(methylamino)pyridine and 5-bromo-2-(dimethylamino)pyridine To a suspension of NaH (60% dispersion in mineral oil, 0.44 g, 11 mmole) in dry DMF (40 mL) was added solid 2-amino-5-bromopyridine (1.73 g, 10 mmole) in portions over 5-10 min. Gas evolution was allowed to subside between additions. The resulting amber mixture was stirred for 15 min, then methyl iodide (0.61 mL, 10 mmole) was added all at once. The reaction mixture was stirred at RT overnight, then was concentrated in vacuo. The residue was diluted with 5% NH₄Cl (30 mL) and the mixture was extracted with CH₂Cl₂. The combined organic extracts were washed with brine, dried (MgSO₄), and concentrated. Flash chromatography on silica gel (3% MeOH/CH₂Cl₂) separated the products. 5-Bromo-2-(methylamino)pyridine (0.60 g, 32%) was obtained as a semi-solid: TLC (3% MeOH/CH₂Cl₂) $R_f$ 0.35; MS (ES) m/e 187 (M+H)⁺⋅⁵-Bromo-2-(dimethylamino)pyridine (0.70 g, 34%)

was obtained as a semisolid: TLC (3% MeOH/CH$_2$Cl$_2$) R$_f$ 0.77; MS (ES) m/e 201 (M+H)$^+$.

Preparation 30

Preparation of (E)-3-[6-(methylamino)pyridin-3-yl]acrylic acid a) Benzyl (E)-3-[6-methylamino)pyridin-3-yl)acrylate According to the procedure of Preparation 2 (a), except substituting 5-bromo-2-(methylamino)pyridine for 2-amino-5-bromopyridine, the title compound (0.52 g, 60%) was prepared as a white solid: MS (ES) m/e 269 (M+H)$^+$.

b) (E)-3-[6-(Methylamino)pyridin-3-yl]acrylic acid

According to the procedure of Preparation 2 (b), except substituting benzyl (E)-3-[6-(methylamino)pyridin-3-yl] acrylate for benzyl (E)-3-(6-aminopyridin-3-yl)acrylate, the title compound (0.15 g, 43%) was prepared as a white solid: MS (ES) m/e 179 (M+H)$^+$.

Preparation 31

Preparation of (E)-3-[6-(dimethylaminopyridin-3-yl]acrylic acid a) Benzyl (E)-3-[6-(dimethylamino)pyridin-3-yl]acrylate According to the procedure of Preparation 2 (a), except substituting S-bromo-2-(dimethylamino)pyridine for 2-amino-5-bromopyridine, the title compound (0.82 g, 84%) was prepared as a white solid: MS (ES) m/e 283 (M+H)$^+$.

b) (E)-3-[6-(Dimethylamino)pyridin-3-yl]acrylic acid

According to the procedure of Preparation 2 (b), except substituting benzyl (E)-3-[6-(dimethylamino)pyridin-3-yl] acrylate for benzyl (E)-3-(6-aminopyridin-3-yl)acrylate, the title compound (0.20 g, 36%) was prepared as a white solid: MS (ES) m/e 193 (M+H)$^+$.

Preparation 32

Preparation of (E)-3-(6-methylpyridin-3-yl) acrylic acid a) Benzyl (E)-3-(6-methylpyridin-3-yl)acrylic acid According to the procedure of Preparation 2 (a), except substituting 5-bromo-2-methylpyridine for 2-amino-5-bromopyridine, the title compound (0.85 g, 34%) was prepared as a white solid: MS (ES) m/e 253 (M+H)$^+$.

b) (E)-3-(6-Methylpyridin-3-yl)acrylic acid

According to the procedure of Preparation 2 (b), except substituting benzyl (E)-3-(6-methylpyridin-3-yl)acrylic acid for benzyl (E)-3-(6-aminopyridin-3-yl)acrylate, the title compound (0.18 g, 33%) was prepared as a white solid: MS (ES) m/e 164 (M+H)$^+$.

Preparation 33

Preparation of 2-(methylaminomethyl)-1H-indole a) N-Methyl-1H-indol-2-carboxamide A suspension of ethyl indole-2-carboxylate (25.30 g, 133.7 mmole) in 40% aqueous CH$_3$NH$_2$ (400 mL) was stirred at RT. The flask was tightly stoppered to keep the material inside the flask. As the reaction proceeded the product began to precipitate. The reaction was stirred at RT for 3 days, then was concentrated to remove approximately 200 mL of the solvent. The remaining residue was diluted with H$_2$O (500 mL), and the solid was collected by suction filtration and washed with H$_2$O. Drying under high vacuum left the title compound (21.50 g, 92%) as a light yellow solid: MS (ES) m/e 175 (M+H)$^+$.

b) 2-(Methylaminomethyl)-1H-indole

A solution of LiAlH$_4$ in THF (1.0 M, 250 mL, 250 mmole) was slowly added via syringe to a solution of N-methyl-1H-indol-2-carboxamide (21.50 g, 12.34 mmole) in anhydrous THF (100 mL). Gas was evolved during the addition of the first 50 mL of LiAlH$_4$ solution. When the addition was complete, the resulting light yellow solution was heated at gentle reflux. After 23 hr, the reaction was cooled in ice and quenched by the sequential dropwise addition of H$_2$O (9.5 mL). 1.0 N NaOH (20 mL), and H$_2$O (28.5 mL). The mixture was stirred for 15 min. then was filtered through Celite®, and the filter pad was washed thoroughly with THF. The filtrate was concentrated and the residue was flash chromatographed on silica gel (10% MeOH/CHCl$_3$ containing 0.5% conc. NH$_4$OH). The title compound (10.10 g, 51%) was obtained as a light yellow oil: MS (ES) m/e 161 (M+H)$^+$.

Preparation 34

Preparation of 1-ethyl-2-(methylaminomethyl)-1H-indole a) 2-[N-(Benzyloxycarbonyl)-N-methylaminomethyl]-1H-indole N-(Benzyloxycarbonyloxy)succinimide (17.10 g, 68.6 mmole) was added to a solution of 2-(methylaminomethyl)-1H-indole (10.00 g, 62.4 mmole), from Preparation 33, and triethylamine (9.60 mL, 68.6 mmole) in DMF (100 mL) at RT. The reaction was stirred overnight then was concentrated in vacuo. The residue was diluted with water and the mixture was extracted with ethyl acetate. The combined extracts were dried over K$_2$CO$_3$ and concentrated. Flash chromatography on silica gel (20% ethyl acetate/hexanes) gave the title compound (14.80 g, 80%) as an off-white solid: MS (ES) m/e 295 (M+H)$^+$.

b) 2-[N-(Benzyloxycarbonyl)-N-methylaminomethyl]-1-ethyl-1H-indole

NaH (60% dispersion in mineral oil, 0.25 g, 7.1 mmole) was added portionwise, allowing for gas evolution, to a solution of 2-[N-(benzyloxycarbonyl)N-methylaminomethyl]-1H-indole (1.40 g, 4.75 mmole) in DMF (35 mL) at 0° C. When the NaH addition was complete, ethyl iodide (0.42 mL, 5.2 mmole) was added at 0° C. The reaction was stirred at 0° C. for 15 minutes then at RT overnight. The reaction was diluted with water and extracted with ethyl acetate. The combined extracts were dried over $K_2CO_3$ and concentrated to afford the title compound (1.30 g, 87%) as an orange solid: MS (ES) m/e 323 (M+H)$^+$.

e) 1-Ethyl-2-(methylaminomethyl)-1H-indole

2-[N-(benzyloxycarbonyl)-N-methylaminomethyl]-1-ethyl-1H-indole (1.30 g, 4.0 mmole) was added to a suspension of Pearl man's catalyst (about 0.30 g) in MeOH at RT in a Parr flask. The reaction was placed under 50 p.s.i. of $H_2$ and shaken for 8 hr. The mixture was filtered through Celite® and the filter pad was washed with MeOH. The filtrate was concentrated to afford the title compound (0.75 g, 100%) as a light yellow solid: MS (ES) m/e 189 (M+H)$^+$.

Preparation 35

Preparation of 1-methyl-3-(methylaminomethyl)-1H-indole (Method A)

a) Methyl 1-methyl-1H-indole-3-carboxylate

NaH (60% dispersion in mineral oil, 8.56 g, 214.0 mmole) was added portion wise, allowing for gas evolution, to a solution of methyl 1H-indole-3-carboxylate (25.00 g, 142.7 mmole) in DMF (350 mL) at 0° C. When the NaH addition was complete, methyl iodide (44.4 mL, 713.5 mmole) was added at 0° C. The reaction was stirred at 0° C. for 15 minutes then at RT overnight. The reaction was diluted with water and extracted with ethyl acetate. The combined extracts were dried over $K_2CO_3$ and concentrated to afford the title compound (26.00 g, 96%) as an orange solid: MS (ES) m/e 190 (M+H)$^+$.

b) N,1-Dimethyl-1H-indole-3-carboxamide

A suspension of methyl 1-methyl-1H-indole-3-carboxylate (4.30 g, 22.74 mmole) in 40% aqueous $CH_3NH_2$ (400 mL) was stirred at RT. The flask was tightly stoppered to keep the material inside the flask. As the reaction proceeded the product began to precipitate. The reaction was stirred at RT for 3 days, then was concentrated to remove approximately 200 mL of the solvent. The remaining residue was diluted with $H_2O$ (500 mL), and the solid was collected by suction filtration and washed with $H_2O$. Flash chromatography on silica gel (ethyl acetate) gave the title compound (2.4 g, 56%) as a white solid: MS (ES) m/e 189 (M+H)$^+$.

c) 1-Methyl-3-(methylaminomethyl)-1H-indole

A solution of $LiAlH_4$ in THF (1.0 M, 5.20 mL, 5.2 mmole) was slowly added via syringe to a solution of N,1-dimethyl-1H-indole-3-carboxamide (0.50 g, 2.6 mmole) in anhydrous THF (15 mL). Gas was evolved during the addition of the first 2 mL of $LiAlH_4$ solution. When the addition was complete, the resulting light yellow solution was heated at gentle reflux. After 23 hr. the reaction was cooled in ice and quenched by the sequential dropwise addition of $H_2O$ (0.5 mL). 1.0 N NaOH (0.5 mL), and $H_2O$ (0.5 mL). The mixture was stirred for 15 min, then was filtered through Celite®, and the filter pad was washed thoroughly with THF. The filtrate was concentrated and the residue was flash chromatographed on silica gel (10% $MeOH/CHCl_3$ containing 0.5% conc. $NH_4OH$) to afford the title compound (0.30 g, 67%) as a light yellow oil: MS (ES) m/e 175 (M+H)$^+$.

Preparation 36

Preparation of 1-methyl-3-(methylaminomethyl)-1H-indole (Method B)

To a solution of 1-methylindole-3-carboxaldehyde (10.0 g, 62.8 mmole) in MeOH (100 mL) was added a solution of 2.0 M $CH_3NH_2$ in MeOH (126 mL, 252.0 mmole). The reaction was stirred at RT for 2 hrs, then was concentrated to a light yellow oil. This oil was dissolved in EtOH (300 mL), and $NaBH_4$ (2-38 g, 62.8 mmole) was added. After 2 hrs the reaction was concentrated to a slurry and dissolved in 1.0 N NaOH (75 mL). The aqueous solution was extracted with $Et_2O$ (2×200 mL) and the combined organic fractions were dried over $Na_2SO_4$ and concentrated. Flash chromatography on silica gel (9:1 $CHCl_3$/MeOH containing 5% $NH_4OH$) and drying in high vacuum left the title compound (10.1 g, 92%) as a faintly yellow oil: MS (ES) m/e 175 (M+H)$^+$.

Preparation 37

Preparation of (E)-3-(6-aminopyridin-3-yl)-2-methylacrylic acid HCl salt and 2-(6-aminopyridin-3-yl) methyl)acrylic acid HCl salt a) Ethyl (E)-3-(6-aminopyridin-3-yl)-2-methyl)acrylate and ethyl 2-(6-aminopyridin-3-ylmethyl)acrylate To a stirred solution of 2-amino-5-bromopyridine (25 g, 140 mmole) in propionitrile (150 mL) was added ethyl methacrylate (50 mL, 400 mmole), DIEA (50 mL, 287 mmole), palladium(II) acetate (1.57 g, 7 mmole), and tri-o-tolylphosphine (4.3 g, 14 mmole). The reaction was purged with argon and heated at reflux for 6 hr, then was cooled to RT and concentrated to dryness under vacuum. The residue was taken up in 80% ethyl acetate/hexanes (100 mL), and the solution was filtered through a pad of silica gel, eluting with 80% ethyl acetate/hexanes (400 mL) until all the product was eluted off. The yellowish filtrate was concentrated under vacuum, and the residue was taken up in a small volume of 1:1 $Et_2O$/petroleum ether. The precipitate which formed was collected and dried under vacuum to give ethyl (E)-3-(6-aminopyridin-3-yl)-2-methylacrylate (10.77 g, 37%) as a pale yellow solid: LCMS (ES) m/e 207.0 (M+H)$^+$; $^1$H NMR (300 MHz, $CDCl_3$) δ 8.05 (d, J=1.7 Hz, 1H), 7.63 (dd, 1H), 7.48 (s, 1H), 6.75 (d, J=8.8 Hz, 1H), 5.79 (br s, 2H), 4.26 (q, 2H), 2.10 (s, 3H), 1.34 (t, 3H). The filtrate was concentrated to dryness and purified by flash chromatography on silica gel (4:1 ethyl acetate/hexanes) to give additional ethyl (E)-3-(6-aminopyridin-3-yl)-2-methylacrylate (0.87 g, 3%) and ethyl 2-(6-aminopyridin-3-ylmethyl)acrylate (5.77 g, 20%) as a yellow oil: LCMS (ES) m/e 207.0 (M+H)$^+$; $^1$H NMR (300 MHz, $CDCl_3$) 57.86 (d, J=2.1 Hz, 1H), 7.32 (dd, 1H), 6.53 (d, J=8.5 Hz, 1H), 6.21 (d, J=1.8 Hz, 1H), 5.48 (d, J=1.4 Hz, 1H), 4.17 (q, 2H), 3.47 (s, 2H), 1.27 (t, 3H).

b) (E)-3-(6-Aminopyridin-3-yl)-2-methylacrylic acid HCl salt

To ethyl (E)-3-(6-aminopyridin-3-yl)-2-methylacrylate (5.0 g, 24.2 mmole) was added HOAc (25 mL) and conc. HCl (25 mL). Hie reaction was stirred and heated at 100° C. for 6 hr, cooled to RT and concentrated to dryness. The remaining residue was triturated with $Et_2O$, filtered and dried under vacuum to give the title compound (53 g, quantitative) as a white solid: LCMS (ES) m/e 179.0 (M+H)$^+$; $^1$H NMR (300

MHz, DMSO-d$_6$) δ 8.47 (br s, 2H), 8.16 (d, J=1.7 Hz, 1H), 8.08 (dd, 1H), 7.42 (s, 1H), 7.08 (d, J=9.3 Hz, 1H), 2.01 (s, 3H).

c) 2-(6-Aminopyridin-3-ylmethyl)acrylic acid HCl salt

According to the procedure of Preparation 37 (b), except substituting ethyl 2-(6-aminopyridin-3-ylmethyl)acrylate (3.1 g, 15 mmole) for ethyl (E)-3-(6-aminopyridin-3-yl)-2-methylacrylate gave the title compound (3.0 g, 93%) as a white solid: LCMS (ES) m/e 179.0 (M+H)$^+$; $^1$H NMR (300 MHz, DMSO-d$_6$) δ 8.10 (br s, 2H), 7.79 (dd, 1H), 7.78 (s, 1H), 7.00 (d, J=9.7 Hz, 1H), 6.15 (d, J=1.2 Hz, 1H), 5.67 (d, J=1.2 Hz, 1H), 3.45 (s, 2H).

Preparation 38

Preparation of 2-(methylaminomethyl)naphthalene

To a stirred solution of 40 wt % methylamine in H$_2$O (50 mL, 581 mmole) in THF (50 mL) at 0° C. was added 2-(bromomethyl)naphthalene (10 g, 43 mmole) in one portion. The reaction was allowed to warm to RT and stirred for 16 hr, then was then concentrated under vacuum. The residue was taken up in Et$_2$O and washed with 1.0 N NaOH then with brine, dried (Na$_2$SO$_4$), and concentrated to dryness. Purification by flash chromatography on silica gel (98:2 to 9:1 CHCl$_3$/methanol containing 5% NH$_4$OH) gave the title compound (3.95 g, 54%) as a clear oil: $^1$H NMR (400 MHz, CDCl$_3$) δ 7.85 (m, 3H), 7.79 (s, 1H), 7.49 (m, 3H), 3.94 (s, 2H), 2.53 (s, 3H).

Preparation 39

Preparation of (E)-3-(6-amino-4-methylpyridin-3-yl) acrylic acid HCl salt a) 2-Amino-5-bromo-4-methylpyridine

To a stirred solution of 2-amino-4-methylpyridine (22 g, 203 mmole) in 48% HBr (200 mL) at 70° C. was added dropwise a solution of 15% H$_2$O$_2$ in H$_2$O (60 mL) over 60 minutes. The reaction became slightly exothermic and the oil bath was removed after 15 minutes. The reaction stirred for an additional 1 hr, then was poured into ice (approximately 500 mL). The clear solution was adjusted to pH 4-5 with solid Na$_2$CO$_3$ (80 g, 755 mmole), and the resulting thick white suspension was filtered. The filter pad was washed with a small volume of H$_2$O and pressed dry. Drying under high vacuum gave a 2:3 mixture of 2-amino-5-bromo-4-methylpyridine and 2-amino-3,5-dibromo-4-methylpyridine (27.08 g). Flash chromatography on silica gel (50% ethyl acetate/hexanes then ethyl acetate) gave the title compound (12.11 g, 32%) as a white solid: LCMS (ES) m/e 187.2 (M+H)$^+$; $^1$H NMR (400 MHz, DMSO-d$_6$) δ 7.92 (s, 1H), 6.41 (s, 1H), 6.03 (br s, 2H), 2.17 (s, 3H).

b) Ethyl (E)-3-(6-amino-4-methylpyridin-3-yl)acrylate

To a stirred solution of 2-amino-5-bromo-4-methylpyridine (10 g, 54 mmole) in propionitrile (50 mL) was added ethyl acrylate (17 mL, 157 mmole), DIEA (19 mL, 106 mmole), palladium(II) acetate (0.61 g, 2.7 mmole) and tri-o-tolylphosphine (1.64 g, 5.4 mmole). The reaction was purged with argon and heated at reflux for 6 hr, then was cooled to RT and concentrated to dryness under vacuum. The resulting residue was taken up in ethyl acetate and filtered through a pad of silica gel. The filtrate was concentrated and the remaining residue was triturated with 1:1 Et$_2$O/petroleum ether (50 mL), filtered, and dried under vacuum to give the title compound (6.50 g, 59%) as a pale yellow solid: $^1$HNMR (400 MHz, DMSO-d$_6$) δ 8.31 (s, 1H), 7.66 (d, J=16.0 Hz, 1H), 6.40 (br s, 2H), 6.32 (d, J=16.0 Hz, 1H), 6.28 (s, 1H), 4.15 (q, 2H), 2.24 (s, 3H), 1.24 (t, 3H).

c) (E)-3-(6-Amino-4-methylpyridin-3-yl)acrylic acid HCl salt

To ethyl (E)-3-(6-amino-4-methylpyridin-3-yl)acrylate (1.50 g, 7.3 mmole) was added HOAc (15 mL) and conc. HCl (15 mL). The solution was stirred at 100° C. for 10 hr, cooled to RT, and concentrated to dryness. Trituration with Et$_2$O, filtration and drying under vacuum gave the title compound (1.65 g, quantitative) as a white solid: LCMS (ES) m/e 179.2 (M+H)$^+$; $^1$H NMR (400 MHz, DMSO-d$_6$) δ 8.37 (s, 1H), 8.28 (br s, 3H), 7.51 (d, J=16.0 Hz, 1H), 6.86 (s, 1H), 6.46 (d, J=16.0 Hz, 1H), 2.41 (s, 3H).

Preparation 40

Preparation of 1,3-dimethyl-2-(methylaminomethyl)-1H-indole a) 1,3-Dimethyl-1H-indole

To a stirred solution of 3-methylindole (15.0 g, 114 mmole) in dry DMF (200 mL) was added NaH (60% dispersion in oil, 5.0 g, 125 mmole) in portions. Gas evolution was observed. The mixture was stirred for 30 min, then iodomethane (8 mL, 129 mmole) was added in one portion. The reaction became exothermic and was cooled in an ice bath. After 16 hr at RT, the reaction was concentrated under vacuum and the residue was taken up in ethyl acetate. The solution was washed with H$_2$O then with brine, dried (MgSO$_4$), and concentrated to dryness. Purification by short path distillation under vacuum (bp 88-92° C., 05 mmHg) gave the title compound (16.10 g, 97%) as a pale yellow oil: $^1$H NMR (400 MHz, CDCl$_3$) δ 7.47 (d, J=7.9 Hz, 1H), 7.35 (d, J=8.2 Hz, 1H), 7.13 (t, 1H), 7.06 (s, 1H), 7.00 (t, 1H), 3.71 (s, 3H), 2.24 (s, 3H).

b) 1,3-Dimethyl-1H-indole-2-carboxaldehyde

To a stirred solution of phosphorus oxychloride (7.0 mL, 75 mmole) in DMF (25 mL) was added dropwise a solution of 1,3-dimethylindole (12.0 g, 83 mmole) in dry DMF (6.0 mL). The reaction was stirred at RT for 2 hr then was poured onto ice. The mixture was basified with a solution of NaOH (13.2 g, 330 mmole) in H$_2$O (44 mL), then was extracted with Et$_2$O (2×50 mL). The combined organic layers were washed with brine, dried (MgSO$_4$), and concentrated under vacuum. Flash chromatography on silica gel (10% ethyl acetate/hexanes) gave the title compound (13.03 g, 91%) as an off-white solid: LCMS (ES) m/e 174.2 (M+H)$^+$; $^1$H NMR (400 MHz, CDCl$_3$) δ 10.16 (s, 1H), 7.68 (d, J=8.1 Hz, 1H), 7.42 (t, 1H), 7.32 (d, J=8.5 Hz, 1H), 7.15 (t, 1H), 4.04 (s, 3H), 2.63 (s, 3H).

c) 1,3-Dimethyl-2-(methylaminomethyl-1H-indole

To 1,3-dimethyl-1H-indole-2-carboxaldehyde (13.0 g, 75 mmole) was added a solution of 2.0 M methylamine in methanol (150 mL, 300 mmole) and HOAc (4.3 mL, 75 mmole). The solution was stirred at RT for 4 hr, then was cooled to 0° C., and sodium cyanoborohydride (5.0 g, 80 mmole) was added portionwise over 5 min. The reaction was then allowed to warm to RT. After 16 hr, the reaction was concentrated under vacuum and the residue was taken up in $Et_2O$. The solution was washed with 1.0 N NaOH then with brine, dried ($Na_2SO_4$), and concentrated to dryness. Flash chromatography on silica gel (95:5 $CHCl_3$/methanol containing 5% $NH_4OH$) gave the title compound (7.34 g, 52%) as a yellow oil. $^1H$ NMR (400 MHz, $CDCl_3$) δ 7.53 (d, J=7.8 Hz, 1H), 7.26 (d, J=7.8 Hz, 1H), 7.20 (t, 1H), 7.09 (t, 1H), 3.88 (s, 2H), 3.76 (s, 3H), 2.46 (s, 3H), 2.32 (s, 3H), 1.36 (br s, 1H).

Preparation 41

Preparation of 6-bromo-2-oxo-1,4-dihydro-2H-pyrido[2,3-d]-1,3-oxazine a) 2-Amino-3-(hydroxymethyl)pyridine To a stirred solution of 2-aminonicotinic acid (20 g, 145 mmole) in dry THF (200 mL) under argon was added 1.0 $LiAlH_4$ in THF (300 mL, 300 mmole) carefully, portionwise, through a reflux condenser, over 4 hr. The reaction became exothermic and refluxed without external heating. After the addition was complete, the reaction was heated at reflux for an additional 16 hr, then was cooled to 0° C. and carefully quenched by sequential addition of $H_2O$ (12 mL), 15% NaOH in $H_2O$ (12 mL), and $H_2O$ (35 mL). The resulting thick suspension was stirred for 1 hr, then was filtered through a pad of Celite®. The filter pad was rinsed with THF (300 mL), and the filtrate was concentrated to dryness to give the title compound (17.04 g, 95%) as a pale yellow waxy solid: LCMS (ES) m/e 125.1 $(M+H)^+$; $^1H$ NMR (400 MHz, DMSO-$d_6$) δ 7.84 (dd, 1H), 7.37 (m, 1H), 6.53 (dd, 1H), 5.65 (br s, 2H), 5.16 (t, 1H), 4.34 (d, J=4.6 Hz, 2H).

b) 2-Amino-5-bromo-3-(hydroxymethyl)pyridine

To a stirred solution of 2-amino-3-(hydroxymethyl)pyridine (15.0 g, 121 mmole) in HOAc (300 mL) at RT was added bromine (6.2 mL, 121 mmole) dropwise over 1 hr. A suspension formed after approximately 15 min. After the addition, the reaction was stirred for an additional 1 hr, then was concentrated under vacuum. The residue was taken up in 1.0 M $Na_2CO_3$ (500 mL), and the solution was extracted with ethyl acetate (2×250 mL). The combined organic layers were washed with brine, dried ($Na_2SO_4$), and concentrated to dryness. The resulting residue was triturated with a small volume of petroleum ether, filtered and dried under vacuum to give the title compound (18.45 g, 75%) as a beige solid: LCMS (ES) m/e 203.2 $(M+H)^+$; $^1H$ NMR (400 MHz, DMSO-$d_6$) δ 7.89 (d, J=2.3 Hz, 1H), 7.52 (s, 1H), 5.92 (br s, 2H), 5.29 (br s, 1H), 4.30 (s, 2H).

c) 6-Bromo-2-oxo-1,4-dihydro-2H-pyrido[2,3-d]-1,3-oxazine

To a stirred solution of 2-amino-5-bromo-3-(hydroxymethyl)pyridine (3.0 g, 15 mmole) in methanol (30 mL) was added dimethyl carbonate (5 mL, 60 mmole) and sodium methoxide (25 wt % solution in methanol, 4 mL, 17.4 mmole). The reaction was heated at reflux for 18 hr, cooled to RT, and concentrated to dryness. The remaining residue was triturated with saturated aqueous $NH_4Cl$ (50 mL), filtered, washed with cold $H_2O$ (50 mL), and dried under vacuum to give the title compound (1.75 g, 51%) as a beige solid: LCMS (ES) m/e 229.0 $(M+H)^+$; $^1H$ NMR (400 MHz, DMSO-$d_6$) δ 10.90 (s, 1H), 8.31 (s, 1H), 7.90 (s, 1H), 5.31 (s, 2H).

Preparation 42

Preparation of 3-methyl-2-(methylaminomethyl)benzo[b]thiophene

To a stirred solution of 3-methylbenzo[b]thiophene-2-carboxaldehyde (0.5 g, 2.8 mmole) in methanol (15 mL) was added 2.0 M methylamine in methanol (6 mL, 12 mmole) and HOAc (0.32 mL, 5.7 mmole). The reaction was stirred at RT for hr, then sodium cyanoborohydride (0.2 g, 3 mmole) was added in one portion. After stirring for an additional 16 hr the reaction was concentrated to dryness. The residue was taken up in $Et_2O$ and washed with 1.0 N NaOH then with brine, dried ($Na_2SO_4$), and concentrated under vacuum. Purification by flash chromatography on silica gel (95:5 $CHCl_3$/methanol containing 5% $NH_4OH$) gave the title compound (0.30 g, 56%) as a yellow oil: $^1H$ NMR (400 MHz, $CDCl_3$) δ 7.77 (d, J=7.8 Hz, 1H), 7.62 (d, J=7.9 Hz, 1H), 7.34 (t, 1H), 7.28 (t, 1H), 3.99 (s, 2H), 2.49 (s, 3H), 2.34 (s, 3H), 1.77 (br s, 1H).

Preparation 43

Preparation of 2-methylaminomethyl)benzothiophene a) N-methyl benzothiophene-2-carboxamide To a stirred solution of 2.0 M methylamine in THF (60 mL) and THF (60 mL) was added dropwise at 0° C. a solution of benzothiophene-2-carbonyl chloride (10.8 g, 55 mmole) in THF (50 mL) over 15 minutes. After the addition the reaction was allowed to warm to RT then was concentrated under vacuum. Trituration with a cold solution of 4:1 $H_2O$/methanol (50 mL), filtration, and drying under vacuum gave the title compound (10.35 g, 98%) as a white solid: MS (ES) m/e 191.9 $(M+H)^+$.

b) 2-(Methylaminomethyl)benzothiophene

To a stirred suspension of N-methyl benzothiophene-2-carboxamide (10.0 g, 52 mmole) in dry THF (75 mL) under argon was added a solution of 1.0 M $LiAlH_4$ in THF (135 mL, 135 mmole) over 15 minutes. The reaction quickly became clear and was heated at reflux for 2 days. After cooling to 0° C. the reaction was carefully quenched with the sequential addition of $H_2O$ (5.1 mL), 15% NaOH in $H_2O$ (5.1 mL), and $H_2O$ (15.3 mL). The mixture was filtered through a pad of Celite® and the filter pad was rinsed with $Et_2O$ (50 mL). The filtrate was concentrated to afford the title compound (9.11 g, 99%) as a pale yellow oil which solidified in the freezer $^1H$ NMR (400 MHz, $CDCl_3$) δ 7.83 (d, J=7.3 Hz, 1H), 7.72 (d, J=7.3 Hz, 1H), 7.33 (m, 2H), 7.17 (s, 1H), 4.06 (s, 2H), 2.53 (s, 3H), 1.56 (br s, 1H).

Preparation 44

Preparation of 2-methyl-3-(methylaminomethyl)indole

To a solution of 2-methylindole-3-carboxaldehyde (10.00 g, 62.84 mmole) in MeOH (100 mL) was added 2 M $CH_3NH_2$ in MeOH (200 mL). After stirring for 3 hours at RT, the reaction solution was concentrated to a yellow oil which solidified under vacuum. This solid was dissolved in ethanol (350 mL) and NaBH$_4$ (2.38 g, 62.8 mmole) was added. The reaction was stirred at RT for 6 hours, then was concentrated under vacuum. The remaining residue was diluted with saturated aqueous Na$_2$CO$_3$ (50 mL) and extracted with EtOAc (2×200 mL). The organic phase was separated, washed with brine, and dried over Na$_2$SO$_4$. Flash chromatography on silica gel (9:1 CHCl$_3$/MeOH containing 5% NH$_4$OH) and drying under high vacuum gave the title compound (6.88 g, 63%) as a faintly yellow viscous solid: MS (ES) m/e 175 (M+H)$^+$.

Preparation 45

Preparation of 5-bromo-2H-pyrido[3,2-b]-1,4-oxazin-3(4H)-one

To a solution of 2H-pyrido[3,2-b]-1,4-oxazin-3(4H)-one (5.00 g, 33.3 mmole) in HOAc (100 mL) was added Br$_2$ (2.6 mL, 50.0 mmole). After stirring for 48 hours at RT, the reaction solution was concentrated to an orange solid, which was suspended in 1N NaOH (50 mL) and extracted with EtOAc (2×100 mL). The combined organic layers were washed with brine and dried over Na$_2$SO$_4$. Flash chromatography on silica gel (9:1 CHCl$_3$/MeOH containing 5% NH$_4$OH) and drying under high vacuum gave the title compound (5.49 g, 72%) as a yellow solid: MS (ES) m/e 230 (M+H)$^+$.

Preparation 46

Preparation of 5-bromo-2-acetylaminopyrimidine

To a solution of 5-bromo-2-aminopyrimidine (2.0 g, 11.5 mmole) in CH$_2$Cl$_2$ (75 mL) at RT was added 2,6-lutidine (2.7 mL, 23.0 mmole) followed by acetyl chloride (0.99 g, 12.6 mmole). After stirring for 8 hours, the reaction solution was concentrated under vacuum. The remaining residue was dissolved EtOAc (200 mL), washed with H$_2$O (100 mL) and brine, and dried over Na$_2$SO$_4$. Flash chromatography on silica gel (95:5 CHCl$_3$/MeOH) and drying under high vacuum gave the title compound (1.74 g, 70%) as a yellow solid: MS (ES) m/e 217 (M+H)$^+$.

Preparation 47

Preparation of 1-methyl-2-(methylamino methyl)-6-methoxy-1H-indole a) Methyl-1-methyl-6-methoxy-1H-indole-2-carboxylate According to the procedure of Preparation 1 (a), except substituting methyl-6-methoxyindole-2-carboxylate for ethyl indole-2-carboxylate, the title compound (90%) was prepared as a tan solid: MS (ES) m/e 220.2 (M+H)$^+$ b) N,1-Dimethyl-6-methoxy-1H-indole-2-carboxamide According to the procedure of Preparation 1 (b), except substituting methyl-1-methyl-6-methoxy-1H-indole-2-carboxylate for ethyl-1-methyl-1H-indole-2-carboxylate, the title compound (95%) was prepared as an off-white solid: MS (ES) m/e 219.2 (M+H)$^+$ and 437.4 (2M+H)$^+$.

c) 1-Methyl-2-(methylamino methyl)-6-methoxy-1H-indole

According to the procedure of Preparation I (c), except substituting N,1-dimethyl-6-methoxy-1H-indole-2-carboxamide for N,1-dimethyl-1H-indole-2-carboxamide, the title compound (76%) was prepared as a light gray solid: MS (ES) m/e 205.2 (M+H)$^+$, 409.4 (2M+H)$^+$.

Preparation 48

Preparation of 1,7-dimethyl-3-(methylaminomethyl)-1H-indole a) 1,7-Dimethyl-1H-indole According to the procedure of Preparation 1 (a), except substituting 7-methylindole for ethyl indole-2-carboxylate, the title compound (89%) was prepared as a tan solid: MS (ES) m/e 146.2 (M+H)$^+$.

b) 1,7-Dimethyl-1H-indole-3-carboxaldehyde

According to the procedure of Preparation 40 (b), except substituting 1,7-dimethyl-1H-indole for 1,3-dimethylindole, the title compound (82%) was prepared as a light tan solid: MS (ES) m/e 174.2 (M+H)$^+$.

c) 1,7-Dimethyl-3-(methylaminomethyl)-1H-indole

According to the procedure of Preparation 40 (c), except substituting 1,7-dimethyl-1H-indole-3-carboxaldehyde for 1,3-dimethyl-1H-indole-1-carboxaldehyde, the title compound (98%) was prepared as a white, crystalline solid: MS (ES) m/e 189.2 (M+H)$^+$.

Preparation 49

Preparation of 1,5-dimethyl-3-(methylaminomethyl)-1H-indole a) 1,5-Dimethyl-1H-indole According to the method of Preparation 1 (a), except substituting 5-methylindole for ethyl indole-2-carboxylate, the title compound (92%) was prepared as an amber oil: MS (ES) m/e 146.2 (M+H)$^+$.

b) 1,5-Dimethyl-1H-indole-3-carboxaldehyde

According to the procedure of Preparation 40 (b), except substituting 1,5-dimethyl-1H-indole for 1,3-dimethylindole, the title compound (82%) was prepared as a light tan solid: MS (ES) m/e 174.2 (M+H)$^+$ c) 1,5-Dimethyl-3-(methylaminomethyl)-1H-indole According to the procedure of Preparation 36, except substituting 1,5-dimethyl-1H-indole-3-carboxaldehyde for 1,3-dimethyl-1H-indole-1-carboxaldehyde, the title compound (89%) was prepared as an oil: MS (ES) m/e 189.2 (M+H)$^+$.

Preparation 50

Preparation of 1,6-dimethyl-3-(methylaminomethyl)-1H-indole a) 1,6-Dimethyl-1H-indole According to the procedure of Preparation 1 (a), except substituting 5-methylindole for ethyl indole-2-carboxylate, the title compound (96%) was prepared as an amber oil: MS (ES) m/e 146.2 (M+H)$^+$.

b) 1,6-Dimethyl-1H-indole-3-carboxaldehyde

According to the procedure of Preparation 40 (b), except substituting 1,5-dimethyl-1H-indole for 1,3-dimethylindole, the title compound (99%) was prepared as a light tan solid: MS (ES) m/e 174.2 (M+H)$^+$.

c) 1,6-Dimethyl-3-(methylaminomethyl)-1H-indole

According to the procedure of Preparation 36, except substituting 1,5-dimethyl-1H-indole-3-carboxaldehyde for 1,3-dimethyl-1H-indole-1-carboxaldehyde, the title compound (95%) was prepared as an oil: MS (ES) m/e 189.2 (M+H)$^+$.

Preparation 51

Preparation of 1-benzyl-3-methylaminomethyl)-1H-indole a) 3-(Methylaminomethyl)-1H-indole

To a solution of indole-3-carboxaldehyde (5.4 g, 34.1 mmole) in MeOH (30 mL) was added a solution of 2.0 M CH$_3$NH$_2$ m MeOH (51.3 mL, 102.6 mmole). The reaction was stirred at RT overnight, then was concentrated to a light yellow oil. This oil was dissolved in EtOH (40 mL), and NaBH$_4$ (1.3 g, 34.1 mmole) was added. After 16 hrs the reaction was concentrated to a slurry and dissolved in 10% Na$_2$CO$_3$ (100 mL). The aqueous solution was extracted with EtOAc (2×200 mL) and the combined organic fractions were dried over Na$_2$SO$_4$ and concentrated. Drying in high vacuum left the title compound (5.2 g, 94%) as a faintly yellow oil: MS (ES) m/e 161 (M+H)$^+$.

b) 3-[N-(Benzyloxycarbonyl)-N-methylaminomethyl]-1H-indole

N-(Benzyloxycarbonyloxy)succinimide (8.9 g, 35.7 mmole) was added to a solution of 3-(methylaminomethyl)-1H-indole (5.2 g, 32.5 mmole) and triethylamine (5.0 mL, 65.7 mmole) in DMF (100 mL) at RT. The reaction was stirred overnight then was concentrated in vacuo. The residue was diluted with water and the mixture was extracted with ethyl acetate. The combined extracts were dried over Na$_2$SO$_4$ and concentrated. Flash chromatography on silica gel (33% ethyl acetate/hexanes) gave the title compound (7.0 g, 74%) as an off-white solid: MS (ES) m/e 295 (M+H)$^+$.

c) 3-[N-(Benzyloxycarbonyl)-N-methylaminomethyl]-1-benzyl-1H-indole

NaH (60% dispersion in mineral oil, 0.15 g, 3.8 mmole) was added portionwise, allowing for gas evolution, to a solution of 3-[N-(benzyloxycarbonyl)-N-methylaminomethyl]-1H-indole (0.7 g, 2.5 mmole) in DMF (25 mL) at 0° C. When the NaH addition was complete, benzyl bromide (1.2 mL, 10.0 mmole) was added at 0° C. The reaction was stirred at 0° C. for 15 minutes then at RT overnight. The reaction was diluted with water and extracted with ethyl acetate. The combined extracts were dried over Na$_2$SO$_4$ and concentrated. Flash chromatography on silica gel (33% ethyl acetate/hexanes) gave the title compound (0.9 g, 93%) as an off white solid: MS (ES) m/e 385 (M+H)$^+$.

d) 1-Benzyl-3-(methylaminomethyl)-1H-indole

3-[N-(Benzyloxycarbonyl)-N-methylaminomethyl]-1-benzyl-1H-indole (0.9 g, 2.3 mmole) was added to a suspension of Pearlman's catalyst (about 0.30 g) in MeOH at RT in a Parr flask. The reaction was placed under 50 p.s.i. of H$_2$ and shaken for 5 hr. The mixture was filtered through Celite® and the filter pad was washed with MeOH. The filtrate was concentrated to afford the title compound (0.5 g, 86%) as a light yellow solid: MS (ES) m/e 251 (M+H)$^+$.

Preparation 52

Preparation of 2-phenylamino-3-bromopyridine

A mixture of 2,5-dibromopyridine (10.2 g, 43 mmole) in aniline (25 mL) was stirred and heated at reflux for 3 h. The reaction was cooled to RT and most of the aniline was distilled off under vacuum. The remaining residue was taken up in ethyl acetate and the solution was washed with 1.0 N Na$_2$CO$_3$ then with brine, dried (Na$_2$SO$_4$), and concentrated under vacuum. Trituration with petroleum ether, filtration and drying under vacuum gave the ride compound (7.20 g, 67%) as a tan solid: $^1$H NMR (400 MHz, CDCl$_3$) δ 8.25 (d, J=2.4 Hz, 1H), 7.58 (dd, 1H), 7.31-7.39 (m, 4H), 7.11 (m, 1H), 6.79 (br s, 1H); MS (ES) m/e 249.0 (M+H)$^+$.

Preparation 53

Preparation of 1,2-dimethyl-3-(methylaminomethyl)-1H-indole a) 1,2-Dimethylindole-3-carboxaldehyde

A solution of POCl$_3$ (7.0 mL, 75 mmole) in DMF (100 mL) was stirred for 5 minutes at 0° C., then 1,2-dimethylindole (10.0 g, 69 mmole) was added in one portion. The reaction was allowed to warm to RT and stirred for 4 h. The thick slurry was poured into ice water (300 mL) and the flask was rinsed with additional water (50 mL). The aqueous mixture was basified with a solution of NaOH (13.2 g, 330 mmole) in H$_2$O (50 mL), and the thick suspension was filtered to collect the solid. This was washed with water and dried under vacuum to give the title compound (11.59 g, 97%) as an off-white solid: $^1$H NMR (400 MHz, CDCl$_3$) δ 10.07 (s, 1H), 8.09 (d, J=7.9 Hz, 1H), 7.54 (d, J=7.6 Hz, 1H), 7.21 (dt, 2H), 3.73 (s, 3H), 2.70 (s, 3H).

b) 1,2-Dimethyl-3-(methyliminomethyl)-1H-indole

To 1,2-dimethylindole-3-carboxaldehyde (11.50 g, 66.4 mmole) was added a solution of 2 M methylamine in methanol (100 mL, 200 mmole). The reaction was stirred for 4 h at RT then was concentrated to dryness to afford the crude title compound: $^1$H NMR (400 MHz, CDCl$_3$) δ 8.55 (d, J=1.4 Hz, 1H), 8.16 (d, J=7.5 Hz, 1H), 7.42 (d, J=7.8 Hz, 1H), 7.15 (t, 1H), 7.07 (t, 1H), 3.68 (s, 3H), 3.41 (s, 3H), 2.55 (s, 3H).

c) 1,2-Dimethyl-3-(methylaminomethyl)-1H-indole 1,2-Dimethyl-3-(methyliminomethyl)-1H-indole was taken up in ethanol (200 mL) and NaBH$_4$ (2.6 g, 68.7 mmole) was added portionwise with stirring at RT (vigorous gas evolution). After 16 h the reaction was concentrated under vacuum, and the residue was basified with aqueous 1.0 N NaOH (200 mL). The mixture was extracted with Et$_2$O (250 mL), and the combined Et$_2$O extracts were washed with brine, dried (Na$_2$SO$_4$) and concentrated. Purification by flash chromatography on silica gel (5-10% (5% NH$_4$OH/MeOH)/CHCl$_3$) gave the title compound (8.47 g, 68%) as an oil which solidified in the freezer $^1$H NMR (400 MHz, CDCl$_3$) δ 7.60

(d, J=7.7 Hz, 1H), 7.29 (d, J=8.0 Hz, 1H), 7.19 (t, 1H), 7.12 (t, 1H), 3.93 (s, 2H), 3.69 (s, 3H), 2.49 (s, 3H), 2.45 (s, 3H).

Preparation 54

Preparation of 3-(methylaminomethyl)benzo[b]thiophene

To a stirred solution of 2 M methylamine in methanol (75 mmole, 150 mmole) was added benzo[b]thiophen-3-carboxaldehyde (5.3 g, 33 mmole) and HOAc (43 mL, 75 mmole). The reaction was stirred at RT for 1 h, then NaBH$_3$CN (2.1 g, 33 mmole) was added portionwise over 5 minutes. The reaction was stirred for an additional 16 h then was concentrated under vacuum. The residue was taken up in Et$_2$O (300 mL) and washed with 1.0 N NaOH (300 mL) then with brine, dried (Na$_2$SO$_4$), and concentrated. Purification by flash chromatography on silica gel (5% (5% NH$_4$OH/MeOH)/CHCl$_3$) gave the title compound (2.81 g, 48%) as a brownish oil: $^1$H NMR (400 MHz, CDCl$_3$) δ 7.87 (2d, 2H), 7.40 (m, 2H), 7.32 (s, 1H), 4.02 (s, 2H), 2.56 (s, 3H), 1.5 (br s, 1H).

Preparation 55

Preparation of 5-bromo-2,2'-dipyridylamine

Bromine (3.0 mL, 58.2 mmole) was added dropwise over 15 minutes to a stirred solution of 2,2'-dipyridylamine (10 g, 58.4 mmole) in HOAc (100 mL). The reaction quickly became a thick suspension. After 2 h the reaction was concentrated under vacuum and the residue was purified by flash chromatography on silica gel (03% (5% NH$_4$OH/MeOH)/CHCl$_3$). The resulting residue was triturated with hexane and dried under vacuum gave the title product (1.77 g, 12%) as an off-white solid: $^1$H NMR (400 MHz, CDCl$_3$) δ 9.88 (s, 1H), 8.31 (s, 1H), 8.23 (d, J=4.8 Hz, 1H), 7.83 (m, 2H), 7.67 (t, 1H), 7.62 (d, J=8.4 Hz, 1H), 6.90 (t, 1H); MS (ES) m/e 250.0 (M+H)$^+$, 5,5'-dibromo-2,2'-dipyridylamine (4.04 g, 21%) was also isolated as a white solid after trituration with hexane and drying under vacuum: $^1$H NMR (400 MHz, CDCl$_3$) δ 10.08 (s, 1H), 8.32 (d, J=2.5 Hz, 2H), 7.88 (dd, 2H), 7.68 (d, J=9.0 Hz, 2H); MS (ES) m/e 328.0 (M+H)$^+$.

Preparation 56

Preparation of 2-(methylaminomethyl)-3-methylbenzo[b]thiophene

According to the procedures of Preparation 53 (b) and (c), except substituting 3-methylbenzo[b]thiophene-2-carboxaldehyde (7.40 g, 42 mmole) for 1,2-dimethylindole-3-carboxaldehyde, the title compound (6.02 g, 75%) was prepared as a pale yellow oil which solidified in the freezer $^1$H NMR (400 MHz, CDCl$_3$) δ 7.77 (d, J=7.8 Hz, 1H), 7.62 (d, J=7.9 Hz, 1H), 7.34 (t, 1H), 7.28 (t, 1H), 3.99 (s, 2H), 2.49 (s, 3H), 2.34 (s, 3H), 1.77 (br s, 1H).

Preparation 57

Preparation of 2-methyl-3-(methylaminomethyl)benzo[b]thiophene a) 2-Methylbenzo[b]thiophene-3-carboxaldehyde SnCl$_4$ (20 mL, 67 mmole) was added over 5 min to a stirred solution of 2-methylbenzo[b]thiophene (5.0 g, 33.7 mmole) in CH$_2$Cl$_2$ (75 mL) at 0° C. under argon. After 15 minutes, dichloromethyl methyl ether (3.7 mL, 41 mmole) was added. The reaction became a yellowish colored suspension. The reaction was allowed to warm to RT and stirred for 16 h, then was poured onto ice water (200 mL). The aqueous mixture was acidified with 1.0 N HCl (100 mL) and stirred until the suspension dissolved. The organic phase was separated, dried (MgSO$_4$), and concentrated under vacuum. Purification by flash chromatography on silica gel (10% ethyl acetate/hexane) gave the title compound (5.83 g, 98%) as a white crystalline solid: $^1$H NMR (400 MHz, CDCl$_3$) δ 10.38 (s, 1H), 8.61 (d, J=8.1 Hz, 1H), 7.77 (d, J=8.0 Hz, 1H), 7.48 (t, 1H), 7.39 (t, 1H), 2.93 (s, 3H).

b)
2-Methyl-3-(methylaminomethyl)benzo[b]thiophene

According to the procedures of Preparation 53 (b) and (c), except substituting 2-methylbenzo[b]thiophene-3-carboxaldehyde (5.0 g, 28.4 mmole) for 1,2-dimethylindole-3-carboxaldehyde, the title compound (4.89 g, 90%) was prepared as an oil which solidified in the freezer: 1H NMR (400 MHz, CDCl$_3$) δ 7.78 (d, J=7.9 Hz, 1H), 7.75 (d, J=7.9 Hz, 1H), 7.37 (t, 1H), 7.29 (t, 1H), 3.95 (s, 2H), 2.60 (s, 3H), 2.50 (s, 3H).

Preparation 58

Preparation of 3,4-dimethyl-2-(methylaminomethyl)thieno[2,3-b]thiophene

According to the procedure of Preparation 24 (a), except substituting 3,4-dimethylthieno[2,3-b]thiophene-2-carboxaldehyde (0.5 g, 2.5 mmole) for the 1-methylindole-2-carboxaldehyde, the title compound (0.28 g, 53%) was prepared as a colorless oil: MS (ES) m/e 212 (M+H)$^+$.

Preparation 59

Preparation of 1-methyl-2-(methylaminomethyl)naphthalene a) N,1-Dimethylnaphthalene-2-carboxamide According to the procedure of Preparation 20 (a), except substituting 1-methylnaphthalene-2-carboxylic acid (J. Org. Chem. 1965, 22, 3869; 0.3 g, 1.6 mmole) for the 3-methyl-2-inden-2-carboxylic acid, the title compound (0.3 g, 94%) was prepared as a white solid: MS (ES) m/e 200 (M+H)$^+$.

b) 1-Methyl-2-(methylaminomethyl)naphthalene

According to the procedure of Preparation 20 (b), except substituting N,1-dimethylnaphthalene-2-carboxamide (0.3 g, 1.5 mmole) for the N,3-dimethylindene-2-carboxamide, the title compound (0.1 g, 36%) was prepared as a colorless oil: MS (ES) m/e 186 (M+H)$^+$.

Preparation 60

Preparation of 1-methyl-3-methylaminomethyl)-1H-pyrrolo[2,3-b]pyridine a) 1-Methyl-1H-pyrrolo[2,3-b]pyridine According to the procedure of Preparation 40 (a), except substituting 7-azaindole (2.28 g, 1.83 mmole) for the 3-methylindole, the title compound (1.4 g, 58%) was prepared as a yellow oil: MS (ES) m/e 133 (M+H)⁺.

b) 1-Methyl-1H-pyrrolo[2,3-b]pyridine-3-carboxaldehyde

According to the procedure of Preparation 40 (b), except substituting 1-methyl-1H-pyrrolo[2,3-b]pyridine (0.7 g, 5.3 mmole) for the 1,3-dimethylindole, the title compound (0.4 g, 47%) was prepared as a white solid: MS (ES) m/e 161 $(M+H)^+$.

c) 1-Methyl-3-(methylaminomethyl)-pyrrolo[2,3-b]pyridine

According to the procedure of Preparation 40 (c), except substituting 1-methyl-1H-pyrrolo[2,3-b]pyridine-3-carboxaldehyde (0.4 g, 2.5 mmole) for the 1,3-dimethyl-1H-indole-2-carboxaldehyde, the title compound (0.2 g, 45%) was prepared as a yellow oil: MS (ES) m/e 176 $(M+H)^+$.

Preparation 61

Preparation of 2,3-dihydro-8-(methylaminomethyl)-1H-3a-azacyclopenta[a]indene a) 2,3-Dihydro-1H-3a-azacyclopenta[a]indene-8-carboxaldehyde

According to the procedure of Preparation 40 (b), except substituting 2,3-dihydro-1H-3a-azacyclopenta[a]indene (*J. Med. Chem.* 1965, 8, 700; 0.24 g, 1.53 mmole) for the 1,3-dimethylindole, the title compound (0.17 g, 60%) was prepared as a yellow solid: MS (ES)/n/c 186 $(M+H)^+$.

b) 2,3-Dihydro-8-(methylaminomethyl)-1H-3a-azacyclopenta[a]indene

According to the procedure of Preparation 40 (c), except substituting 2,3-dihydro-1H-3a-azacyclopenta[a]indene-8-carboxaldehyde (0.17 g, 0.92 mmole) for the 1,3-dimethyl-1H-indole-2-carboxaldehyde, the title compound (0.1 g, 54%) was prepared as a yellow oil: MS (ES) m/e 201 $(M+H)^+$.

The following examples illustrate methods for preparing the biologically active compounds of this invention from intermediate compounds such as those described in the foregoing Preparations.

Example 1

Preparation of (E)-3-(6-aminopyridin-3-yl)-N-methyl-N-(1-methyl-1H-indol-2-ylmethyl)acrylamide EDC (0.70 g, 3.7 mmole) was added to a solution of (E)-3-(6-aminopyridin-3-yl)acrylic acid (0.61 g, 3.7 mmole), 1-methyl-2-(methylaminomethyl)-1H-indole (0.65 g, 3.7 mmole), HOBt.H₂O (0.50 g, 3.7 mmole), and triethylamine (0.52 mL, 3.7 mmole) in DMF (30 mL) at RT. The reaction was stirred overnight, then was concentrated in vacuo. The residue was diluted with 5% NaHCO₃ and extracted with CH₂Cl₂. The combined organic extracts were washed with brine and dried over MgSO₄. Flash chromatography on silica gel (3% MeOH/CH₂Cl₂) gave a colorless semisolid which was triturated with Et₂O and dried. The title compound (1.0 g, 83%) was obtained as a white solid: ¹H NMR (300 MHz, CDCl₃) δ 8.20 (br s, 1H), 7.45-7.70 (m, 3H), 7.00-7.30 (m, 3H), 6.69 (d, J=15.4 Hz, 1H), 6.30-6.50 (m, 2H), 4.89 (s, 2H), 4.67 (br s, 2H), 3.68 (s, 3H), 3.01 (s, 3H); MS (ES) m/e 321 $(M+H)^+$. Anal. Calcd for C₁₉H₂₀N₄O—0.40 H₂O: C, 69.66; H, 6.40; N, 17.10. Found: C, 69.99; H, 6.27; N, 16.84.

Example 2

Preparation of (E)-3-(4-aminophenyl)-N-methyl-N-d-methyl-1H-indol-2-ylmethyl)acrylamide EDC (218 mg, 1.14 mmole) was added to a solution of 4-aminocinnamic acid hydrochloride (220 mg, 1.10 mmole), 1-methyl-2-(methylaminomethyl)-1H-indole (0.20 g, 1.15 mmole), HOBt.H₂O (154 mg, 1.14 mmole), and triethylamine (0.20 mL, 1.43 mmole) in DMF (20 mL) at RT. The reaction was stirred overnight, then was concentrated in vacuo. The residue was diluted with 5% NaHCO₃ and extracted with CH₂Cl₂. The combined organic extracts were washed with brine (2×30 mL) and dried over MgSO₄. Flash chromatography on silica gel (3% MeOH/CH₂Cl₂) gave the title compound (68 mg, 19%) as a yellow foam: ¹H NMR (360 MHz, DMSO-d₈, 330 K) δ 7.46 (d, J=7.8 Hz, 1H), 7.42 (d, J=15.3 Hz, 1H), 7.37 (d, J=8.3 Hz, 1H), 7.32 (d, J=8.5 Hz, 2H), 7.06-7.15 (m, 1H), 6.94-7.03 (m, 1H), 6.81 (d, J=15.3 Hz, 1H), 638 (d, J=8.5 Hz, 2H), 6.33 (s, 1H), 5.25 (br s, 2H), 4.85 (s, 2H), 3-70 (s, 3H), 3.02 (s, 3H); MS (ES) m/e 320 $(M+H)^+$. Anal. Calcd for C₂₀H₂₁N₃O.0.20 H₂O: C, 74.37; H, 6.68; N, 13.01. Found: C, 74.21; H, 6.60; N, 12.80.

Example 3

Preparation of (E)-N-Methyl-N-(1-methyl-1H-indol-2-ylmethyl)-3-(pyridin-3-yl)acrylamide EDC (0.22 g, 1.14 mmole) was added to a solution of trans-3-(3-pyridyl)acrylic acid (0.17 g, 1.14 mmole), 1-methyl-2-(methylaminomethyl)-1H-indole (0.20 g, 1.15 mmole), and HOBt.H₂O (0.15 g, 1.11 mmole) in DMF (10 mL) at RT. The reaction was stirred overnight, then was concentrated in vacuo. The residue was diluted with 5% NaHCO₃ and extracted with CH₂Cl₂. The combined organic extracts were washed with brine and dried over MgSO₄. Flash chromatography on silica gel (3% MeOH/CH₂Cl₂) followed by preparative TLC (3% MeOH/CH₂Cl₂) gave the title compound (0.14 g, 40%) as a white solid: ¹H NMR (360 MHz, CDCl₃) indicated an approximately 8:1 mixture of amide rotamers; for the major rotamer. δ 8.79 (s, 1H), 8.59 (d, J=3.9 Hz, 1H), 7.84 (d, J 7.6 Hz, 1H), 7.76 (d, J=15.5 Hz, 1H), 7.59 (d, J=7.8 Hz, 1H), 7.38-7.48 (m, 2H), 7.19-7.27 (m, 1H), 7.08-7.17 (m, 1H), 6.98 (d, J=15.5 Hz, 1H), 6.51 (s, 1H), 4.94 (s, 2H), 3.73 (s, 3H), 3.09 (s, 3H); MS (ES) m/e 306 $(M+H)^+$. Anal. Calcd for C₁₉H₁₉N₃O. 0.20 H₂O: C, 73.86; H, 6.33; N, 13.60. Found: C, 73.52; H, 6.32; N, 13.43.

Example 4

Preparation of (E)-3-(6-aminopyridin-3-yl)-N-methyl-N-(1-methyl-1H-indazol-3-ylmethyl)acrylamide a) (E)-3-(6-Aminopyridin-3-yl)-N-methyl-N-(1-methyl)-1H-indazol-3-ylmethyl)acrylamide EDC (230 mg, 1.2 mmole) was added to a solution (E)-3-(6-aminopyridin-3-yl)acrylic acid (164 mg, 1.0 mmole), 1-methyl-3-(methylaminomethyl)-1H-indazole (210 mg, 1.2 mmole), HOBt.H₂O (162 mg, 1.2 mmole), and Et₃N (0.28 mL, 2.0 mmole) in dry DMF (5 mL) at RT. After 18 hr the mixture was concentrated. Flash chromatography on silica gel (5% EtOH/EtOAc) gave the title compound (238 mg, 74%) as a white foam: $^1$H NMR (400 MHz, CDCl$_3$) δ 8.24 (m, 1H), 7.90 (m, 1H), 7.65 (m, 2H), 7.35 (m, 2H), 7.09 (m, 1H), 6.73 (m, 1H), 6.50 (m, 1H), 5.04 (s, 2H), 4.83 (bs, 2H), 4.04 (s, 3H), 3.10 (s, 3H); MS (ES) m/e 322 (M+H)$^+$.

Example 5

Preparation of (E)-3-(3,4-dihydro-2H-pyrido[3,2-b]-1,4-oxazin-7-yl)-N-methyl-N-(1-methyl-1H-indol-2-ylmethyl)acrylamide a) (E)-3-(3,4-Dihydro-2H-pyrido[3,2-b][1,4]oxazin-7-yl)-N-methyl-N-(1-methyl-1H-indol-2-ylmethyl)acrylamide EDC (230 mg, 1.2 mmole) was added to a solution (E)-3-(3,4-dihydro-2H-pyrido[3,2-b]-1,4-oxazin-7-yl)acrylic acid (206 mg, 1.0 mmole), 1-methyl-2-(methylaminomethyl)-1H-indole (209 mg, 1.2 mmole), HOBt.H$_2$O (162 mg, 1.2 mmole), and Et$_3$N (0.21 mL, 1.5 mmole) in dry DMF (5 mL) at RT. After 18 hr the mixture was concentrated. Flash chromatography on silica gel (5% EtOH/EtOAc) gave the title compound (238 mg, 66%) as a yellow solid: $^1$H NMR (400 MHz, d$^6$-DMSO) δ 7.99-6.95 (m, 8H), 6.40 (s, 1H), 4.82 (s, 2H), 4.11 (bs, 2H), 3.72 (bs, 3H), 3.67 (bs, 2H), 3.08 (s, 3H); for minor rotamer δ 6.15 (s, 1H), 5.02 (s, 2H), 2.96 (s, 3H); MS (ES) m/e 363 (M+H)$^+$.

Example 6

Preparation of (E)-N-methyl-N-[(1-methyl-1H-indol-2-ylmethyl)]-3-(5,6,7,8-tetrahydro-1,8-naphthyridin-3-yl)acrylamide a) (E)-N-Methyl-N-[(1-methyl-1-indol-2-ylmethyl)]-3-(5,6,7,8-tetrahydro-1,8-naphthyridin-3-yl)acrylamide EDC (203 mg, 1.06 mmole) was added to a solution (E)-3-(5,6,7,8-tetrahydro-1,8-naphthyridin-3-yl)acrylic acid (180 mg, 0.88 mmole), 1-methyl-2-(methylaminomethyl)-1H-indole (185 mg, 1.06 mmole), HOBt.H$_2$O (143 mg, 1.06 mmole), and Et$_3$N (0.31 mL, 2.2 mmole) in dry DMF (5 mL) at RT. After. 18 hr the mixture was concentrated. Flash chromatography on silica gel (10% EtOH/EtOAc) gave the title compound (222 mg, 70%) as a yellow solid: $^1$H NMR (400 MHz, DMSO-d$_6$) δ 7.99-6.82 (m, 8H), 6.40 (s, 1H), 4.82 (s, 2H), 3.67 (m, 2H), 3.29 (m, 3H), 3.07 (m, 3H), 2.73 (m, 2H), 1.77 (m, 2H); for minor rotamer δ 6.16 (s, 1H), 5.00 (s, 2H); MS (ES) m/e 361 (M+H)$^+$.

Example 7

Preparation of (E)-3-(6-aminopyridin-3-yl)-N-methyl-N-(thieno[2,3-b]thiophen-2-ylmethyl)acrylamide a) (E)-3-(6-Aminopyridin-3-yl)-N-m ylmethyl)acrylamide EDC (230 mg, 1.2 mmole) was added to a solution (E)-3-(6-aminopyridin-3-yl)acrylic acid (164 mg, 1.0 mmole), 2-(methylaminomethyl)thieno[2,3-b]thiophene (220 mg, 1.2 mmole). HOBt.H$_2$O (162 mg, 1.2 mmole), and Et$_3$N (0.35 mL, 2.5 mmole) in dry DMF (5 mL) at RT. After 18 hr the mixture was concentrated. Flash chromatography on silica gel (5% EtOH/EtOAc) gave the title compound (138 mg, 42%) as a tan solid: 1H NMR (400 MHz, d$^6$-DMSO) δ 8.15 (d, J=2.0 Hz, 1H), 7.84 (bs, 1H), 737 (d, J=5.2 Hz, 1H), 7.43 (d, J=15.2 Hz, 1H), 7.27 (m, 2H), 6.44 (m, 2H), 4.75 (s, 2H), 3.13 (s, 3H); for minor rotamer δ 5.00 (s, 2H), 2.95 (s, 3H); MS (ES) m/e 330 (M+H)$^+$.

Example 8

Preparation of (E)-3-(6-aminopyridin-3-yl)-N-methyl-N-(thieno[3,2-b]thiophen-2-ylmethyl)acrylamide a) (E)-3-(6-aminopyridin-3-yl)-N-methyl-N-(thieno[3,2-b]thiophen-2-ylmethyl)acrylamide EDC (230 mg, 1.2 mmole) was added to a solution (E)-3-(6-aminopyridin-3-yl)acrylic acid (164 mg, 1.0 mmole), 2-(methylaminomethyl)thieno[3,2-b]thiophene (220 mg, 1.2 mmole), HOBt.H$_2$O (162 mg, 1.2 mmole), and Et$_3$N (0.35 mL, 2.5 mmole) in dry DMF (5 mL) at RT. After 18 hr the mixture was diluted with H$_2$O and extracted with EtOAc (3×). The combined organic layers were dried (MgSO$_4$) and concentrated. The solid was taken up in 1:1 MeOH/H$_2$O and filtered. The filtrate was concentrated to approximately ⅓ volume. The precipitate was collected by filtration, washed with H$_2$O, and dried in vacuo to afford the title compound (139 mg, 42%) as a light tan solid: $^1$H NMR (400 MHz, d$^6$-DMSO) δ 8.15 (d, J=2.0 Hz, 1H), 7.83 (bd. 1H), 7.61 (d, J=5.2 Hz, 1H), 7.40 (m, 3H); 6.45 (m, 2H), 4.75 (s, 2H), 3.13 (s, 3H); for minor rotamer δ 5.00 (s, 2H), 2.95 (s, 3H); MS (ES) m/e 330 (M+H)$^+$.

Example 9

Preparation of (E)-3-(3H-imidazo[4,5-b]pyridin-6-yl)-methyl-N-(1-methyl-1H-indol-2-ylmethyl)acrylamide a) (E)-3-(3H-Imidazo[4,5-b]pyridin-6-yl)-N-methyl-N-(1-methyl-1H-indol-2-ylmethyl)acrylamide EDC (230 mg, 1.2 mmole) was added to a solution (E)-3-(3H-imidazo[4,5-b]pyridin-6-yl)acrylic acid (189 mg, 1.0 mmole), 1-methyl-2-(methylaminomethyl)-1H-indole (209 mg, 1.2 mmole), HOBt.H$_2$O (162 mg, 1.2 mmole), and Et$_3$N (0.28 mL, 2.0 mmole) in dry DMF (5 mL) at RT. After 18 hr the mixture was diluted with H$_2$O. The title compound (193 mg, 56%) was collected as a white solid by filtration, washed with H$_2$O, and dried in vacuo: $^1$H NMR (400 MHz, d$^6$-DMSO) δ 8.72 (s, 1H), 8.50 (s, 2H), 7.68 (d, J=15.4 Hz, 1H), 7.45 (m, 3H), 7.13 (m, 1H), 7.01 (m, 1H), 6.43 (s, 1H), 4.87 (s, 2H), 3.70 (s, 3H), 3.15 (s, 3H); for minor rotamer δ 8.68 (s, 1H), 8.47 (s, 2H), 6.19 (s, 1H), 5.10 (s, 2H), 3.74 (s, 3H), 3.01 (s, 3H); MS (ES) m/e 346 (M+H)$^+$.

Example 10

Preparation of (E)-3-(6-aminopyridin-3-yl)-N-methyl-N-(6-methyl-6H-thieno[2,3-b]pyrrol-5-ylmethyl)acrylamide a) (E)-3-(6-Aminopyridin-3-yl)-N-methyl-N-(6-methyl-6H-thieno[2,3-b]pyrrol-5-ylmethyl)acrylamide EDC (132 mg, 0.69 mmole) was added to a solution (E)-3-(6-aminopyridin-3-yl)acrylic acid (95 mg, 038 mmole), 6-methyl-5-(methylaminomethyl)-6H-thieno[2,3-b]pyrrole (142 mg, 0.69 mmole). HOBt.H$_2$O (93 mg, 0.69 mmole), and Et$_3$N (0.16 mL, 1.16 mmole) in dry DMF (3 mL) at RT. After 18 hr the mixture was diluted with H$_2$O and extracted with EtOAc (3×). The combined organic layers were dried (MgSO$_4$) and concentrated. The residue was taken up in MeOH and collected by filtration to give the title compound (65 mg, 34%) as a yellow solid: $^1$H NMR (400 MHz, d$^6$-DMSO) δ 8.15 (s, 1H), 7.81 (d, J=8.1 Hz, 1H), 7.43 (d, J=15.2 Hz, 1H), 6.96 (m, 2H), 6.43 (m, 3H), 4.70 (s, 2H), 3.61 (s, 3H), 3.00 (s, 3H); for minor rotamer δ 4.87 (s, 2H), 2.90 (s, 3H); MS (ES) m/e 327 (M+H)$^+$.

Example 11

Preparation of (E)-3-(2-aminopyrimidin-5-yl)-N-methyl-N-(1-methyl-1H-indol-2-ylmethyl)acrylamide According to the procedure of Example 1, except substituting (E)-3-(2-aminopyrimidin-5-yl)acrylic acid (0.50 g, 3.0 mmole) for (E)-3-(6-aminopyridin-3-yl)acrylic acid, the title compound (0.86 g, 89%) was prepared as an off-white solid: MS (ES) m/e 322 (M+H)$^+$.

Example 12

Preparation of (E)-3-(6-aminopyridin-3-yl)-N-(benzo[b]thiophen-2-ylmethyl)-N-methyl)acrylamide According to the procedure of Example 1, except substituting 2-(methylaminomethyl)benzo[b]thiophene (0.47 g, 2.68 mmole) for 1-methyl-2-(methylaminomethyl)indole, the title compound (0.71 g, 91%) was prepared as an off-white solid: MS (ES) m/e 324 (M+H)$^+$.

Example 13

Preparation of (E)-3-(6-aminopyridin-3-yl)-N-methyl-N-(1-methyl-1H-indol-2-ylmethyl)-2-butenamide According to the procedure of Example 1, except substituting (E)-3-(6-aminopyridin-3-yl)-2-methylacrylic acid (0.40 g, 2.24 mmole) for (E)-3-(6-aminopyridin-3-yl)acrylic acid, the title compound (0.65 g, 87%) was prepared as an off-white solid: MS (ES) m/e 335 (M+H)$^+$.

Example 14

Preparation of (E)-3-(6-amino-2-methylpyridin-3-yl)-N-methyl-N-(1-methyl-1H-indol-2-ylmethyl)acrylamide According to the procedure of Example 1, except substituting (E)-3-(6-amino-2-methylpyridin-3-yl)acrylic acid (0.40 g, 2.24 mmole) for (E)-3-(6-aminopyridin-3-yl)acrylic acid, the title compound (0.70 g, 94%) was prepared as an off-white solid: MS (ES) m/e 335 (M+H)$^+$.

Example 15

Preparation of (E)-3-(6-amino-5-methylpyridin-3-yl)-N-methyl-N-(1-methyl-1H-indol-2-ylmethyl)acrylamide According to the procedure of Example 1, except substituting (E)-3-(6-amino-5-methylpyridin-3-yl)acrylic acid (1.00 g, 5.62 mmole) for (E)-3-(6-aminopyridin-3-yl)acrylic acid, the title compound (1.78 g, 95%) was prepared as an off-white solid: MS (ES) m/e 335 (M+H)$^+$.

Example 16

Preparation of (E)-3-[6-acetylamino-pyridin-3-yl]-N-methyl-N-(1-methyl-1H-indol-2-ylmethyl)acrylamide To a stirred suspension of (E)-3-(6-aminopyridin-3-yl)-N-methyl-N-[(1-methyl-1H-indol-2-yl)methyl]acrylamide (0.50 g, 1.56 mmole) and NaHCO$_3$ (0.51 g, 6.09 mmole) in THF (75 mL) was added acetic anhydride (0.38 g, 3.74 mmole). The reaction was heated at reflux for 24 hrs and then concentrated. The remaining residue was extracted with EtOAc and purified on silica gel (95:5 CHCl$_3$/CH$_3$OH) to give the title compound (0.54 g, 96%) as an off-white solid: MS (ES) m/e 363 (M+H)$^+$.

Example 17

Preparation of (E)-3-(6-amino-5-methylpyridin-5-yl)-N-(benzo[b]thiophen-2-ylmethyl)-N-methyl)acrylamide According to the procedure of Example 1, except substituting (E)-3-(6-amino-5-methylpyridin-3-yl)acrylic acid (0.40 g, 2.24 mmole) for (E)-3-(6-aminopyridin-3-yl)acrylic acid, and substituting 2-(methylaminomethyl)benzo[b]thiophene (0.44 g, 2.47 mmole) for 1-methyl-2-(methylaminomethyl)indole, the title compound (0.69 g, 91%) was prepared as an off-white solid: MS (ES) m/e 338 (M+H)$^+$.

Example 18

Preparation of (E)-3-(6-amino-5-methylpyridin-3-yl)-N-methyl-N-(naphthalen-2-ylmethyl)acrylamide According to the procedure of Example 1, except substituting (E)-3-(6-amino-5-methylpyridin-3-yl)acrylic acid (0.40 g, 2.24 mmole) for (E)-3-(6-aminopyridin-3-yl)acrylic acid, and substituting 2-(methylaminomethyl)naphthalene (0.42 g, 2.47 mmole) for 1-methyl-2-(methylaminomethyl)indole, the title compound (0.65 g, 87%) was prepared as an off-white solid: MS (ES) m/e 332 (M+H)$^+$.

Example 19

Preparation of (E)-3-(6-acetylamino-5-methylpyridin-3-yl)-N-methyl-N-(1-methyl-1H-indol-2-ylmethyl)acrylamide According to the procedure of Example 16, except substituting (E)-3-(6-amino-5-methylpyridin-3-yl)-N-methyl-N-(1-methyl-1H-indol-2-ylmethyl)acrylamide (0.47 g, 1.4 mmole) for (E)-3-(6-aminopyridin-3-yl)-N-methyl-N-[(1-methyl-1H-indol-2-yl)methyl]acrylamide, the title compound (0.49 g, 93%) was prepared as an off-white solid: MS (ES) m/e 377 (M+H)$^+$.

Example 20

Preparation of (E)-3-[6-amino-5-(hydroxymethyl)pyridin-3-yl]-N-methyl-N-(1-methyl-1H-indol-2-ylmethyl)acrylamide According to the procedure of Example 1, except substituting (E)-3-[6-amino-5-(hydroxymethyl)pyridin-3-yl]

acrylic acid (0.40 g, 2.1 mmole) for (E)-3-(6-aminopyridin-3-yl)acrylic acid, the title compound (0.56 g, 77%) was prepared as an off-white solid: MS (ES) m/e 351 (M+H)$^+$.

Example 21

Preparation of (E)-N-methyl-N-(1-methyl-1H-indol-2-ylmethyl)-3-(7-oxo-5,6,7,8-tetrahydro-1,8-naphrayridin-3-yl)acrylamide a) N-Methyl-N-(1-methyl-1H-indol-2-ylmethyl) acrylamide To a solution of 1-methyl-2-(methylaminomethyl)indole (0.78 g, 4.5 mmole), from Preparation 1, and triethylamine (1.4 mL, 10.0 mmole) in $CH_2Cl_2$ (50 mL) at 5° C. was added acryloyl chloride (0.41 mL, 4.95 mmole). After 45 min, the reaction solution was poured onto $H_2O$ and the layers were separated. The organic phase was dried over $Na_2SO_4$ and concentrated to afford the title compound as a yellow oil. This was used directly without further purification.

b) (E)-N-Methyl-N-(1-methyl-1H-indol-2-ylmethyl)-3-(7-oxo-5,6,7,8-tetrahydro-1,8-naphthyridin-3-yl) acrylamide According to the procedure of Preparation 2 (a), except substituting N-methyl-N-(1-methyl-1H-indol-2-ylmethyl) acrylamide (0.90 g, 3.96 mmole) for benzyl acrylate, and substituting 6-bromo-3,4-dihydro-1H-1,8-naphthyridin-2-one (0.60 g, 2.64 mmole) for 2-amino-5-bromopyridine, the title compound (0.85 g, 86%) was prepared as an off-white solid: MS (ES) m/e 375 (M+H)$^+$.

Example 22

Preparation of (E)-3-[6-amino-5-[(2-hydroxyethylamino)carbonyl]pyridin-3-yl]-N-(1-methyl-1H-indol-2-ylmethyl)-N-methyl)acrylamide According to the procedure of Example 1, except substituting (E)-3-[6-amino-5-[(2-hydroxyethylamino)carbonyl]pyridin-3-yl]acrylic acid (1.35 g, 5.4 mmole) for (E)-3-(6-aminopyridin-3-yl)acrylic acid, the title compound (1.95 g, 89%) was prepared as an off-white solid: MS (ES) m/e 408 (M+H)$^+$.

Example 23

Preparation of (E)-N-methyl-N-(1-methyl-1H-indol-2-ylmethyl)-3-(3-methyl-2-oxo-1,2,3,4-tetrahydropyrido[2,3-d]pyrimidin-6-yl)acrylamide a) N-Methyl-N-(1-methyl-1H-indol-2-ylmethyl) acrylamide To a solution of 1-methyl-2-(methylaminomethyl)indole (0.96 g, 5.5 mmole), from Preparation 1, and triethylamine (1.54 mL, 11.0 mmole) in $CH_2Cl_2$ (50 mL) at 5° C. was added acryloyl chloride (0.48 mL, 6.0 mmole). After 45 min, the reaction solution was poured onto $H_2O$ and the layers were separated. The organic phase was dried over $Na_2SO_4$ and concentrated to afford the title compound as a yellow oil. This was used directly without further purification.

b) (E)-Methyl-N-(1-methyl-1H-indol-2-ylmethyl-3-(3-methyl-2-oxo-1,2,3,4-tetrahydropyrido[2,3-d]pyrimidin-6-yl)acrylamide According to the procedure of Preparation 2 (a), except substituting N-methyl-N-(1-methyl-1H-indol-2-ylmethyl) acrylamide (1.25 g, 5.5 mmole) for benzyl acrylate, and substituting 6-bromo-3-methyl-3,4-dihydro-1H-pyrido[2,3-d]pyrimidin-2-one (0.80 g, 33 mmole) for 2-amino-5-bromopyridine, the title compound (0.62 g, 49%) was prepared as an off-white solid: MS (ES) m/e 390 (M+H)$^+$.

Example 24

Preparation of (E)-3-(6-aminopyridin-3-yl)-N-methyl-N-(4-methyl-4H-theino[3,2-b]pyrrol-5-ylmethyl)acrylamide According to the procedure of Example of 1, except substituting 4-methyl-5-(methylaminomethyl)-4H-thieno[3,2-b]pyrrole (0.60 g, 3.3 mmole) for 1-methyl-2-(methylaminomethyl)indole, the title compound (0.90 g, 92%) was prepared as an off-white solid: MS (ES) m/e 327 (M+H)$^+$.

Example. 26

Preparation of (E)-3-[6-aminopyridin-3-yl]-N-methyl-N-(3-methyl-1H-inden-2-ylmethyl)acrylamide EDC (0.383 g, 2.0 mmole) was added to a solution of (E)-3-(o-aminopyridin-3-yl)acrylic acid (0.328 g, 2.0 mmole), 3-methyl-2-(methylaminomethyl)indene hydrochloride (0.420 g, 2.0 mmole), $HOBt.H_2O$ (0.306 g, 2.0 mmole), and triethylamine (0.57 mL, 4.0 mmole) in anhydrous DMF (18 mL) at RT. The reaction was stirred overnight and concentrated in vacuo. The residue was diluted with 5% $NaHCO_3$ and extracted with $CH_2Cl_2$. The combined organic extracts were washed with brine and dried over $MgSO_4$. Flash chromatography on silica gel (3% $MeOH/CH_2Cl_2$) gave the title compound (0.33 g, 52%) as a colorless solid: MS (ES) m/e 320.2 (M+H)$^+$. Anal. Calcd for $C_{20}H_{21}N_3O$. 0.4 $H_2O$; C, 73.57; H, 6.72; N, 12.86. Found: C, 73.94; H, 6.92; N, 12.50.

Example 27

Preparation of (E)-3-[6-aminopyridin-3-yl]-N-(1H-inden-2-ylmethyl)-N-methyl)acrylamide According to the procedure in Example 26, except substituting 2-(methylaminomethyl)indene hydrochloride for 3-methyl-2-(methylaminomethyl)indene hydrochloride, the title compound (0.23 g, 38%) was obtained as an off-white solid: MS (ES) m/e 306.2 (M+H)$^+$. Anal. Calcd for $C_{19}H_{19}N_3O$. 0.125 $H_2O$: C, 74.18; H, 6.30; N, 13.64. Found: C, 74.21; H, 6.25; N, 13.27.

Example 28

Preparation of (E)-3-[6-aminopyridin-3-yl]-N-(4-methoxy-1-methyl-1H-indol-2-ylmethyl-N-methyl) acrylamide According to the procedure in Example 26, except substituting 4-methoxy-1-methyl-1H-indol-2-ylmethyl)-methyl- 2-(methylaminomethyl)-1H-indole hydrochloride for 3-methyl-2-(methylaminomethyl)indene hydrochloride, the title compound (0.115 g, 68%) was obtained as an off white solid: MS (ES) m/e 351.2 (M+H)$^+$. Anal. Calcd for $C_{20}H_{22}N_4O_2$: C, 68.55; H, 632; N, 15.98. Found: C, 68.15; H, 633; N, 15.73.

Example 29

Preparation of (E)-3-[6-(acetylaminopyridin-3-yl]-N-methyl-N-(3-methyl-1H-inden-2-ylmethyl)acrylamide To a solution of (E)-3-[6-aminopyridin-3-yl]-N-methyl-N-(3-methyl-1H-inden-2-ylmethyl)acrylamide (0.159 g, 0.5 mmole), from Example 26, in anhydrous THF (20 mL) was added $NaHCO_3$ (0.126 g, 1.5 mmole) followed by acetic anhydride (0.153 g, 0.15 mmole). The mixture was heated at reflux for 40 hr, then was concentrated under vacuum. The residue was partitioned between $H_2O$ and EtOAc, and the organic layer was dried over $MgSO_4$, filtered and concentrated. The residue was triturated with diethyl ether to give the title compound (0.135 g, 74.8%) as an off-white solid: MS (ES) m/e 3623. (M+H)$^+$. Anal. Calcd for $C_{22}H_{23}N_3O_2.0.25$ $H_2O$: C, 72.20; H, 6.47; N, 11.47. Found: C, 72.42; H, 6.45; N, 11.07.

Example 30

Preparation of (E)-3-(6-aminopyridin-3-yl)-N-(1,4-dimethyl-1H-indol-2-ylmethyl)-N-methylacrylamide According to die procedure in Example 26, except substituting 1,4-dimethyl-2-(methylaminomethyl)-1H-indole hydrochloride for 3-methyl-2-(methylaminomethyl-indene hydrochloride, the title compound (0.088 g, 52.7%) was obtained as an off white solid: MS (ES) m/e 335.2 (M+H)$^+$. Anal. Calcd for $C_{20}H_{22}N_4O.0.125 H_2O$: C, 71.35; H, 6.66; N, 16.64. Found: C, 71.23; H, 6.65; N, 16.67.

Example 31

Preparation of (E)-N-methyl-N-(3-methyl-1H-inden-2-ylmethyl)-3-(7-oxo-5,6,7,8-tetrahydro-1,8-naphthyridin-3-yl)acrylamide a) N-Methyl-N-(3-methyl-1H-inden-2-ylmethyl)-acrylamide To a solution of 3-methyl-2-(methylaminomethyl)indene hydrochloride (0.132 g, 0.63 mmole), from Preparation 19, and triethylamine (0.19 g, 1.89 mmole) in $CH_2Cl_2$ (6 mL) at 0° C. was added a solution of acryloyl chloride (0.06 mL, 0.7 mmole) in $CH_2Cl_2$ (2 mL). The reaction was stirred at 0° C. for 1 hr, then was poured into water. The layers were separated, and the organic layer was washed with brine, dried over $MgSO_4$ and concentrated in vacuo to yield the title compound (0.145 g. quantitative) as an oily solid: MS (ES) m/e 228.2 (M+H)$^+$.

b) (E)-N-Methyl-N-(3-methyl-1H-inden-2-ylmethyl naphthyridin-3-yl)acrylamide

A mixture of 6-bromo-3,4-dihydro-1H-1,8-naphthyridin-2-one (0.096 g, 0.42 mmole), from Preparation 15, and N-methyl-N-(3-methyl-1H-inden-2-ylmethyl)acrylamide (0.141 g, 0.62 mmole) in propionitrile (10 mL) was treated with (i-Pr)$_2$NEt (0.15 mL, 0.08 mmole), palladium acetate (0.014 g, 0.062 mmole), and (o-tolyl)$_3$P (0.025 g, 0.08 mmole), and the resulting mixture was heated at gentle reflux. After 18 hr, die reaction was cooled, filtered through Celite®, and concentrated. Flash chromatography on silica gel (2% MeOH/ $CH_2Cl_2$) gave the title compound (0.06 g, 41%) as a glassy solid: MS (ES) m/e 374.2 (M+H)$^+$. Anal. Calcd for $C_{23}H_{23}N_3O_2.1.25 H_2O$: C, 69.76; H, 6.41; N, 10.61. Found: C, 69.86; H, 6.67; N, 10.51.

Example 32

Preparation of (E)-3-(6-aminopyridin-3-yl)-N-(1-methyl-1H-indol-2-ylmethyl)-N-propyl)acrylamide According to the procedure of Example 1, except substituting 1-methyl-2-(propylaminomethyl)-1H-indole (0.2 g, 1 mmole) for 1-methyl-2-(methylaminomethyl)-1H-indole, the title compound (0.14 g, 40%) was prepared as a white solid: MS (ES) m/e 349 (M+H)$^+$.

Example 33

Preparation of (E)-3-(6-aminopyridin-3-yl)-N-(5-fluoro-1-methyl-1H-indol-2-ylmethyl-N-methyl) acrylamide According to the procedure of Example 1, except substituting 5-fluoro-2-(methylaminomethyl)-1H-indole (0.192 g, 1 mmole) for 1-methyl-2-(methylaminomethyl 1H-indole, the title compound (0.1 g, 30%) was prepared as a white solid: MS (ES) m/e 339 (M+H)$^+$.

Example 34

Preparation of (E)-3-(6-aminopyridin-3-yl)-N-methyl-N-(naphthalen-1-ylmethyl)acrylamide According to the procedure of Example 1, except substituting N-methyl-1-(methylaminomethyl)naphthalene hydrochloride (0.2 g, 1 mmole) for 1-methyl-2-(methylaminomethyl)-1H-indole, the title compound (0.09 g, 28%) was prepared as a white solid: MS (ES) rate 318 (M+H)$^+$.

Example 35

Preparation of (E)-3-(6-aminopyridin-3-yl)-N-(benzofuran-2-ylmethyl-N-methyl)acrylamide According to the procedure of Example 1, except substituting 2-(methylamino methyl)benzofuran (0.17 g, 1.1 mmole) for 1-methyl-2-(methylaminomethyl)-1H-indole, the title compound (0.10 g, 30%) was prepared as a white solid: MS (ES) m/e 308 (M+H)$^+$.

Example 36

Preparation of (E)-N-methyl-3-[6-(methylamino) pyridin-3-yl]-N-(1-methyl-1H-indol-2-ylmethyl) acrylamide According to the procedure of Example 1, except substituting (E)-3-[6-(methylamino)pyridin-3-yl]acrylic acid (0.15 g, 0.84 mmole) for (E)-3-(6-aminopyridin-3-yl)acrylic acid, the title compound (0.1 g, 37%) was prepared as a white solid: MS (ES) m/e 335 (M+H)$^+$.

Example 37

Preparation of (E)-3-[6-(dimethylamino)pyridin-3-yl]-N-methyl-N-(1-methyl-1H-indol-2-ylmethyl) acrylamide According to the procedure of Example 1, except substituting (E)-3-[6-(dimethylamino)pyridin-3-yl]acrylic acid (0.20 g, 1.0 mmole) for (E)-3-(6-aminopyridin-3-yl)acrylic acid, the title compound (0.22 g, 63%) was prepared as a white solid: MS (ES) m/e 349 (M+H)+.

Example 38

Preparation of (E)-3-(6-aminopyridin-3-yl)-N-cyclopropyl-N-(1-methyl-1H-indol-2-ylmethyl)acrylamide According to the procedure of Example 1, except substituting 2-(cyclopropylamino)-1-methyl-1H-indole (0.22 g, 1.1 mmole) for 1-methyl-2-(methylaminomethyl-1H-indole the title compound (0.154 g, 53%) was prepared as a white solid: MS (ES) m/e 347 (M+H)+.

Example 39

Preparation of (E)-3-(6-aminopyridin-3-yl)-N-methyl-N-(quinolin-3-ylmethyl)acrylamide According to the procedure of Example 1, except substituting 3-(methylaminomethyl)quinoline (0.172 g, 1 mmole) for 1-methyl-2-(methylaminomethyl 1H-indole, the title compound (0.100 g, 31%) was prepared as a white solid: MS (ES) m/e 319 (M+H)+.

Example 40

Preparation of (E)-N-methyl-N-(1-methyl-1H-indol-2-ylmethyl)-3-(6-methylpyridine-3-yl)acrylamide According to the procedure of Example 1, except substituting (E)-3-(6-methylpyridin-3-yl)acrylic acid (0.18 g, 1.1 mmole) for (E)-3-(6-aminopyridin-3-yl)acrylic acid, the title compound (0.11 g, 31%) was prepared as a white solid: MS (ES) m/e 320 (M+H)+.

Example 41

Preparation of (E)-N-methyl-N-(1-methyl-1H-indol-2-ylmethyl)-3-[6-(2-oxopropylamino)pyridin-3-yl] acrylamide To a solution of (E)-3-(6-aminopyridin-3-yl)-N-methyl-N-(1-methyl-1H-indol-2-ylmethyl)acrylamide (0.12 g, 0.32 mmol), from Example 1, in DMF (1 mL) was added NaH (14 mg. 60% dispersion in oil, 0.35 mmol) and 1-bromo-2,2-dimethoxy-propane (0.05 mL 0.37 mmol). After 18 h at RT, the reaction was complete by TLC analysis. The solvent was removed under vacuum and the residue was purified by reverse phase preparative HPLC(YMC CombiPrep®ODS-A, 10% to 90% $CH_3CN/H_2O$+0.1% TFA) to give the title compound (11.6 mg) as a pale yellow oil: $^1$H NMR (400 MHz, MeOH-d4, 2:1 mixture of rotamers, minor rotamer in italics) δ 9.28 and *9.22* (s, 1H), 8.60 and *8.52* (s, 1H), 8.25 and *8.15* (d, 1H), 7.68 (d, J=16 Hz, 1H), 7.50 (m, 1H), 7.35 (m, 3H), 7.15 (m, 1H), 7.02 (m, 1H), 6.55 and *6.25* (s, 1H), 5.05 and *4.95* (s, 2H), 3.72 and *3.68* (s, 3H), 3.50 and *3.48* (s, 3H), 3.35 (s, 2H), 3.15 and *3.10* (s, 3H). MS (ES+) m/e 376.3 (M+H)+. Unreacted (E)-3-(6-aminopyridin-3-yl)-N-methyl-N-(1-methyl-1H-indol-2-ylmethyl)acrylamide (68 mg) was also recovered.

Example 42

Preparation of (E)-3-(6-aminopyridin-3-yl)-N-(1H-indol-2-ylmethyl)-N-methylacrylamide EDC (0.30 g, 138 mmole) was added to a solution of 3-(6-aminopyridin-3-yl)acrylic acid (0.26 g, 138 mmole). 2-(methylaminomethyl)-1H-indole (0.23 g, 1.43 mmole), $HOBt.H_2O$ (0.21 g, 1.58 mmole) and diisopropylethylamine (0.51 mL, 2.86 mmole) in DMF (20 mL) at RT. The reaction was stirred overnight, then was concentrated in vacuo. The residue was diluted with water and extracted with ethyl acetate. The combined organic extracts were washed with brine and dried over $Na_2SO_4$. Flash chromatography on silica gel (10% $MeOH/CHCl_3$) gave the title compound (0.30 g, 68%) as a light yellow solid: MS (ES) m/e 307 (M+H)+.

Example 43

Preparation of (E)-3-(6-aminopyridin-3-yl)-N-(1-ethyl-1H-indol-2-ylmethyl)-N-methyl)acrylamide EDC (0.84 g, 4.38 mmole) was added to a solution of 3-(6-aminopyridin-3-yl)acrylic acid (0.72 g, 4.38 mmole), 1-ethyl-2-(methylaminomethyl)-1H-indole (0.75 g, 3.98 mmole), $HOBt.H_2O$ (0.59 g, 4.38 mmole) and diisopropylethylamine (1.40 mL, 7.96 mmole) in DMF (30 mL) at RT. The reaction was stirred overnight, then was concentrated in vacuo. The residue was diluted with water and extracted with ethyl acetate. The combined organic extracts were washed with brine and dried over $Na_2SO_4$. Flash chromatography on silica gel (5% $MeOH/CHCl_3$) gave the title compound (0.40 g, 30%) as a light tan solid: MS (ES) m/e 335 (M+H)+.

Example 44

Preparation of (E)-3-(6-aminopyridin-3-yl)-N-methyl-N-(1-methyl-1H-indol-3-ylmethyl)acrylamide EDC (0.35 g, 1.89 mmole) was added to a solution of 3-(6-aminopyridin-3-yl)acrylic acid (0.31 g, 1.89 mmole). 1-methyl-3-(methylaminomethyl)-1H-indole (0.30 g, 1.72 mmole), $HOBt.H_2O$ (0.24 g, 1.89 mmole) and diisopropylethylamino (0.60 mL, 3.44 mmole) in DMF (20 mL) at RT. The reaction was stirred overnight, then was concentrated in vacuo. The residue was diluted with water and extracted with ethyl acetate. The combined organic extracts were washed with brine and dried over $Na_2SO_4$. Flash chromatography on silica gel (5% $MeOH/CHCl_3$) gave the title compound (0.30 g, 55%) as a light yellow solid: MS (ES) m/e 321 (M+H)+.

Example 45

Preparation of (E)-3-[6-((E)-but-2-enoylamino)pyridin-3-yl]-N-methyl-N-(1-methyl-1H-indol-2-ylmethyl)acrylamide Crotonic anhydride (0.29 mL, 1.96 mmole) was added to a solution of (E)-3-(6-aminopyridin-3-yl)-N-methyl-N-(1-methyl-1H-indol-2-ylmethyl)acrylamide (0.16 g, 0.49 mmole) and sodium bicarbonate (0.20 g, 2.45 mmole) in THF (30 mL) at RT, and the reaction was heated at reflux under nitrogen.

After 48 hr, the reaction was concentrated in vacuo and the residue was diluted with water and extracted with ethyl acetate. The combined extracts were dried over $Na_2SO_4$ and concentrated in vacuo to afford the title compound (0.10 g, 53%) as a tan solid: MS (ES) m/e 389 $(M+H)^+$.

Example 46

Preparation of (E)-3-[6-(1,3-dioxo-1,3-dihydroisoindol-2-yl]pyridin-3-yl]-N-methyl-N-(1-methyl-1H-indol-2-ylmethyl)acrylamide Phthalic anhydride (0.81 g, 5.48 mmole) was added to a solution of (E)-3-(6-aminopyridin-3-yl)-N-methyl-N-(1-(0.44 g, 1.37 mmole) and sodium bicarbonate (0.58 g, 6.85 mmole) in THF (70 mL) at RT, and the reaction was heated at reflux under nitrogen. After 48 hr, the reaction was concentrated in vacuo and the residue was purified by flash chromatography on silica gel (ethyl acetate). The title compound (0.21 g, 33%) was obtained as a white solid: MS (ES) m/e 451 $(M+H)^+$.

Example 47

Preparation of (E)-3-[6-[(2-carboxybenzoyl)amino] pyridin-3-yl]-N-methyl-N-(1-methyl-1H-indol-2-ylmethyl)acrylamide Phthalic anhydride (0.81 g, 5.48 mmole) was added to a solution of (E)-3-(6-aminopyridin-3-yl)-N-methyl-N-(1-methyl-1H-indol-2-ylmethyl)acrylamide (0.44 g, 1.37 mmole) and sodium bicarbonate (0.58 g, 6.85 mmole) in THF (70 mL) at RT, and the reaction was heated at reflux under nitrogen. After 48 hr, the reaction was concentrated in vacuo and the residue was diluted with water and extracted with ethyl acetate. The combined extracts were dried over $Na_2SO_4$ and concentrated. Flash chromatography on silica gel (10% $MeOH/CHCl_3$) gave the title compound (0.10 g, 16%) as a light yellow solid: MS (ES) m/e 469 $(M+H)^+$.

Example 48

Preparation of (E)-N-Methyl-N-(1-methyl-1H-indol-2-ylmethyl)-3-[6-(propionylamino)pyridin-3-yl]acrylamide Propionic anhydride (0.90 mL, 7.04 mmole) was added to a solution of (E)-3-(6-aminopyridin-3-yl)-N-methyl-N-(1-methyl-1H-indol-2-ylmethyl)acrylamide (0.56 g, 1.76 mmole) and sodium bicarbonate (0.74 g, 8.8 mmole) in THF (40 mL) at RT, and the reaction was heated at reflux under nitrogen. After 48 hr, the reaction was concentrated in vacuo and the residue was diluted with water and extracted with ethyl acetate. The combined extracts were dried over $Na_2SO_4$ and concentrated. Flash chromatography on silica gel (ethyl acetate) gave the title compound (0.35 g, 53%) as a white solid: MS (ES) m/e 377 $(M+H)^+$.

Example 49

Preparation of (E)-3-[6-(3-Ethylureido)pyridin-3-yl]-N-methyl-N-(1-methyl-1H-indol-2-ylmethyl)acrylamide Ethyl isocyanate (0.13 mL, 1.68 mmole) was added to a solution of (E)-3-(6-aminopyridin-3-yl)-N-methyl-N-(1-methyl-1H-indol-2-ylmethyl)acrylamide (0.27 g, 0.84 mmole) and triethylamine (0.29 mL, 2.1 mmole) in DMF (30 mL) at RT. The reaction was stirred for 6 days, then was concentrated in vacuo, and the residue was diluted with water and extracted with ethyl acetate. The combined organic extracts were washed with brine, dried over $Na_2SO_4$, and concentrated. Flash chromatography on silica gel (ethyl acetate) gave the title compound (80 mg, 24%) as a light yellow solid: MS (ES) m/e 392 $(M+H)^+$.

Example 50

Preparation of (E)-N-methyl-N-(1-methyl-1H-indol-2-ylmethyl)-3-[6-(3-methyl-ureido)pyridin-3-yl] acrylamide Methyl isocyanate (0.18 mL, 3.05 mmole) was added to a solution of (E)-3-(6-aminopyridin-3-yl)-N-methyl-N-(1-methyl-1H-indol-2-ylmethyl)acrylamide (0.20 g, 0.61 mmole) and triethylamine (0.17 mL, 1.22 mmole) in DMF (20 mL) at RT. The reaction was stirred for 5 days, then was concentrated in vacuo, and the residue was diluted with water and extracted with ethyl acetate. The combined organic extracts were washed with brine, dried over $Na_2SO_4$, and concentrated. Flash chromatography on silica gel (ethyl acetate) gave the title compound (0.10 g, 43%) as an off white solid: MS (ES) m/e 378 $(M+H)^+$.

Example 51

Preparation of (E)-3-[6-(acetylamino)pyridin-3-yl]-N-methyl-N-(1-methyl-1H-indol-3-ylmethyl)acrylamide Acetic anhydride (0.12 mL, 1.24 mmole) was added to a solution of (E)-3-(6-aminopyridin-3-yl)-N-(1-methyl-1H-indol-3-ylmethyl)-N-methylacrylamide (0.10 g, 0.31 mmole) and sodium bicarbonate (0.13 g, 1.55 mmole) in THF (20 mL) at RT, and the reaction was heated at reflux under nitrogen. After 48 hr, the reaction was concentrated in vacuo and the residue was diluted with water and extracted with ethyl acetate. The combined extracts were dried over $Na_2SO_4$ and concentrated. Flash chromatography on silica gel (ethyl acetate) gave the title compound (50 mg. 45%) as a white solid: MS (ES) m/e 363 $(M+H)^+$.

Example 52

Preparation of (E)-3-(6-aminopyridin-3-yl)-2-methyl-N-methyl-N-(1-methyl-1H-indol-2-ylmethyl) acrylamide To a stirred solution of (E)-3-(6-aminopyridin-3-yl)-2-methylacrylic acid HCl salt (0.5 g, 2.3 mmole) in dry 1:1 DMF/$CH_2Cl_2$ (30 mL) at RT was added 1-methyl-2-(methylaminomethyl)indole (0.42 g, 2.4 mmole), $HOBt.H_2O$ (0.32 g, 2.4 mmole), $Et_3N$ (0.66 mL, 4.7 mmole), and EDC (0.46 g, 2.4 mmole). After stirring for 24 hr the reaction was concentrated to dryness. The residue was taken up in ethyl acetate and the solution was washed with $H_2O$, dried ($Na_2SO_4$), and concentrated under vacuum. Flash chromatography on silica gel (4% methanol/$CHCl_3$) followed by trituration with ethyl acetate/hexane gave the title compound (035 g, 75%) as an off-white solid: LCMS (ES) m/e 335.2 $(M+H)^+$; $^1H$ NMR (300 MHz, DMSO-$d_6$) δ 7.96 (s, 1H), 732 (d, J=7.8 Hz, 1H), 7.48 (dd, 1H), 7.43 (d, J=7.8 Hz, 1H), 7.14 (t, 1H), 7.03 (t, 1H), 6.46 (d, J=8.7 Hz, 1H), 6.43 (s, 1H), 6.40 (s, 1H), 6.17 (br s, 2H).

Example 53

Preparation of 2-(6-aminopyridin-3-ylmethyl)-N-methyl-N-(1-methyl-1H-indol-2-ylmethyl)acrylamide According to the procedure of Example 52, except substituting 2-(6-aminopyridin-3-ylmethyl)acrylic acid HCl salt (0.50 g, 2.3 mmole) for (E)-3-(6-aminopyridin-3-yl)-2-methylacrylic acid HQ salt, the title compound (0.55 g, 75%) was prepared as an off-white solid following purification by flash chromatography on silica gel (4% methanol/CHCl$_3$): LCMS (ES) m/e 335.2 (M+H)$^+$; $^1$H NMR (300 MHz, DMSO-d$_6$) δ 7.75 (d, J=2.0 Hz, 1H), 7.50 (d, J=7.6 Hz, 1H), 738 (d, J=8.1 Hz, 1H), 7.22 (dd, 1H), 7.12 (t, 1H), 7.01 (t, 1H), 6.40 (d, J=8.4 Hz, 1H), 6.17 (s, 1H), 5.83 (br s, 2H), 5.23 (s, 1H), 5.14 (s, 1H), 4.73 (s, 2H), 3.57 (s, 3H), 336 (s, 2H), 2.82 (s, 3H).

Example 54

Preparation of (E)-3-(6-aminopyridin-3-yl)-N-methyl-N-(naphthalen-2-ylmethyl)acrylamide To a stirred solution of (E)-3-(6-aminopyridin-3-yl)acrylic acid (0.30 g, 1.8 mmole) in 1:1 DMF/CH$_2$Cl$_2$ (23 mL) was added 2-(methylaminomethyl)naphthalene (0.34 g, 2 mmole), HOBt.H$_2$O (0.27 g, 2 mmole), Et$_3$N (0.28 mL, 2 mmole), and EDC (038 g, 2 mmole). After stirring at RT for 16 hr the reaction was concentrated under vacuum. The residue was taken up in ethyl acetate and the solution was washed with H$_2$O, dried (Na$_2$SO$_4$) and concentrated to dryness. Purification by flash chromatography on silica gel (4% methanol/CHCl$_3$), trituration with 1:1 ethyl acetate/hexane, filtration, and drying under vacuum gave the title compound (0.49 g, 81%) as an off-white solid: LCMS (ES) m/e 318.0 (M+H)$^+$.

Example 55

Preparation of (E)-3-(6-amino-4-methylpyridin-3-yl)-N-methyl-N-(1-methyl-1H-indol-2-ylmethyl)acrylamide To a stirred solution of (E)-3-(6-amino-4-methylpyridin-3-yl)acrylic acid HCl salt (0.70 g, 33 mmole) in 1:1 DMF/CH$_2$Cl$_2$ (30 mL) was added Et$_3$N (0.42 mL, 3 mmole). 1-methyl-2-(methylaminomethyl)indole (0.50 g, 2.9 mmole), HOBt.H$_2$O (0.41 g, 3 mmole), and DCC (0.70 g, 3 mmole). After stirring at RT for 16 hr the reaction was concentrated under vacuum. The residue was taken up in ethyl acetate and filtered. The filtrate was washed with 1.0 N Na$_2$CO$_3$ then with brine, dried (Na$_2$SO$_4$), and concentrated under vacuum. Purification by flash chromatography on silica gel (4% methanol/CHCl$_3$) gave the title compound (0.74 g, 74%) as a pale yellow solid: LCMS (ES) m/e 335.2 (M+H)$^+$.

Example 56

Preparation of (E)-3-(6-aminopyridin-3-yl)-N-(1,3-dimethyl-1H-indol-2-ylmethyl)-N-methyl)acrylamide To a stirred solution of 1,3-dimethyl-2-(methylaminomethyl)-1H-indole (0.6 g, 3.2 mmole) in 1:1 DMF/CH$_2$Cl$_2$ (25 mL) was added (E)-3-(6-aminopyridin-3-yl)acrylic acid (0.50 g, 3 mmole), HOBt.H$_2$O (0.43 g, 3.2 mmole), and DCC (0.66 g, 32 mmole). After stirring at RT for 16 hr the reaction was concentrated under vacuum. Purification by flash chromatography on silica gel (3% methanol/CHCl$_3$) gave the title compound (0.83 g, 83%) as an off-white solid: LCMS (ES) m/e 335.4 (M+H)$^+$.

Example 57

Preparation of (E)-N-methyl-N-(1-methyl-1H-indol-2-ylmethyl)-3-(2-oxo-1,4-dihydro-2H-pyrido[2,3-d]-1,3-oxazin-6-yl)acrylamide a) N-Methyl-N-(1-methyl-1H-indol-2-ylmethyl)acrylamide To a stirred solution of 1-methyl-2-(methylaminomethyl)-1H-indole (1.0 g, 5.7 mmole), from Preparation 1, and Et$_3$N (0.9 mL, 6.4 mmole) in CH$_2$Cl$_2$ (50 mL) at 0° C. was added dropwise acryloyl chloride (0.51 mL, 6 mmole) over 5 minutes. The reaction was stirred at 0° C. for 1 hr, then was poured into ice water. The organic phase was separated, washed with brine, dried (MgSO$_4$), and concentrated to dryness to give the title compound (1.19 g, 91%) as a yellow oil. This was used without further purification: TLC (silica gel, 50% EtOAc/hexanes) R$_f$=0.31.

b) (E)-N-methyl-N-(1-methyl-1H-indol-2-ylmethyl)-3-(2-oxo-1,4-dihydro-2H-pyrido[2,3-d]-1,3-oxazin-6-yl)acrylamide To a stirred solution of N-methyl-N-(1-methyl-1H-indol-2-ylmethyl)acrylamide (1.19 g, 5.2 mmole) in propionitrile (50 mL) was added 6-bromo-2-oxo-1,4-dihydro-2H-pyrido[2,3-d]-1,3-oxazine (1.1 g, 4.9 mmole), DIEA (1.75 mL, 10 mmole), palladium(II) acetate (112 mg, 0.5 mmole), and tri-o-tolylphosphine (304 mg, 1.0 mmole). The reaction was purged with argon and heated at reflux for 16 hr, then was cooled to RT and concentrated under vacuum. The residue was taken up in CHCl$_3$ and the solution was filtered through a pad of silica gel (3% methanol/CHCl$_3$). The filtrate was concentrated and the residue was triturated with ethyl acetate, collected by suction filtration, and dried under vacuum gave the title compound (1.02 g, 55%) as an off-white solid: LCMS (ES) m/e 377 4 (M+H)$^+$.

Example 58

Preparation of (E)-N-(1,3-dimethyl-1H-indol-2-ylmethyl)-N-methyl-3-(7-oxo-5,6,7,8-tetrahydro-1,8-naphthyridin-3-yl)acrylamide a) N-(1,3-Dimethyl-1H-indol-2-ylmethyl)-N-methyl)acrylamide To a stirred solution of 1,3-dimethyl-2-(methylaminomethyl)indole (1.5 g, 8 mmole), from Preparation 40, and Et$_3$N (1.12 mL, 8 mmole) in CH$_2$Cl$_2$ (75 mL) at 0° C. was added acryloyl chloride (0.65 mL, 8 mmole) dropwise over 5 minutes. The reaction was stirred at 0° C. for 1 hr then was poured into ice water. The organic phase was separated, washed with brine, dried (MgSO$_4$), and concentrated to dryness to give the title compound (1.7 g, 90%) as a yellow oil. This was used without further purification: TLC silica gel (50% EtOAc/hexanes) R$_f$=0.41.

b) (E)-N-(1,3-Dimethyl-1H-indol-2-ylmethyl)-N-methyl-3-(7-oxo-5,6,7,8-tetrahydro[1,8]naphthyridin-3-yl)acrylamide To a stirred solution of N-(1,3-dimethyl-1H-indol-2-ylmethyl)-N-methyl)acrylamide (1.7 g, 7 mmole) in propionitrile (50 mL) was added 6-bromo-3,4-dihydro-1H-1,8-naphthyridin-2-one (1.16 g, 5.1 mmole), DIEA (1.8 mL, 10.3 mmole), palladium(II) acetate (112 mg. 0.5 mmole), and tri-o-tolylphosphine (304 mg, 1.0 mmole). The reaction was purged with argon and heated at reflux for 16 hr, then was cooled to RT and concentrated under vacuum. Purification by flash chromatography on silica gel (5% methanol/CHCl$_3$), trituration with ethyl acetate, filtration, and drying under vacuum gave the title compound (1.17 g, 59%) as an off-white solid: LCMS (ES) m/e 389.2 (M+H)$^+$.

Example 59

Preparation of (E)-3-(6-aminopyridin-3-yl)-N-methyl-N-(3-methylbenzo[b]thiophen-2-ylmethyl)acrylamide To a stirred solution of 3-methyl-2-(methylaminomethyl)benzo[b]thiophene (0.30 g, 1.6 mmole) in 1:1 DMF/CH$_2$Cl$_2$ was added (E)-3-(6-aminopyridin-3-yl)acrylic acid (0.33 g, 2 mmole), HOBt.H$_2$O (0.27 g, 2 mmole), and DCC (0.41 g, 2 mmole). The reaction was stirred for 16 hr, then was concentrated under vacuum. The residue was taken up in CHCl$_3$, washed with H$_2$O, dried (Na$_2$SO$_4$) and concentrated. Purification by flash chromatography on silica gel (4% methanol/CHCl$_3$) gave the title compound (0.39 g, 72%) as a pale yellow solid: LCMS (ES) m/e 338.2 (M+H)$^+$.

Example 60

Preparation of (E)-3-(2-aminopyrimidin-5-yl)-N-(benzo[b]thiophen-2-ylmethyl)-N-methylacrylamide According to the procedure of Example 1, except substituting (E)-3-(2-aminopyrimidin-5-yl)acrylic acid (1.49 g, 7.1 mmole) for (E)-3-(6-aminopyridin-3-yl)acrylic acid, and substituting 2-(methylaminomethyl)theino[2,3-b]thiophene (1.38 g, 7.8 mmole) for 1-methyl-2-(methylaminomethyl)indole, the title compound (2.04 g, 89%) was prepared as a yellow solid: MS (ES) m/e 325 (M+H)$^+$.

Example 61

Preparation of (E)-3-(2-aminopyrimidin-5-yl)-N-methyl-N-(1-methyl-1H-indol-3-ylmethyl)acrylamide According to the procedure of Example 31, except substituting 1-methyl-3-(methylaminomethyl)indole (1.96 g, 8.6 mmole) for 3-methyl-2-(methylaminomethyl)indene hydrochloride, and substituting 2-amino-5-bromopyrimidine (1.0 g, 5.75 mmole) for 6-bromo-3,4-dihydro-1H-1,8-naphthyridin-2-one, the title compound (1.44 g, 78%) was prepared as a yellow solid: MS (ES) m/e 322 (M+H)$^+$.

Example 62

Preparation of (E)-N-methyl-N-(1-methyl-1H-indol-3-ylmethyl)-3-(7-oxo-5,6,7,8-tetrahydro-1,8-naphthyridin-3-yl)acrylamide According to the procedure of Example 31, except substituting 1-methyl-3-(methylaminomethyl)indole (0.75 g, 3.3 mmole) for 3-methyl-2-(methylaminomethyl)indene hydrochloride, the title compound (0.59 g, 72%) was prepared as a light yellow solid: MS (ES) m/e 375 (M+H)$^+$.

Example 63

Preparation of (E)-3-[2-aminopyrimidin-5-yl]-N-methyl-N-(3-methyl-1H-inden-2-ylmethyl)acrylamide According to the procedure of Example 31, except substituting 2-amino-5-bromopyrimidine (0.32 g, 1.84 mmole) for 6-bromo-3,4-dihydro-1H-1,8-naphthyridin-2-one, the title compound (0.47 g, 80%) was prepared as a light yellow solid: MS (ES) m/e 321 (M+H)$^+$.

Example 64

Preparation of (E)-3-[2-(acetylamino)pyrimidin-5-yl]-N-methyl-N-(1-methyl-1H-indol-2-ylmethyl)acrylamide According to the procedure of Example 31, except substituting 1-methyl-2-(methylaminomethyl)indole (1.45 g, 8.33 mmole) for 3-methyl-2-(methylaminomethyl)indene hydrochloride, and substituting 2-acetylamino-5-bromopyrimidine (1.20 g, 5.55 mmole) for 6-bromo-3,4-dihydro-1H-1,8-naphthyridin-2-one, the title compound (2.38 g, 43%) was prepared as a yellow solid: MS (ES) m/e 364 (M+H)$^+$.

Example 65

Preparation of (E)-3-(6-aminopyridin-3-yl)-N-methyl-N-(2-methyl-1H-indol-3-ylmethyl)acrylamide According to the procedure of Example 1, except substituting 2-methyl-3-(methylaminomethyl)indole (0.45 g, 2.58 mmole) for 1-methyl-2-(methylaminomethyl)indole, the title compound (0.68 g, 90%) was prepared as a yellow solid: MS (ES) m/e 321 (M+H)$^+$.

Example 66

Preparation of (E)-3-(2-aminopyrimidin-5-yl)-N-(1,2-dimethyl-1H-indol-3-ylmethyl)-N-methylacrylamide According to the procedure of Example 31, except substituting 1,2-dimethyl-3-(methylaminomethyl)indole (1.62 g, 8.62 mmole) for 3-methyl-2-(methylaminomethyl)indene hydrochloride, and substituting 2-amino-5-bromopyrimidine (1.00 g, 5.75 mmole) for 6-bromo-3,4-dihydro-1H-1,8-naphthyridin-2-one, the title compound (1.33 g, 69%) was prepared as a yellow solid: MS (ES) m/e 336 (M+H)$^+$.

Example 67

Preparation of (E)-N-methyl-N-(1-methyl-1H-indol-2-ylmethyl)-3-(3-oxo-3,4-dihydro-2H-pyrido[3,2-b]-1,4-oxazin-7-yl)acrylamide According to the procedure of Example 31, except substituting 1-methyl-2-(methylaminomethyl)indole (1.17 g, 6.75 mmole) for 3-methyl-2-(methylaminomethyl)indene hydrochloride, and substituting 5-bromo-2H-pyrido[3,2-b]-1,4-oxazin-3(4H)-one (1.03 g, 4.50 mmole) for 6-bromo-3,4-dihydro-1H-1,8-naphthyridin-2-one, the title compound (0.90 g, 53%) was prepared as a light yellow solid: MS (ES) m/e 377 (M+H)$^+$.

Example 68

Preparation of (E)-N-methyl-N-(2-methyl-1H-indol-3-ylmethyl)-3-(7-oxo-5,6,7,8-tetrahydro-1,8-naphthyridin-3-yl)acrylamide According to the procedure of Example 31, except substituting 2-methyl-3-(methylaminomethyl)indole (1.40 g, 8.00 mmole) for 3-methyl-2-(methylaminomethyl)indene hydrochloride, the title compound (1.30 g, 65%) was prepared as a light yellow solid: MS (ES) m/e 376 (M+H)$^+$.

Example 69

Preparation of (E)-N-methyl-N-(1-methyl-1H-indol-3-ylmethyl)-3-(3-oxo-3,4-dihydro-2H-pyrido[3,2-b]-1,4-oxazin-7-yl)acrylamide According to the procedure of Example 31, except substituting 1-methyl-3-(methylaminomethyl)indole (0.38 g, 2.20 mmole) for 3-methyl-2-(methylaminomethyl)indene hydrochloride, and substituting 5-bromo-2H-pyrido[3,2-b]-1,4-oxazin-3(4H)-one (0.32 g, 1.40 mmole) for 6-bromo-3,4-dihydro-1H-1,8-naphthyridin-2-one, the title compound (0.26 g, 50%) was prepared as a light yellow solid: MS (ES) m/e 377 (M+H)$^+$.

Example 70

Preparation of (E)-N-methyl-N-(1-methyl-1H-indol-2-ylmethyl)-3-(7-oxo-5,6,7,8-tetrahydro-1,8-naphthyridin-3-yl)propionamide To a solution of (E)-N-methyl-N-(1-methyl-1H-indol-2-ylmethyl)-3-(7-oxo-5,6,7,8-tetrahydro-1,8-naphthyridin-3-yl)acrylamide (0.15 g, 0.40 mmole) in dioxane at RT was added Pd(OH)$_2$. The flask was sealed with a septum through which a balloon containing hydrogen (1 atm) was inserted. The reaction was stirred at RT overnight and then filtered through a pad of Celite®, washing with methanol. The filtrate was concentrated to give the title compound (0.14 g, 94%) as a light yellow solid: MS (ES) m/e 378 (M+H)$^+$.

Example 71

Preparation of (E)-3-(6-aminopyridin-3-yl)-N-(6-methoxy-1-methyl-1H-indol-2-ylmethyl)-N-methylacrylamide According to the procedure of Example 1, except substituting 1-methyl-2-(methylaminomethyl)-6-methoxy-1H-indole for 1-methyl-2-(methylaminomethyl)-1H-indole, the title compound (50%) was prepared as a light yellow solid: MS (ES) m/e 351.4 (M+H)$^+$. Anal. Calcd for C$_{20}$H$_{22}$N$_4$O$_2$.1.5 H$_2$O: C, 63.64; H, 6.66; N, 14.84. Found: C, 63.51; H, 6.21; N, 14.71.

Example 72

Preparation of (E)-3-(7-aminopyridin-3-yl)-N-(1,7-dimethyl-1H-indol-3-ylmethyl)-N-methyl)acrylamide According to the procedure of Example 1, except substituting 1,7-dimethyl-3-(methylaminomethyl)-1H-indole for 1-methyl-2-(methylaminomethyl)-1H-indole, the title compound (50%) was prepared as a light yellow solid: MS (ES) m/e 335.2 (M+H)$^+$. Anal. Calcd for C$_{20}$H$_{22}$N$_4$O$_2$.0.5 H$_2$O: C, 69.99; H, 6.76; N, 16.31. Found: C, 70.02; H, 659; N, 16.43.

Example 73

Preparation of (E)-3-(6-aminopyridin-3-yl)-N-(1,5-dimethyl-1H-indol-3-ylmethyl-N-methylacrylamide According to the procedure of Example 1, except substituting 1,5-dimethyl-3-(methylaminomethyl)-1H-indole for 1-methyl-2-(methylaminomethyl)-1H-indole, the title compound (33%) was prepared as a light yellow solid: MS (ES) m/e 3352. (M+H)$^+$. Anal. Calcd for C$_{20}$H$_{22}$N$_4$O$_2$·0.5 H$_2$O: C, 68.16; H, 6.86; N, 15.89. Found: C, 68.37; H. 6.70; N, 15.62.

Example 74

Preparation of (E)-3-(6-aminopyridin-3-yl)-N-(1,6-dimethyl-1H-indol-3-ylmethyl)-N-methylacrylamide According to the procedure of Example 1, except substituting 1,6-dimethyl-3-(methylaminomethyl)-1H-indole for 1-methyl-2-(methylaminomethyl)-1H-indole, the title compound (33%) was prepared as a light tan solid: MS (ES) m/e 335.2 (M+H)$^+$. Anal. Calcd for C$_{20}$H$_{22}$N$_4$O$_2$.0.375 H$_2$O: C, 70.41; H, 6.64; N, 16.42. Found: C, 70.40; H, 6.61; N, 16.19.

Example 75

Preparation of (E)-3-(6-aminopyridin-3-yl)-N-(1-benzyl-1H-indol-3-ylmethyl)-N-methylacrylamide EDC (0.42 g, 2.20 mmole) was added to a solution of 3-(6-aminopyridin-3-yl)acrylic acid (0.36 g, 2.20 mmole), 1-benzyl-3-(methylaminomethyl)-1H-indole (0.50 g, 2.00 mmole), HOBt.H$_2$O (0.30 g, 22.0 mmole) and diisopropylethylamine (0.70 mL, 4.00 mmole) in DMF (30 mL) at RT. The reaction was stirred overnight, then was concentrated in vacuo. The residue was diluted with water and extracted with ethyl acetate. The combined organic extracts were washed with brine and dried over Na$_2$SO$_4$. Flash chromatography on silica gel (10% MeOH/CHCl$_3$) gave the title compound (0.48 g, 60%) as a light yellow solid: MS (ES) m/e 397 (M+H)$^+$.

Example 76

Preparation of (E)-N-methyl-N-(1-methyl-1H-indol-2-ylmethyl)-3-[6-(phenylamino)pyridin-3-yl]acrylamide a) N-Methyl-N-(1-methyl-1H-indol-2-ylmethyl) acrylamide To a stirred solution of 1-methyl-2-(methylaminomethyl)-1H-indole (13 g, 8.6 mmole) and Et$_3$N (1.35 mL, 9.6 mmole) in CH$_2$Cl$_2$ (75 mL) at 0° C. was added dropwise acryloyl chloride (0.77 mL, 93 mmole) over 5 minutes. After 2 h the reaction was washed with cold H$_2$O, brine, dried (MgSO$_4$) and concentrated under vacuum. The residue was used without further purification.

b) (E)-N-Methyl-N-(1-methyl-1H-indol-2-ylmethyl)-3-[6-(phenylamino)pyridin-3-yl]acrylamide N-Methyl-N-(1-methyl-1H-indol-2-ylmethyl)acrylamide (from Example 76 (a)) was taken up in propionitrile (50 mL). To this solution was added with stirring 2-phenylamino-5- bromopyridine (1.3 g, 5.2 mmole), DIEA (1.8 mL, 10 mmole), Pd(OAc)$_2$ (112 mg, 05 mmole) and P(o-tol)$_3$ (304 mg, 1.0 mmole). The reaction was purged with argon then stirred at reflux for 16 h. After cooling to room temperature the reaction was concentrated to dryness under vacuum. Flash chromatography on silica gel (5% methanol/CHCl$_3$) followed by a second flash column on silica gel (50-70% EtOAc/CHCl$_3$) left a residue that was triturated with EtOAc/petroleum ether. Filtration and drying under vacuum gave the title compound (1.42 g, 69%) as an off-white powder: MS (ES) m/e 396.20 (M+H)$^+$.

Example 77

Preparation of (E)-3-(6-aminopyridin-3-yl)-N-(1,2-dimethyl-1H-indol-3-ylmethyl)-N-methylacrylamide To a stirred solution of 1,2-dimethyl-3-(methylaminomethyl)-1H-indole(0.8 g, 4.2 mmole) in 1:1 DMF/CH$_2$Cl$_2$ (30 mL) at RT was added (E)-3-(6-aminopyridin-3-yl)acrylic acid (0.7 g, 4.3 mmole), Et$_3$N (0.61 mL, 4.3 mmole), HOBt.H$_2$O (0.58 g, 4.3 mmole) and EDC (0.83 g, 4.3 mmole). After 16 h the reaction was concentrated under vacuum and the residue was taken up in EtOAc (100 mL). The solution was washed with 1.0 N Na$_2$CO$_3$ (100 mL) then with brine, dried (Na$_2$SO$_4$), and concentrated. Purification by flash chromatography on silica gel (4% MeOH/CHCl$_3$) followed by trituration with 1:1 Et$_2$O/petroleum ether and drying under vacuum gave the title compound (1.36 g, 97%) as an off-white solid: MS (ES) m/e 335.2 (M+H)$^+$.

Example 78

Preparation of (E)-3-(6-aminopyridin-3-yl)-N-(benzo[b]thiophen-3-ylmethyl)-N-methylacrylamide According to the procedure of Example 77, except substituting 3-(methylaminomethyl)benzo[b]thiophene (0.75 g, 4.2 mmole) for the 1,2-dimethyl-3-(methylaminomethyl)-1H-indole, the title compound (1.05 g, 83%) was prepared as an off-white solid: MS (ES) m/e 324.2 (M+H)$^+$.

Example 79

Preparation of (E)-N-methyl-N-(1-methyl-1H-indol-2-ylmethyl)-3-[6-(pyridin-2-ylamino)pyridin-3-yl]acrylamide According to the procedure of Example 76 (a) and (b), except substituting 5-bromo-2,2'-dipyridylamine (1.3 g, 5.2 mmole) for the 2-phenylamino-5-bromopyridine, the title compound (1.54 g, 75%) was prepared as an off-white solid: MS (ES) m/e 398.2 (M+H)$^+$.

Example 80

Preparation of (E)-N-(1,2-dimethyl-1H-indol-3-ylmethyl)-N-methyl-3-(7-oxo-5,6,7,8-tetrahydro-1,8-naphthyridin-3-yl)acrylamide a) N-Methyl-N-(1,2-dimethyl-1H-indol-3-ylmethyl)acrylamide According to the procedure of Example 76 (a), except substituting 1,2-dimethyl-3-(methylaminomethyl)-1H-indole (1.5 g, 8 mmole) for the 1-methyl-2-(methylaminomethyl)-1H-indole, the title compound was prepared and used without further purification.

b) (E)-N-(1,2-Dimethyl-1H-indol-3-ylmethyl)-N-methyl-3-(7-oxo-5,6,7,8-tetrahydro-1,8-naphthyridin-3-yl)acrylamide According to the procedure of Example 76 (b), except substituting 6-bromo-3,4-dihydro-1H-1,8-naphthyridin-2-one-(1.3 g, 5.7 mmole) for the 2-phenylamino-5-bromopyridine, the title compound (0.57 g, 26%) was prepared as a white solid: MS (ES) m/e 389.19 (M+H)$^+$.

Example 81

Preparation of (E)-N-methyl-N-(3-methylbenzo[b]thiophen-2-ylmethyl)-3-(7-oxo-5,6,7,8-tetrahydro-1,8-naphthyridin-3-yl)acrylamide a) N-Methyl-N-(3-methylbenzo[b]thiophen-2-ylmethyl)acrylamide According to the procedure of Example 76 (a), except substituting 2-(methylaminomethyl)-3-methylbenzo[b]thiophene (1.53 g, 8 mmole) for the 1-methyl-2-(methylaminomethyl)-1H-indole, the title compound was prepared and used without further purification.

b) (E)-N-Methyl-N-(3-methylbenzo[b]thiophen-2-ylmethyl)-3-(7-oxo-5,6,7,8-tetrahydro-1,8-naphthyridin-3-yl)acrylamide According to the procedure of Example 76 (b), except substituting 6-bromo-3,4-dihydro-1H-1,8-naphthyridin-2-one (1.3 g, 5.7 mmole) for the 2-phenylamino-5-bromopyridine, the title compound (0.85 g, 33%) was prepared as an off-white solid: MS (ES) m/e 392.2 (M+H)$^+$.

Example 82

Preparation of (E)-3-(6-aminopyridin-3-yl)-N-methyl-(2-methylbenzo[b]thiophen-3-ylmethyl)acrylamide According to the procedure of Example 77, except substituting 2-methyl-3-(methylaminomethyl)benzo[b]thiophene (1.2 g, 6.1 mmole) for the 1,2-dimethyl-3-(methylaminomethyl)-1H-indole, the title compound (1.22 g, 59%) was prepared as a pale yellow solid: MS (ES) m/e 338.2 (M+H)$^+$.

Example 83

Preparation of (E)-3-(6-aminopyridin-3-yl)-N-(3,4-dimethylthieno[2,3-b]thiophen-2-ylmethyl)-N-methylacrylamide According to the procedure of Example 1, except substituting 3,4-dimethyl-2-(methylaminomethyl)thieno[2,3-b]thiophene (0.026 g, 0.126 mmole) for the 1-methyl-2-(methylaminomethyl)-1H-indole, the title compound (0.013 g, 72%) was prepared as a white solid: MS (ES) m/e 358 (M+H)$^+$.

Example 84

Preparation of (E)-3-(6-aminopyridin-3-yl)-N-methyl-N-(1-methylnaphthalen-2-ylmethyl)acrylamide According to the procedure of Example 1, except substituting 1-methyl-2-(methylaminomethyl)naphthalene (0.100 g, 0.54 mmole) for the 1-methyl-2-(methylaminomethyl)-1H-indole, the title compound (0.088 g, 49%) was prepared as a white solid: MS (ES) m/e 332 (M+H)$^+$.

Example 85

Preparation of (E)-3-(6-aminopyridin-3-yl)-N-methyl-N-(1-methyl-1H-pyrrolo[2,3-b]pyridin-3-ylmethyl)acrylamide According to the procedure of Example 1, except substituting 1-methyl-3-(methylaminomethyl)-1H-pyrrolo[2,3-b]pyridine (0.2 g, 1.14 mmole) for the 1-methyl-2-(methylaminomethyl)-1H-indole, the title compound (0.19 g, 52%) was prepared as a white solid: MS (ES) m/e 322 (M+H)$^+$.

Example 86

Preparation of (E)-3-(6-aminopyridin-3-yl)-N-(2,3-dihydro-1H-3a-azacyclopenta[a]inden-8-yl)-N-methylacrylamide According to the procedure of Example 1, except substituting 2,3-dihydro-8-(methylaminomethyl)-1H-3a-azacyclopenta[a]indene (0.100 g, 0.5 mmole) for the 1-methyl-2-(methylaminomethyl)-1H-indole, the title compound (0.063 g, 36%) was prepared as a white solid: MS (ES) m/e 347 (M+H)$^+$.

Example 87

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 88

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 89

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

---

What is claimed is:

1. A compound according to formula (I):

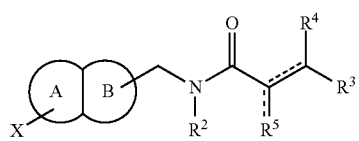

wherein:

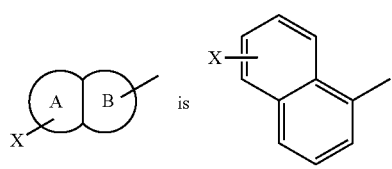 is 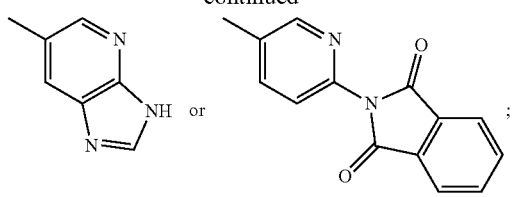

$R^2$ is H, $C_{1-4}$alkyl or $C_{3-6}$cycloalkyl;

$R^3$ is

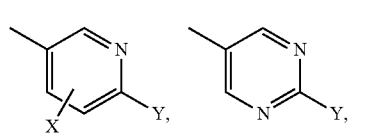

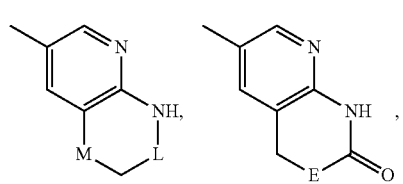

$R^4$ is H or $C_{1-4}$alkyl;

⫝̸ indicates that one of the two designated bonds is a double bond and the other is a single bond;

$R^5$ is $CH_2$ when the bond to which it is attached is a double bond; or $R^5$ is H or $C_{1-4}$alkyl when the bond to which it is attached is a single bond;

Y is H, $C_{1-4}$alkyl, $N(R')_2$, $NHC(O)R'$, $NHCH_2C(O)R'$ or $NHC(O)CH{=}CHR'$;

each X independently is H, $C_{1-4}$alkyl, $CH_2OH$, $OR'$, $SR'$, $CN$, $N(R')_2$, $CH_2N(R')_2$, $NO_2$, $CF_3$, $CO_2R'$, $CON(R')_2$, $COR'$, $NR'C(O)R'$, F, Cl, Br, I or $-S(O)_rCF_3$;

L is $CH_2$ or $C(O)$;

E is O or NR';

each R' independently is H, $C_{1-6}$alkyl or $-C_{0-6}$alkyl-Ar; and r is 0, 1 or 2;

or a pharmaceutically acceptable salt thereof.

2. A compound according to claim 1 of formula (Ia):

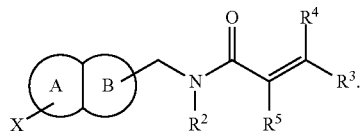
(Ia)

3. A compound according to claim 1 in which $R^3$ is:

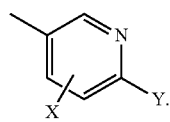

4. A compound according to claim 1 in which $R^3$ is:

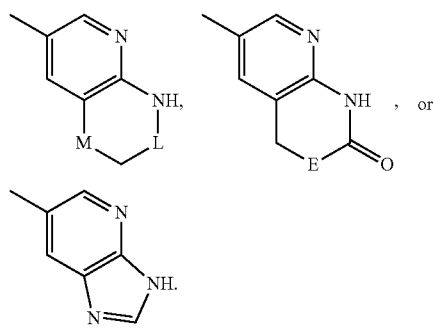

5. A pharmaceutical composition which comprises a compound according to claim 1 and a pharmaceutically acceptable carrier.

6. A method of treating bacterial infections which comprises administering to a subject in need thereof an effective amount of a compound according to claim 1.

7. A compound according to formula (I):

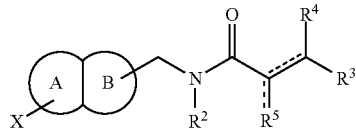
(I)

wherein:

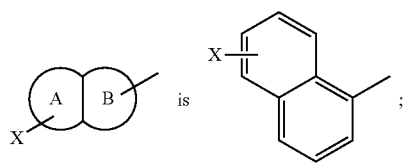

$R^2$ is H, $C_{1-4}$alkyl or $C_{3-6}$cycloalkyl;
$R^3$ is

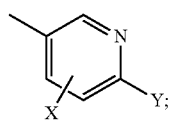

$R^4$ is H or $C_{1-4}$alkyl;

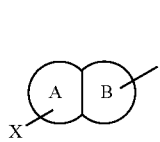

indicates that one of the two designated bonds is a double bond and the other is a single bond;
$R^5$ is $CH_2$ when the bond to which it is attached is a double bond; or $R^5$ is H or $C_{1-4}$alkyl when the bond to which it is attached is a single bond;
Y is $C_{1-4}$alkyl, $N(R')_2$, NHC(O)R', $NHCH_2C(O)R'$ or NHC(O)CH=CHR';
each X independently is H, $CH_2OH$, OR', SR', CN, $N(R')_2$, $CH_2N(R')_2$, $NO_2$, $CF_3$, $CO_2R'$, $CON(R')_2$, COR', NR'C(O)R', F, Cl, Br, I or $—S(O)_rCF_3$;
L is $CH_2$ or C(O);
E is O or NR';
each R' independently is H, $C_{1-6}$alkyl or $—C_{0-6}$alkyl-Ar; and
r is 0, 1 or 2;
or a pharmaceutically acceptable salt thereof.

8. A compound according to formula (I):

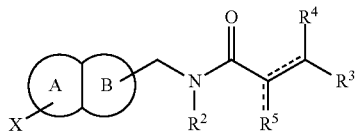
(I)

wherein:

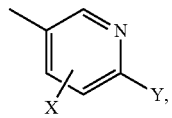

wherein X is H, $CH_2OH$, OR', SR', CN, $N(R')_2$, $CH_2N(R')_2$, $NO_2$, $CF_3$, $CO_2R'$, $CON(R')_2$, COR', NR'C(O)R', F, Cl, Br, I or $—S(O)_rCF_3$;
$R^2$ is H, $C_{1-4}$alkyl or $C_{3-6}$cycloalkyl;
$R^3$ is wherein Y is H, $C_{1-4}$alkyl, $N(R')_2$, NHC(O)R', $NHCH_2C(O)$R' or NHC(O)CH=CHR'; wherein X is $C_{1-4}$alkyl, $CH_2OH$, OR', SR', CN, $N(R')_2$, $CH_2N(R')_2$, $NO_2$, $CF_3$, $CO_2R'$, $CON(R')_2$, COR', NR'C(O)R', F, Cl, Br, I or $-S(O)_rCF_3$;

$R^4$ is H or $C_{1-4}$alkyl;

indicates that one of the two designated bonds is a double bond and the other is a single bond;

$R^5$ is $CH_2$ when the bond to which it is attached is a double bond; or $R^5$ is H or $C_{1-4}$alkyl when the bond to which it is attached is a single bond;

each R' independently is H, $C_1$-6alkyl or $-C_{0-6}$alkyl-Ar; and r is 0, 1 or 2;

or a pharmaceutically acceptable salt thereof.

\* \* \* \* \*